Figure 1:
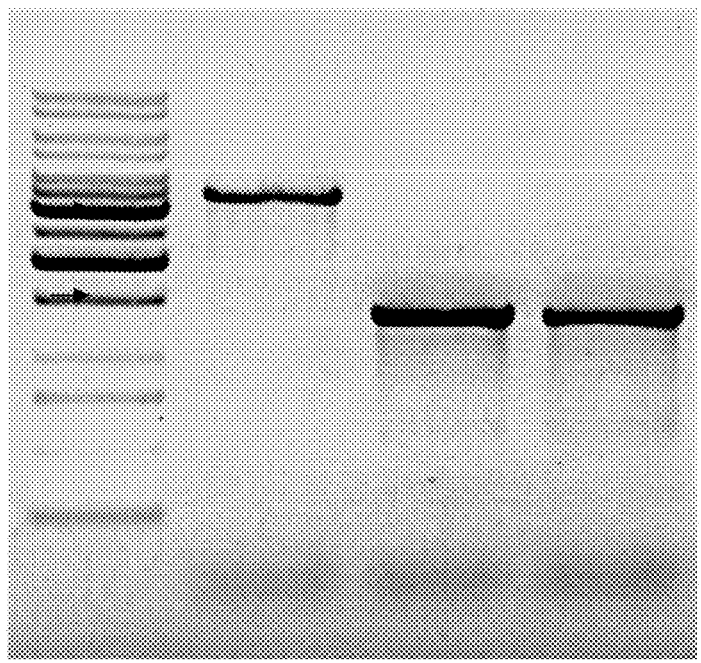

«12» United States Patent
Vindurampulle et al.

(10) Patent No.: US 8,137,930 B2
(45) Date of Patent: Mar. 20, 2012

(54) **ATTENUATED *SALMONELLA ENTERICA* SEROVAR PARATYPHI A AND USES THEREOF**

(75) Inventors: Christofer Vindurampulle, Thornbury (AU); Eileen M. Barry, Ellicott City, MD (

OTHER PUBLICATIONS

Gewirtz, A.T. et al. Cutting edge: bacterial *flagellin* activates basolaterally expressed TLR5 to induce epithelial proinflammatory gene expression. J. Immunol. 167:1882-5, 2001.

Gómez-Duarte, OG, et al., Expression of fragment C of tetanus toxin fused to a carboxyl-terminal fragment of diphtheria toxin in *Salmonella typhi* CVD 908 vaccine strain. Vaccine 13:1596-1602, 1995.

Gómez-Duarte O, et al., Expression, secretion and immunogenicity of the *Plasmodium falciparum* SSP-2 protein in *Salmonella* vaccine strains by a type I secretion system. Infect Immun 69:1192-1198, 2001.

Gonzalez C, et al., *Salmonella typhi* strain CVD 908 expressing the circumsporozoite protein of *Plasmodium falciparum*: strain construction, safety and immunogenicity. J Infect Dis 169:927-931, 1994.

González CR, et al., Immunogenicity of a *Salmonella typhi* CVD 908 candidate vaccine strain expressing the major surface protein gp63 of *Leishmania mexicana mexicana*. Vaccine 16:9/10 1043-1052, 1998.

Herrington DA, et al., Studies in volunteers to evaluate candidate *Shigella* vaccines: further experience with a bivalent *Salmonella typhi-Shigella sonnei* vaccine and protection conferred by previous *Shigella sonnei* disease. Vaccine 8:353-357, 1990.

Hone DM, et al., Construction of genetically-defined double aro mutants of *Salmonella typhi*. Vaccine 9:810-816, 1991.

Hone DM, et al., Evaluation in volunteers of a candidate live oral attenuated *Salmonella typhi* vaccine. J Clin Invest 90:412-420, 1992.

Hone DM, et al., Construction and characterization of isogenic O-antigen variants of *Salmonella typhi*. Molec Microbiol 13:525-530, 1994.

Huleatt, J.W. et al. Vaccination with recombinant fusion proteins incorporating Toll-like receptor ligands induces rapid cellular and humoral immunity. Vaccine. 25:763-75, 2007.

Ibrahim, G.F. et al. Method for the isolation of highly purified *Salmonella* flagellins. J. Clin. Microbiol. 22:1040-4, 1985.

Konadu E et al. Synthesis, characterization, and immunological properties in mice of conjugates composed of detoxified lipopolysaccharide of *Salmonella paratyphi* A bound to tetanus toxoid with emphasis on the role of O acetyls. Infect Immun 64(7):2709-15, 1996.

Koprowski H, et al., Attenuated *Shigella flexneri* 2a vaccine strain CVD 1204 expressing colonization factor antigen I and mutant heat labile enterotoxin of enterotoxigenic *Escherichia coli*. Infect Immun 68:4884 92, 2000.

Kotloff K, et al., Safety, immunogenicity and transmissibility in humans of CVD 1203, a live oral *Shigella flexneri* 2a vaccine candidate attenuated by deletions in aroA and virG. Infect Immun 64:4542-4548, 1996.

Kotloff KL, et al., *Shigella flexneri* 2a strain CVD 1207 with specific deletions in virG, sen, set and guaBA is highly attenuated in humans. Infect Immun 68:1034-39, 2000.

Kotloff KL, et al., Phase I evaluation of ΔvirG *Shigella sonnei* live, attenuated, oral vaccine strain WRSS1 in healthy adults. Infect Immun 70:2016-21, 2002.

Kotloff KL, et al., Deletion in the *Shigella* enterotoxin genes further attenuates *Shigella flexneri* 2a bearing guanine auxotrophy in a Phase 1 trial of CVD 1204 and CVD 1208. J Infect Dis 190:1745-1754, 2004.

Levine MM, et al., Safety, infectivity, immunogenicity and in vivo stability of two attenuated auxotrophic mutant strains of *Salmonella typhi*, 541Ty and 543Ty, as live oral vaccines in man. J Clin Invest 79:888 902, 1987.

Levine MM, et al., Large scale field trial of Ty21a live oral typhoid vaccine in enteric coated capsule formulation. Lancet 1:1049 1052, 1987.

Levine M.M., et al., Safety, Immunogenicity, and Efficacy of Recombinant Live Oral Cholera Vaccines, CVD 103 and CVD 103-hgr. Lancet 332: 467-470, 1988.

Levine MM, et al., Progress in vaccines against typhoid fever. Rev Infect Dis 2 (supplement 3):S552 S567, 1989.

Levine MM, et al., Attenuated *Salmonella* as carriers for the expression of foreign antigens. Microecology and Therapy 19:23-32, 1989.

Levine MM, et al., Comparison of enteric-coated capsules and liquid formulation of Ty21a typhoid vaccine in a randomized controlled field trial. Lancet 336:891-894, 1990.

Levine MM, et al., Clinical and field trials with attenuated *Salmonella typhi* as live oral vaccines and as "carrier vaccines". Res Microbiol 141:807-816, 1990.

Levine MM, et al., Attenuated *Salmonella* as live oral vaccines against typhoid fever and as live vectors. J Biotechnology 44:193-196, 1996.

Levine MM, et al., Attenuated *Salmonella typhi* and *Shigella* as live oral vaccines and as live vectors. Behring Inst Mitt 98:120-123, 1997.

Levine MM, et al., Duration of efficacy of Ty21a, attenuated *Salmonella typhi* live oral vaccine. Vaccine 17:2 Supplement S22-S27, 1999.

Lohman, T.M., et al., *Escherichia coli* single-stranded DNA-binding protein: multiple DNA-binding modes and cooperativities. Annual Reviews in Biochemistry 63:527-70, 1994.

MacLennan, C.A. et al. The neglected role of antibody in protection against bacteremia caused by nontyphoidal strains of *Salmonella* in African children. J Clin. Invest. 118:1553-62, 2008.

Maurizi, M.R. and D. Xia, Protein Binding and Disruption by Clp/Hsp100 Chaperones. Structure (Camb). 12(2):175-83, 2004.

Miller et al. Nucleotide sequence of the partition *locus* of *Escherichia coli* plasmid pSC101, Gene 24:309-15, 1983.

Noriega FR, et al., Construction and characterization of attenuated ΔaroA ΔvirG *Shigella flexneri* 2a strain CVD 1203, a prototype live oral vaccine. Infect Immun 62:5168-5172, 1995.

Noriega FR, et al., Further characterization of ΔaroA, ΔvirG *Shigella flexneri* 2a strain CVD 1203 as a mucosal *Shigella* vaccine and as a live vector for delivering antigens of enterotoxigenic *Escherichia coli*. Infect Immun 64:23-27, 1996.

Noriega FR, et al., Engineered ΔguaBA ΔvirG *Shigella flexneri* 2a strain CVD 1205: construction, safety, immunogenicity, and potential efficacy as a mucosal vaccine. Infect Immun 64:3055-3061, 1996.

Ogushi, K. et al. *Salmonella enteritidis* FliC (flagella filament protein) induces human beta-defensin-2 mRNA production by Caco-2 cells. J. Biol. Chem. 276:30521-6, 2001.

Olanratmanee T, et al., Safety and immunogenicity of *Salmonella typhi* Ty21a liquid formulation vaccine in 4- to 6-year-old Thai children. J Infect Dis 166:451-452, 1992.

Orr N, Galen JE, Levine MM. Expression and immunogenicity of a mutant diphtheria toxin molecule, CRM197, and its fragments in *Salmonella typhi* vaccine strain CVD 908-htrA. Infect Immun 67:4290-4294, 1999.

Orr N, Galen JE, Levine MM. Novel use of anaerobically induced promoter, dmsA, for controlled expression of Fragment C of tetanus toxin in live attenuated *Salmonella enterica* serovar *Typhi* strain CVD 908-htrA. Vaccine 19:1694 1700, 2001.

Pasetti MF, et al., Attenuated ΔguaBA *Salmonella typhi* vaccine strain CVD 915 as a live vector utilizing prokaryotic or eukaryotic expression systems to deliver foreign antigens and elicit immune responses. Clin Immun 92:76-89, 1999.

Pasetti MF, et al., Mechanisms and cellular events associated with the priming of mucosal and systemic immune responses to *Salmonella enterica* serovar *Typhi* live vector vaccines delivered intranasally in the murine model. Vaccine 18:3208-3213, 2000.

Pasetti, M, et al., Animal models paving the way for clinical trials of attenuated *Salmonella enterica* serovar *Typhi* live oral vaccines and live vectors. Vaccine. 21:401-18, 2003.

Pasetti MF, et al., Attenuated *Salmonella enterica* serovar *Typhi* and *Shigella flexneri* 2a strains mucosally deliver DNA vaccines encoding measles virus hemagglutinin, inducing specific immune responses and protection in cotton rats. J Virol 77:5209-5217, 2003.

Pickard D, et al., Characterization of defined ompR mutants of *Salmonella typhi*: ompR is involved in the regulation of Vi polysaccharide expression. Infect Immun 62:3984-3993, 1994.

Pratt, L.A. et al., From acids to osmZ: multiple factors influence synthesis of the OmpF and OmpC porins in *Escherichia coli*. Molecular Microbiology 20:911-7, 1996.

Salerno-Goncalves R, et al., Concomitant Induction of CD4(+) and CD8(+) T Cell Responses in Volunteers Immunized with *Salmonella enterica* Serovar *Typhi* Strain CVD 908-htrA. J Immol. 170:2734-2741, 2003.

Servos S, et al., Molecular cloning and characterization of the aroD gene encoding 3-dehydroguinase from *Salmonella typhi*. J Gen Micro 137:147-152, 1990.

Sztein MB, et al., Cytokine production patterns and lymphoproliferative responses in volunteers orally immunized with attenuated vaccine strains of *Salmonella typhi*. J Infect Dis 170:1508-1517, 1994.

Sztein MB, et al., Cytotoxic T lymphocytes after oral immunization with attenuated strains of *Salmonella typhi* in humans. J Immunol 155:3987-3993, 1995.

Tacket CO, et al., Lack of immune response to the Vi component of a Vi-positive variant of the *Salmonella typhi* live oral vaccine strain Ty21a in volunteer studies. J Infect Dis 163:901-904, 1991.

Tacket CO, et al., Comparison of the safety and immunogenicity of ΔaroC ΔaroD and Δcya Δcrp *Salmonella typhi* strains in adult volunteers. Infect Immun 60:536-541, 1992.

Tacket CO, et al., Clinical acceptability and immunogenicity of CVD 908 *Salmonella typhi* vaccine strain. Vaccine 10:443-446, 1992.

Tacket CO, et al., Safety of live oral *Salmonella typhi* vaccine strains with deletions in htrA and aroC aroD and immune response in humans. Infect Immun 65:452-456, 1997.

Tacket CO, et al., Safety and immunogenicity in humans of an attenuated *Salmonella* Typhivaccine vector strain expressing plasmid-encoded hepatitis B antigens stabilized by the Asd-balanced lethal system. Infect Immun 65:3381-3385, 1997.

Tacket CO, et al., Phase 2 clinical trial of attenuated *Salmonella enterica* serovar *Typhi* oral live vector vaccine CVD 908-htrA in U.S. volunteers. Infect Immun 68:1196-1201, 2000.

Tacket CO, et al., Safety and immune responses to attenuated *Salmonella enterica* serovar *Typhi* oral live vector vaccines expressing tetanus toxin fragment C. Clin Immunol 97:146-153, 2000.

Tacket CO, et al., Immune responses to an oral Typhoid vaccine strain modified to constitutively express Vi capsular polysaccharide. J Infect Dis, 190:565-570, 2004.

Van de Verg L, et al., Specific IgA secreting cells in peripheral blood following oral immunization with bivalent *Salmonella typhi/Shigella sonnei* vaccine or infection with pathogenic *S. sonnei* in humans. Infect Immun 58:2002-2004, 1990.

Vindurampulle CJ, et al., Recombinant *Salmonella enterica* serovar *Typhi* in a prime-boost strategy. Vaccine 22 (27-28):3744-3750, 2004.

Wang JY, et al., Constitutive expression of the Vi polysaccharide capsular antigen in attenuated *Salmonella enterica* serovar *Typhi* oral vaccine strain CVD 909. Infect Immun 68:4647-4652, 2000.

Wang JY, et al., Construction, genotypic and phenotypic characterization, and immunogenicity of attenuated ΔguaBA *Salmonella enterica* serovar *Typhi* strain CVD 915. Infect Immun 69:4734-4741, 2001.

Wu S, et al., Construction and immunogenicity in mice of attenuated *Salmonella typhi* expressing *Plasmodium falciparum* merozoite surface protein (MSP-1) fused to tetanus toxin fragment C. J Biotechnol. 83:125 135, 2000.

Yamamoto, T. et al., Disruption of the Genes for ClpXP Protease in *Salmonella enterica* Serovar Typhimurium Results in Persistent Infection in Mice, and Development of Persistence Requires Endogenous Gamma Interferon and Tumor Necrosis Factor Alpha. Infect Immun. 69(5):3164-74, 2001.

Yoon, S.S. et al. Decreased potency of the Vibrio cholerae sheathed flagellum to trigger host innate immunity. Infect. Immun. 76:1282-8, 2008.

Komoriya, K. et al., Flagellar proteins and type III-export virulence factors. Molecular Microbiology 34:767-779, 1999.

Brett, P.J., et al., Structural and immunological characterization of Burkholderia pseudomallei O-polysaccharide-Flagellin protein conjugates. Infect. Immun. 64:2824-2828, 1996.

Thomsen, L.E. *Salmonella* genes required for virulence and stress response. Characterization of ClpP and RfbM [online] Ph.D. Thesis, Dept. of Veter. Microbiol., The Royal Veter. Agric. Univ., Denmark, Jan. 2002, pp. 1-148 (esp. p. 42), available at: www.forskningsbase.life.ku.dk/fbspretrieve/13549041/Line_Elnif_Thomsen.pdf.

Liu, S,-L. et al. The Chromosome of *Salmonella* paratyphiA is INverted by Recombination between rrnH and rrnG. J. Bacteriol. Nov. 1995, vol. 177, No. 22, pp. 6585-6592 (esp. abstract).

International Search Report and Written Opinion for PCT/US06/42148, dated Feb. 24, 2011.

International Search Report and Written Opinion for PCT/US10/25221, dated Oct. 27, 2010.

Arya et al., Urgent Need for an Effective Vaccine Against Vaccine *Salmonella paratyphi* A, B and C. Dec. 1995, 13(17):1727-1728.

\* cited by examiner

Figure 6

Figure 10A

```
                          10         20         30         40         50         60
Typhimurium       tcacgcacac gctgcaggtt gttgttgatt tcgttcagcg cgccttcagt ggtctgcgca
Typhi A           tcacgcacac gctgcaggtt gttgttgatt tcgttcagcg cgccttcagt ggtctgcgca
Ty2               tcacgcacac gctgcaggtt gttgttgatt tcgttcagcg cgccttcagt ggtctgcgca 70         80         90        100        110        120
Typhimurium       atggagatac cgtcgttagc gttacgggaa gcctgagtca gacctttgat gttcgcggta
Typhi A           atggagatac cgtcgttagc gttacgggaa gcctgagtca gacctttgat gttcgcggtg
Ty2               atggagatac cgtcgttagc gttacgggaa gcctgagtca gacctttgat gttcgcggta 130        140        150        160        170        180
Typhimurium       aaacggttag caatcgcctg acctgccgca tcgtctttcg cgctgttgat acgcagaccg
Typhi A           aaacggttag caattgcctg acctgccgca tcgtctttcg cgctgttgat acgcagaccg
Ty2               aaacggttag caatcgcctg tcctgccgca tcgtctttcg cgctgttgat acgcagaccg 190        200        210        220        230        240
Typhimurium       gaagacagac gctcgatagc ggtgcccaga gcggactggg atttgttcag gttattctgg
Typhi A           gaagacagac gctcgatagc ggtgcccaga gcggactggg atttgttcag gttattctgg
Ty2               gaagacaaac gctcgatagc agtgcccagt gcggactggg atttgttcag gttattctgg 250        260        270        280        290        300
Typhimurium       gtcaacagcg acaggctgtt tgtattaatg acttgtgcca tgatctttc cttatcaatt
Typhi A           gtcaacagcg acaggctgtt tgtattaatg acttgtgcca tgatctttc cttatcaatt
Ty2               gtcaacagcg acaggctgtt tgtattaatg acttgtgcca tgatctttc cttatcaatt 310        320        330        340        350        360
Typhimurium       acaacttgat gttattgggc tgttgcccac ggtttctcac cgtaacccct gtatcggcac
Typhi A           acaacttgat gttattgggc tgttgcccac ggtttctcac cgtaacccct gtatcggcac
Ty2               acaacttgat gttattgggc tgttgcccac ggtttctcac cgtaacccct gtatcggcac 370        380        390        400        410        420
Typhimurium       ctgaatttcg aactttagaa aattttcac ttcccccgat ctttttctta ggcggcgaaa
Typhi A           ctgaatttcg aactttagaa aattttcac ttcccccgat ctttttctta ggcggcgaaa
Ty2               ctgaatttcg aactttagaa aattttcac ttcccccgat ctttttctta ggcggcgaaa 430        440        450        460        470        480
Typhimurium       tagccgcttt atgcatcatt attccgcgca ttatttttgc aaaattatca ttaaactttg
Typhi A           tagccgcttt atgcatcatt attccgcgca ttatttttgc aaaattatca ttaaactttg
Ty2               tagccgcttt atgcatcatt attccgcgca ttatttttgc aaaattatca ttaaactttg 490        500        510        520        530        540
Typhimurium       cctccagatt gccgataacg cgcttaacta ctgtttgcaa tcaaaaagga agaaggcatg
Typhi A           cctccagatt gccgataacg cgcttaacta ctgtttgcaa tcaaaaagga agaaggcatg
Ty2               cctccagatt gccgataacg cgcttaacta ctgtttgcaa tcaaaaagga agaaggcatg 550        560        570        580        590        600
Typhimurium       gcttcaattt catcattagg tgtgggatca aacttaccgt tagaccagtt gttgacagac
Typhi A           gcttcaattt catcattagg tgtgggatca aacttaccgt tagaccagtt gttgacagac
Ty2               gcttcaattt catcattagg tgtgggatca aacttaccgt tagaccagtt gttgacagac 610        620        630        640        650        660
Typhimurium       ctgacaaaga acgaaaaagg acgcttaacg ccaattacca aacagcagag cgcgaattcg
Typhi A           ctgacaaaga acgaaaaagg acgcttaacg ccaattacca aacagcagag cgcgaattcg
Ty2               ctgacaaaga acgaaaaagg acgcttaacg ccaattacca aacagcagag cgcgaattcg
```

Figure 10B

```
                          670        680        690        700        710        720
Typhimurium      gcaaagctaa ccgcctatgg cacattgaaa agcgcattag aaaaattcca gacggcaaat
Typhi A          gcaaagctaa ccgcctatgg cacattgaaa agcgcattag aaaaattcca gacggcaaat
Ty2              gcaaagctaa ccgcctatgg cacattgaaa agcgcattag aaaaattcca gacggcaaat 730        740        750        760        770        780
Typhimurium      accgcgttaa ataaagcgga tttatttaag tctaccgtgg cgtccagcac c̲actga̲agat̲
Typhi A          accgcgttaa ataaagcgga tttatttaag tctaccgtgg cgtccagcac gacagaggac
Ty2              accgcgttaa ataaagcgga tttatttaag tctaccgtgg cgtccagcac gacagaggac 790        800        810        820        830        840
Typhimurium      ctcaaagtca gtactaccgc t̲ggcgctgcc gcagggactt ataagattaa̲ cgtaacccag
Typhi A          ctcaaagtca gtactaccgc aggcgctgcc gcagggactt ataagattag cgtaacccag
Ty2              ctcaaagtca gtactaccgc aggcgctgcc gcagggactt ataagattag cgtaacccag 850        860        870        880        890        900
Typhimurium      cttgccgccg ca̲cagtcgct ggcgacaaaa accaccttcg cg̲accaccaa agagcagttg
Typhi A          cttgccgccg cgcagtcgct ggcgacaaaa accaccttcg caaccaccaa agagcagttg
Ty2              cttgccgccg cgcagtcgct ggcgacaaaa accaccttcg caaccaccaa agagcagttg 910        920        930        940        950        960
Typhimurium      ggcgatacgt cggtcacgtc ccggacaatt aaaattgaac agccgggacg taaagagccg
Typhi A          ggcgatacgt cggtcacgtc ccggacaatt aaaattgaac agccgggacg taaagagccg
Ty2              ggcgatacgt cggtcaca̲tc ccggacaatt aaaattgaac agccgggacg taaagagccg 970        980        990       1000       1010       1020
Typhimurium      ctggaaatta agctggataa aggcgacacc tccatggagg cgatccgtga cgccatcaat
Typhi A          ctggaaatta agctggataa aggcgacacc tccatggagg cgatccgtga cgccatcaat
Ty2              ctggaaatta agctggataa aggcgacacc tccatggagg cgatccgtga cgccatt̲aat 1030       1040       1050       1060       1070       1080
Typhimurium      gacgccgaca gcggtatcgc cgccagtatc gttaaggtca aagagaacga attccagttg
Typhi A          gacgccgaca gcggtatcgc cgccagtatc gttaaggtca aagagaacga attccagttg
Ty2              gacgccgaca gcggtatcgc cgccagtatc gttaaggtca aagagaacga attccagttg 1090       1100       1110       1120       1130       1140
Typhimurium      gtgcttaccg ccaatagcgg taccgacaat acgatgaaga tcacggtgga aggcgataca
Typhi A          gtgcttaccg ccaatagcgg taccgacaat acgatgaaga tcacggtgga aggcgataca
Ty2              gtgcttaccg ccaatagcgg taccgacaat acgatgaaga tcacggtgga aggcgataca 1150       1160       1170       1180       1190       1200
Typhimurium      aaacttaacg atctactcgc ttatgacagc accaccaata ccggcaatat gcaagagctg
Typhi A          aaacttaacg atctactcgc ttatgacagc accaccaata ccggcaatat gcaagagctg
Ty2              aaacttaacg atctactcgc ttatgacagc accaccaata ccggcaatat gcaagagctg 1210       1220       1230       1240       1250       1260
Typhimurium      gtgaaagcag aaaacgcgaa gctgaacgta aacggcatcg acattgagcg tcagagcaat
Typhi A          gtgaaagcag aaaacgcgaa gctgaacgta aacggcatcg acattgagcg tcagagcaat
Ty2              gtgaaagcag aaaacgcgaa gctgaacgta aacggcatcg acattgagcg tcagagcaat 1270       1280       1290       1300       1310       1320
Typhimurium      accgtaaccg acgcccctca gggaattacg ctcaccctga ccaagaaagt gaccgacgcg
Typhi A          accgtaaccg acgcccctca gggaattacg ctcaccctga cg̲aagaaagt gaccgacgcg
Ty2              accgtaaccg acgcccctca gggaattaca̲ ctcaccctga ccaagaaagt gaccgacgcg
```

Figure 10C

```
                        1330       1340       1350       1360       1370       1380
Typhimurium   accgtgacgg taacgaaaga tgataccaag gcgaaagagg cgattaaatc ctgggtggat
Typhi A       accgtgacgg taacgaaaga tgataccaag gcgaaagagg cgattaaatc ctgggtggat
Ty2           accgtgacgg tgacgaaaga tgataccaag gcgaaagagg cgattaaatc ctgggtggat 1390       1400       1410       1420       1430       1440
Typhimurium   gcctataact cgctggtgga tacctttagc tcgttaacca aatataccgc cgttgagccg
Typhi A       gcctataact cgctggtgga tacctttagc tcgttaacca aatataccgc cgttgagccg
Ty2           Gcctataact cgctggtgga tactttagc tcattaacta aatataccgc cgttgagccg 1450       1460       1470       1480       1490       1500
Typhimurium   ggcgaagaag ccagcgataa aaacggcgcg ctgttaggcg atagtgtggt tcgtactatc
Typhi A       ggcgaagaag ccagcgataa aaacggcgcg ctgttaggcg atagtgtggt tcgtactatc
Ty2           ggcgaagaag ccagcgataa aaacggcgcg ctgttaggcg atagtgtggt tcgtgctatc 1510       1520       1530       1540       1550       1560
Typhimurium   cagaccggga ttcgggcaca atttgccaat agcggcagta attctgcgtt caaaacaatg
Typhi A       cagaccggga ttcgggcaca atttgccaat agcggcagta attctgcgtt caaaacaatg
Ty2           cagaccggga ttcgggcaca atttgccaat agcggcagta attctgcgtt caaaacaatg 1570       1580       1590       1600       1610       1620
Typhimurium   gcggaaattg gcatcaccca ggatgggact tccggcaaac tgaagattga tgatgataag
Typhi A       gcggaaattg gcatcaccca ggatgggact tccggcaaac tgaagattga tgatgataag
Ty2           gcggaaattg gcatcaccca ggatgggact tccggcaaac tgaagattga cgatgataag 1630       1640       1650       1660       1670       1680
Typhimurium   ctgaccaaag tactgaaaga taacacagcc gcagcgcgtg agctgctggt aggcgatggt
Typhi A       ctgaccaagg tactgaaaga taacacagcc gcagcgcgtg agctgctggt aggcgatggt
Ty2           ctgaccaagg tactgaaaga taacacggcc gcagcgcgtg agctgctggt aggcgatggt 1690       1700       1710       1720       1730       1740
Typhimurium   aaagaaacgg gtatcaccac caaaattgcc accgaagtga aaagttatct ggcggatgac
Typhi A       aaagaaacgg gtatcaccac caaaattgcc accgaagtga aaagttatct ggcggatgac
Ty2           aaagaaacgg gtatcaccac caaaattgcc accgaagtga aaagttatct ggcggatgac 1750       1760       1770       1780       1790       1800
Typhimurium   ggcattattg ataatgcgca ggacaacgtt aacgccacgc tgaaaagcct gacaaaacag
Typhi A       ggcattattg ataatgcgca ggacaacgtt aacgccacgc tgaaaagcct gacaaaacag
Ty2           ggcattattg ataatgcgca ggacaacgtt aacgccacgc tgaaaagcct gacaaaacag 1810       1820       1830       1840       1850       1860
Typhimurium   tacctgtccg ttagcaacag catcgatgaa accgttgccc gttacaaggc ccagtttacc
Typhi A       tacctgtccg ttagcaacag catcgatgaa accgttgccc gttacaaggc ccagtttacc
Ty2           tacctgtccg ttagcaacag catcgatgaa accgttgccc gttacaaggc ccagtttacc 1870       1880       1890       1900       19120      1920
Typhimurium   caactggata ccatgatgag taagctgaat aacaccagta gttatttgac ccagcaattt
Typhi A       caactggata ctatgatgag taagctgaat aacaccagta gttatttgac ccagcaattt
Ty2           caactggata ccatgatgag taagctgaat aacaccagta gttatttgac ccagcaattt 1930       1940       1950       1960       1970       1980
Typhimurium   acagctatga acaagtcctg ataacagagg tcaccatgta caccgcgagc ggtatcaaag
Typhi A       acagctatga acaagtcctg ataacagagg tcaccatgta caccgcgagc ggtatcaaag
Ty2           acagctatga acaagtcctg ataacagagg tcaccatgta caccgcgagc ggtatcaaag
```

Figure 10D

```
                     1990       2000       2010       2020       2030       2040
Typhimurium   cttatgcgca agtcagcgtg gaaagcgccg tgatgagcgc cagcccgcat cagttgattg
Typhi A       cttatgcgca agtcagcgtg gaaagcgccg tgatgagcgc cagcccgcat cagttgattg
Ty2           cttatgcgca agtcagcgtg gaaagcgccg tgatgagcgc cagcccgcat cagttgattg 2050       2060       2070       2080       2090       2100
Typhimurium   aaatgttgtt tgatggcgcg aatagcgctc tggtgcgcgc tcgcctgttt ttagaacaag
Typhi A       aaatgttgtt tgatggcgcg aatagcgctc tggtgcgcgc tcgcctgttt ttagaacaag
Ty2           aaatgttgtt tgatggcgcg aatagcgctc tggtgcgcgc tcgcctgttt ttagaacaag 2110       2120       2130       2140       2150       2160
Typhimurium   gcgatgttgt cgcgaaaggt gaagcgttaa gcaaagccat caatattatc gataacgggc
Typhi A       gcgatgttgt cgcgaaaggt gaagcgttaa gcaaagccat caatattatc gataacgggc
Ty2           gcgatgttgt cgcgaaaggt gaagcgttaa gcaaagccat caatattatc gataacgggc 2170       2180       2190       2200       2210       2220
Typhimurium   tgaaagccgg cctcgatcag gaaaaaggcg gtgagattgc gacgaatctt tccgagctat
Typhi A       tgaaagccgg cctcgatcag gaaaaaggcg gtgagattgc gacgaatctt tccgagctat
Ty2           tgaaagccgg cctcgatcag gaaaaaggcg gtgagattgc gacgaatctt tccgagctat 2230       2240       2250       2260       2270       2280
Typhimurium   acgactatat gattcgccgt ttactgcagg ctaatttgcg taacgacgct caggccatcg
Typhi A       acgactatat gattcgccgt ttactgcagg ctaatttgcg taacgacgct caggccatcg
Ty2           acgactatat gattcgccgt ttactgcagg ctaatttgcg taacgacgct caggccatcg 2290       2300       2310       2320       2330       2340
Typhimurium   aagaagtgga agggttactc agcaatattg cagaagcctg gaagcagatt tcaccgaaag
Typhi A       aagaagtgga agggttactc agcaatattg cagaagcctg gaagcagatt tcaccgaaag
Ty2           aagaagtgga a<u>a</u>ggttactc agcaatattg cagaagcctg gaagcagatt tcaccgaaag 2350       2360
Typhimurium   catctttcca ggagtctcgt taa
Typhi A       catctttcca ggagtctcgt taa
Ty2           catctttcca ggagtctcgt taa
```

Figure 10E

|  | 10 | 20 | 30 | 40 | 50 | 60 |
|---|---|---|---|---|---|---|
| Enteritidis | tcacgcacac | gctgcaggtt | gttgttgatt | tcattcagcg | caccttcagt | ggtctgcgca |
| Typhimurium | tcacgcacac | gctgcaggtt | gttgttgatt | tcgttcagcg | cgccttcagt | ggtctgcgca |

|  | 70 | 80 | 90 | 100 | 110 | 120 |
|---|---|---|---|---|---|---|
| Enteritidis | atagaaatgc | cgtcgttagc | gttacgggaa | gcctgagtca | gacctttgat | attagaagtg |
| Typhimurium | atggagatac | cgtcgttagc | gttacgggaa | gcctgagtca | gacctttgat | gttcgcggta |

|  | 130 | 140 | 150 | 160 | 170 | 180 |
|---|---|---|---|---|---|---|
| Enteritidis | aagcggttag | caatcgcctg | gcctgccgca | tcgtctttcg | cgctgttgat | acgcagacca |
| Typhimurium | aaacggttag | caatcgcctg | acctgccgca | tcgtctttcg | cgctgttgat | acgcagaccg |

|  | 190 | 200 | 210 | 220 | 230 | 240 |
|---|---|---|---|---|---|---|
| Enteritidis | gaggacagac | gctcaatagc | ggaactcagt | gaggactgag | atttgttcag | gttattctgg |
| Typhimurium | gaagacagac | gctcgatagc | ggtgcccaga | gcggactggg | atttgttcag | gttattctgg |

|  | 250 | 260 | 270 | 280 | 290 | 300 |
|---|---|---|---|---|---|---|
| Enteritidis | gtcaacagcg | acaggctgtt | tgtattaatg | acttgtgcca | tgatcttttc | cttatcaatt |
| Typhimurium | gtcaacagcg | acaggctgtt | tgtattaatg | acttgtgcca | tgatcttttc | cttatcaatt |

|  | 310 | 320 | 330 | 340 | 350 | 360 |
|---|---|---|---|---|---|---|
| Enteritidis | acaacttgat | gttattgggc | tgttgcccac | ggtttctcac | cgtaacccct | gtatcggcac |
| Typhimurium | acaacttgat | gttattgggc | tgttgcccac | ggtttctcac | cgtaacccct | gtatcggcac |

|  | 370 | 380 | 390 | 400 | 410 | 420 |
|---|---|---|---|---|---|---|
| Enteritidis | ctgaatttcg | aactttagaa | aattttttcac | ttcccccgat | cttttttctta | gcctgcgaaa |
| Typhimurium | ctgaatttcg | aactttagaa | aattttttcac | ttcccccgat | cttttttctta | ggcggcgaaa |

|  | 430 | 440 | 450 | 460 | 470 | 480 |
|---|---|---|---|---|---|---|
| Enteritidis | tagccgcttt | atgcatcatt | attccacgca | ttattttttgc | aaaattatca | ttaaactttg |
| Typhimurium | tagccgcttt | atgcatcatt | attccgcgca | ttattttttgc | aaaattatca | ttaaactttg |

|  | 490 | 500 | 510 | 520 | 530 | 540 |
|---|---|---|---|---|---|---|
| Enteritidis | cttccagatt | gccgataacg | cgtttaacta | ctgtttgcaa | tcgaaaNgga | agatggcatg |
| Typhimurium | cctccagatt | gccgataacg | cgcttaacta | ctgtttgcaa | tcaaaaagga | agaaggcatg |

|  | 550 | 560 | 570 | 580 | 590 | 600 |
|---|---|---|---|---|---|---|
| Enteritidis | gcttcaattt | catcattagg | tgtagggtca | aacttacctc | tggattcact | gctgactaaa |
| Typhimurium | gcttcaattt | catcattagg | tgtgggatca | aacttaccgt | tagaccagtt | gttgacagac |

|  | 610 | 620 | 630 | 640 | 650 | 660 |
|---|---|---|---|---|---|---|
| Enteritidis | ctgaccaacg | ctgaaaaagg | acgcttaacg | ccgatcacac | agcagcagag | tgctaatacg |
| Typhimurium | ctgacaaaga | acgaaaaagg | acgcttaacg | ccaattacca | aacagcagag | cgcgaattcg |

|  | 670 | 680 | 690 | 700 | 710 | 720 |
|---|---|---|---|---|---|---|
| Enteritidis | gcccgtctaa | cggcatacgg | tactttaaaa | agtgcactgg | agaagtttca | aacagcaaac |
| Typhimurium | gcaaagctaa | ccgcctatgg | cacattgaaa | agcgcattag | aaaaattcca | gacggcaaat |

Figure 10F

```
                    730        740        750        760        770        780
Enteritidis    acggcgttaa ataaagccga tctgtttaaa agtacgaatg tcaccagcag tacagaagac
Typhimurium    accgcgttaa ataaagcgga tttatttaag tctaccgtgg cgtccagcac cactgaagat 790        800        810        820        830        840
Enteritidis    ctgaaagtct cgacggaagc tggggccgca cctggaactt atgtggttag cgtaactcag
Typhimurium    ctcaaagtca gtactaccgc tggcgctgcc gcagggactt ataagattaa cgtaacccag 850        860        870        880        890        900
Enteritidis    ttagcacaag cacaatcttt gagtacagca accaaaatta catctaccaa agaagtgctg
Typhimurium    cttgccgccg cacagtcgct ggcgacaaaa accaccttcg cgaccaccaa agagcagttg 910        920        930        940        950        960
Enteritidis    ggagatacca catctgacag ccgtaccata aaaattgaac agaaaggccg taaagaacca
Typhimurium    ggcgatacgt cggtcacgtc ccggacaatt aaaattgaac agccgggacg taaagagccg 970        980        990       1000       1010       1020
Enteritidis    cttgaaatca agctcactaa agatcaaacc tctttagagg gtatccgtga cgccattaat
Typhimurium    ctggaaatta agctggataa aggcgacacc tccatggagg cgatccgtga cgccatcaat 1030       1040       1050       1060       1070       1080
Enteritidis    gatgctgaca gtcgtatttc cgccagtatc gttaaagtta aagaaggcga ttatcagctt
Typhimurium    gacgccgaca gcggtatcgc cgccagtatc gttaaggtca aagagaacga attccagttg 1090       1100       1110       1120       1130       1140
Enteritidis    gtactgaccg cagatagtgg cacggataat caaatgacta tctctgtgga aggcgatagc
Typhimurium    gtgcttaccg ccaatagcgg taccgacaat acgatgaaga tcacggtgga aggcgataca 1150       1160       1170       1180       1190       1200
Enteritidis    aaactcagcg atctgttgtc ctatgatagt agtactggca cgggcaaaat gaagcaactg
Typhimurium    aaacttaacg atctactcgc ttatgacagc accaccaata ccggcaatat gcaagagctg 1210       1220       1230       1240       1250       1260
Enteritidis    gttgctgcag ataatgcttt gttaaccgtt aacggcattg atattgagcg accgagtaat
Typhimurium    gtgaaagcag aaaacgcgaa gctgaacgta acggcatcg acattgagcg tcagagcaat 1270       1280       1290       1300       1310       1320
Enteritidis    aaaatcactg acgctccaca aggcgtgacg cttgaactaa ccaaagaagt aaaagatgcc
Typhimurium    accgtaaccg acgccctca gggaattacg ctcaccctga ccaagaaagt gaccgacgcg 1330       1340       1350       1360       1370       1380
Enteritidis    cgtattaccg tcacaaaaga taatgaaaag gcgaccgaag ccgtcaaagg ttgggttgat
Typhimurium    accgtgacgg taacgaaaga tgataccaag gcgaagagg cgattaaatc ctgggtggat 1390       1400       1410       1420       1430       1440
Enteritidis    gcctacaact cactgcttga tacctttagt tcattaacaa aatatacaga ggttgatcca
Typhimurium    gcctataact cgctggtgga tacctttagc tcgttaacca aatataccgc cgttgagccg
```

Figure 10G

```
               1450       1460       1470       1480       1490       1500
Enteritidis    ggggctgaag aacaggacaa aaacaacggt gcactacttg gagataccgt ggtgcgaacg
Typhimurium    ggcgaagaag ccagcgataa aaacggcgcg ctgttaggcg atagtgtggt tcgtactatc 1510       1520       1530       1540       1550       1560
Enteritidis    attcaaactg gaatccgcgc tcagttcgct aatggtgcaa gtacaggtac atttaagacc
Typhimurium    cagaccggga ttcgggcaca atttgccaat agcggcagta attctgcgtt caaaacaatg 1570       1580       1590       1600       1610       1620
Enteritidis    ctgaatgaaa ttggtattac ttctgatggt accaccggaa aactaaaaat tgatgatacc
Typhimurium    gcgNNNgaaa ttggcatcac ccaggatggg acttccggca aactgaagat tgatgatgat 1630       1640       1650       1660       1670       1680
Enteritidis    aagcttaaaa aagcgctgga tgaaaatacc gcttctgtac gtgagctgct ggtaggtgat
Typhimurium    aagctgacca aagtactgaa agataacaca gccgcagcgc gtgagctgct ggtaggcgat 1690       1700       1710       1720       1730       1740
Enteritidis    ggtaaagaaa cggggatcac caccaaaatt gccaccgaag tgaaaagtta tctggccgat
Typhimurium    ggtaaagaaa cgggtatcac caccaaaatt gccaccgaag tgaaaagtta tctggcggat 1750       1760       1770       1780       1790       1800
Enteritidis    gacggcatta ttgacagcgc ccaggacagt attaacgcca cgctgaaaaa gctgactaag
Typhimurium    gacggcatta ttgataatgc gcaggacaac gttaacgcca cgctgaaaag cctgacaaaa 1810       1820       1830       1840       1850       1860
Enteritidis    caatatctga ccgtcagcag tagcattgac gacaccgttg cccgttacaa ggcccagttt
Typhimurium    cagtacctgt ccgttagcaa cagcatcgat gaaaccgttg cccgttacaa ggcccagttt 1870       1880       1890       1900       1910       1920
Enteritidis    acccaactgg ataccatgat gagtaagctg aataacacca gtacttattt gacccagcaa
Typhimurium    acccaactgg ataccatgat gagtaagctg aataacacca gtagttattt gacccagcaa 1930       1940       1950       1960       1970       1980
Enteritidis    tttaatgcta tgaacaagtc ctgataacag aggttaccat gtacaccgcg agcggtatca
Typhimurium    tttacagcta tgaacaagtc ctgataacag aggtcaccat gtacaccgcg agcggtatca 1990       2000       2010       2020       2030       2040
Enteritidis    aagcttatgc gcaagtcagc gtggaaagcg ccgtgatgag cgccagcccg catcagttga
Typhimurium    aagcttatgc gcaagtcagc gtggaaagcg ccgtgatgag cgccagcccg catcagttga 2050       2060       2070       2080       2090       2100
Enteritidis    ttgaaatgtt gtttgatggc gcgaatagcg ctctggtgcg cgctcgcctg ttttagaac
Typhimurium    ttgaaatgtt gtttgatggc gcgaatagcg ctctggtgcg cgctcgcctg ttttagaac 2110       2120       2130       2140       2150       2160
Enteritidis    aaggcgatgt tgtcgcgaaa ggtgaagcgt taagcaaagc catcaatatt atcgataacg
Typhimurium    aaggcgatgt tgtcgcgaaa ggtgaagcgt taagcaaagc catcaatatt atcgataacg
```

Figure 10H

```
                    2170       2180       2190       2200       2210       2220
Enteritidis    ggctgaaagc cggcctcgat caggaaaaag gcggtgagat tgcgacgaat ctttccgagc
Typhimurium    ggctgaaagc cggcctcgat caggaaaaag gcggtgagat tgcgacgaat ctttccgagc 2230       2240       2250       2260       2270       2280
Enteritidis    tatacgacta tatgattcgc cgtttactgc aggctaattt gcgtaacgac gctcaggcca
Typhimurium    tatacgacta tatgattcgc cgtttactgc aggctaattt gcgtaacgac gctcaggcca 2290       2300       2310       2320       2330       2340
Enteritidis    Tcgaagaagt ggaagggtta ctcagcaata ttgcagaagc ctggaagcag atttcaccga
Typhimurium    tcgaagaagt ggaagggtta ctcagcaata ttgcagaagc ctggaagcag atttcaccga 2350       2360
Enteritidis    Aagcatcttt ccaggagtct cgttaa
Typhimurium    Aagcatcttt ccaggagtct cgttaa
```

ATTENUATED *SALMONELLA ENTERICA* SEROVAR PARATYPHI A AND USES THEREOF

RELATED APPLICATIONS

The present application is a continuation-in-part of U.S. patent application Ser. No. 12/091,929, filed Apr. 28, 2008, which claims the benefit of International Application No. PCT/US06/42148, filed Oct. 30, 2006, and the benefit of U.S. Provisional Application No. 60/731,349, filed Oct. 28, 2005. The entire disclosure and teachings of the above-referenced Applications are incorporated herein by reference.

STATEMENT OF FEDERALLY SPONSORED RESEARCH AND DEVELOPMENT

This invention was made with government support under NIH Grant No. AI029471 awarded by the National Institutes of Health. The government has certain rights in the invention.

BACKGROUND OF THE INVENTION

Enteric fever caused by members of the genus *Salmonella*, including typhoid and paratyphoid fevers, continues to constitute a significant disease and mortality burden among populations in developing countries (Lancet 2005; 366:749-762) and represents a notable risk for travelers (Lancet Infect Dis. 2005; 5(10):623-628). Incidences of enteric fever caused by *Salmonella enterica* serovars Typhi and Paratyphi A (*S. Typhi* and *S. Paratyphi* A) are on the rise due to the emergence and spread of antibiotic resistant variants (Lancet Infect Dis. 2005 5(10):623-8). Although the clinical disease caused by *S. Paratyphi* A is overall somewhat milder than that due to *S. Typhi*, the former can nevertheless result in full-blown enteric fever with an assortment of complications and, if untreated or improperly treated, can result in death. A need exists for vaccines that are safe and effective in combating *Salmonella* infections.

SUMMARY OF THE INVENTION

The present invention is drawn to an attenuated *S. Paratyphi* A strain, preferably a live, attenuated *S. Paratyphi* A strain.

In one embodiment, the *S. Paratyphi* A strains of the present invention have at least one attenuating mutation selected from the group consisting of attenuating mutations in the guaBA loci, the guaB gene, the guaA gene, the clpP gene and the clpX gene. In preferred embodiments, the *S. Paratyphi* A strain has an attenuating mutation in the guaB gene, the guaA gene and the clpP gene. In another preferred embodiment, the *Salmonella Paratyphi* A strain has an attenuating mutation in the guaB gene, the guaA gene and the clpX gene. In a further preferred embodiment, the *Salmonella Paratyphi* A strain has an attenuating mutation in the guaB gene, the guaA gene, the clpP gene and the clpX gene.

In one embodiment the attenuating mutations of the guaBA loci, the guaB gene, the guaA gene, the clpP gene, and the clpX gene are attenuating mutations that reduce the level of expression the loci or the genes, or that block expression of the loci or the genes.

In another embodiment the attenuating mutations of the guaBA loci, the guaB gene, the guaA gene, the clpP gene, and the clpX gene are attenuating mutations that reduce the activity of a polypeptide encoded by the loci or the genes, or inactivates a polypeptide encoded by the loci or the genes.

In a preferred embodiment, the *Salmonella Paratyphi* A strain is the *S. Paratyphi* A 9150 strain.

The present invention also includes *S. Paratyphi* A strains that have at least one attenuating mutation selected from the group consisting of an attenuating mutation in the guaBA loci, the guaB gene, the guaA gene, the clpP gene and the clpX gene, and that further comprises a stabilized plasmid expression system.

In a preferred embodiment, the stabilized plasmid expression system comprises an expression vector having (a) a restricted-copy-number origin of replication cassette, (b) at least one post-segregational killing cassette, (c) at least one partitioning cassette, and (d) an expression cassette.

In preferred embodiments, the restricted-copy-number origin of replication cassette comprises (i) a nucleotide sequence encoding an origin of replication that limits the expression vector to an average plasmid copy number of about 2 to 75 copies per cell, (ii) a first unique restriction enzyme cleavage site located 5' of the nucleotide sequence encoding the origin of replication, and (iii) a second unique restriction enzyme cleavage site located 3' of the nucleotide sequence encoding the origin of replication.

In the same embodiments, the post-segregational killing cassette comprises (i) a nucleotide sequence encoding at least one post-segregational killing locus, (ii) a third unique restriction enzyme cleavage site located 5' of the nucleotide sequence encoding the post-segregational killing locus, and (iii) a fourth unique restriction enzyme cleavage site located 3' of the nucleotide sequence encoding the post-segregational killing locus.

In the same embodiments, the partitioning cassette comprises (i) a nucleotide sequence encoding at least one partitioning function, (ii) a fifth unique restriction enzyme cleavage site 5' of the nucleotide sequence encoding the partitioning function, and (iii) a sixth unique restriction enzyme cleavage site located 3' of the nucleotide sequence encoding the partitioning function.

In the same embodiments, the expression cassette comprises (i) a nucleotide sequence encoding a selected antigen operably linked to a promoter, (ii) a seventh unique restriction enzyme cleavage site located 5' of the nucleotide sequence encoding the selected antigen operably linked to a promoter, and (iii) an eighth unique restriction enzyme cleavage site located 3' of the nucleotide sequence encoding the selected antigen operably linked to a promoter.

In preferred embodiments, the nucleotide sequence encoding the origin of replication is a nucleotide sequence selected from the group consisting of the oriE1 sequence of SEQ ID NO:28, the ori101 sequence of SEQ ID NO:30, and the ori15A sequence of SEQ ID NO:29.

In preferred embodiments, the nucleotide sequence encoding the post-segregational killing locus is a nucleotide sequence selected from the group consisting of a nucleotide sequence encoding the ssb balanced-lethal system, a nucleotide sequence encoding the asd balanced-lethal system, a nucleotide sequence encoding the phd-doc proteic system, and a nucleotide sequence encoding the hok-sok antisense system. More preferably, the post-segregational killing locus is a nucleotide sequence encoding ssb balanced-lethal system selected from the group consisting of the *Shigella flexneri* ssb locus, the *Salmonella Typhi* ssb locus, and the *E. coli* ssb locus. Even more preferably, the ssb balanced-lethal system is a ssb locus comprising a ssb inducible promoter, a ssb constitutive promoter and a ssb coding region of *S. flexneri* 2a strain CVD 1208s set forth in SEQ ID NO:34.

In preferred embodiments, the nucleotide sequence encoding the partitioning function is a nucleotide sequence selected from the group consisting of the *E. coli* parA locus set forth in SEQ ID NO:31 and the *E. coli* pSC101 par locus set forth in SEQ ID NO:32.

In preferred embodiments, the promoter is an inducible promoter, more preferably an ompC promoter, even more preferably the ompC promoter set forth in SEQ ID NO:33.

In one embodiment, the nucleotide sequence encoding a selected antigen is a nucleotide sequence encoding a homologous antigen. In another embodiment, the nucleotide sequence encoding a selected antigen is a nucleotide sequence encoding a heterologous antigen.

In preferred embodiments, the nucleotide sequence encoding a selected antigen is a nucleotide sequence encoding a heterologous antigen selected from the group consisting of a viral antigen, a bacterial antigen, a cancer antigen, and an auto-immune antigen.

The present invention also includes a pharmaceutical formulation comprising one or more of the attenuated *Salmonella Paratyphi* A strains of the present invention. Preferably the pharmaceutical formulations are oral pharmaceutical formulations.

The present invention further includes a method of inducing an immune response in a subject, comprising administering an immunologically-effective amount of a pharmaceutical formulation of the present invention to a subject. Preferably, the immune response is a protective immune response.

The immunologically-effective amount of the pharmaceutical formulation contains about $10^2$ cfu to about $10^{10}$ cfu, more preferably about $10^6$ cfu to about $10^9$ cfu, of the attenuated *S. Paratyphi* A strain within the pharmaceutical formulation.

In one embodiment, the immune response is to *Salmonella Paratyphi* A. In another embodiment, the immune response is to the selected antigen. In a further embodiment, the immune response is to both *Salmonella Paratyphi* A and the selected antigen.

The Lambda Red-mediated mutagenesis system may be used to mutate or delete various chromosomal loci and genes from the *S. Paratyphi* strains of the present invention.

BRIEF DESCRIPTION OF THE DRAWINGS

FIG. 1 shows the PCR amplification products of guaBA and guaBA::cml. Lane 1 is wild-type guaBA; lanes 2 and 3 are guaBA::cml. Arrows indicate molecular weight marker bands of 3 kb (top) and 1.5 kb (bottom).

FIG. 2 shows the PCR amplification products of guaBA::cml and guaBA deletions. Lane 1 is guaBA::cml; lanes 2 to 5 are guaBA deletions. Arrows indicate molecular weight marker bands of 1.5 kb (top) and 0.5 kb (bottom).

FIG. 3 shows the results of a complementation study of the guaBA deletion. Plate 1 is the guaBA mutant transformed with pLowBlu 184; plate 2 is the same mutant transformed with pATGguaBA.

FIG. 4 shows the PCR amplification products of wt, clpX and clpX-guaBA attenuated *S. Paratyphi* A. Panel A shows PCR products produced using primers specific for clpX, whereas panel B shows PCR products produced using primers specific for guaBA. Arrows indicate molecular weight marker bands of 1.5 kb (top) and 0.5 kb (bottom) on panel A, and 3 kb (top) and 0.5 kb (bottom) on panel B.

FIG. 5 shows the PCR amplification products of wt, clpP and clpP-guaBA attenuated *S. Paratyphi* A. Panel A shows PCR products produced using primers specific for clpP, whereas panel B shows PCR products produced using primers specific for guaBA. Arrows indicate molecular weight marker bands of 1 kb (top) and 0.5 kb (bottom) on panel A, and 3 kb (top) and 0.5 kb (bottom) on panel B.

Figure 6:
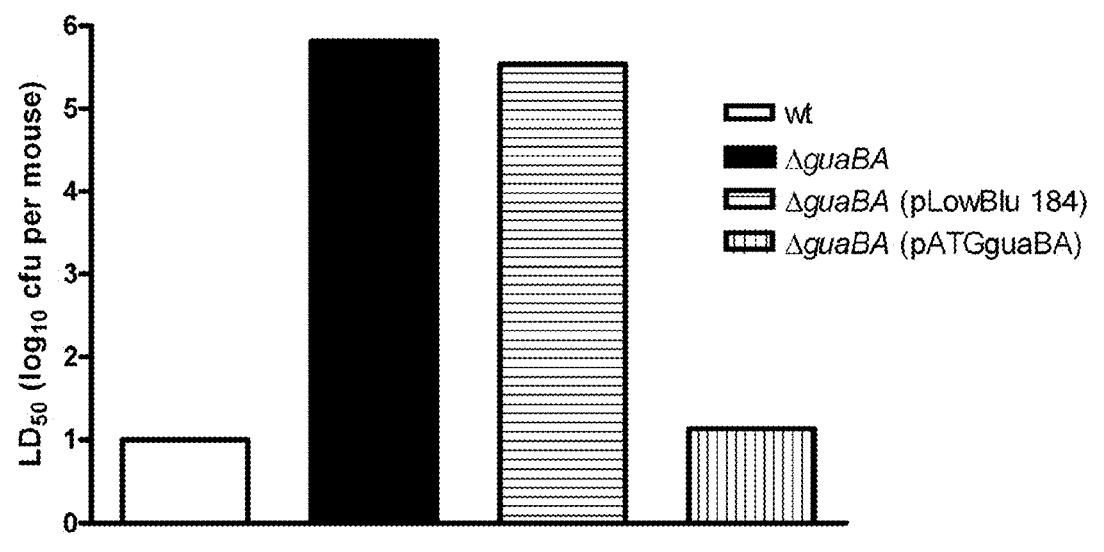

FIG. 6 is a graphical representation of data from $LD_{50}$ tests in mice injected with wt, guaBA-deleted *S. Paratyphi* A, guaBA-deleted complemented with pLowBlu 184, and guaBA-deleted complemented with pATGguaBA.

FIG. 7 is a graphical representation of data from $LD_{50}$ tests in mice injected with wt, clpX-deleted *S. Paratyphi* A, guaBA-deleted *S. Paratyphi* A, or clpX-guaBA-deleted *S. Paratyphi* A. The data include mice injected with clpX-deleted *S. Paratyphi* A complimented with pLowBlu 184 or pATGclpX, as well as clpX-guaBA-deleted *S. Paratyphi* A complimented with pLowBlu 184 or pATGclpXATGguaBA.

FIG. 8 is a graphical representation of data from $LD_{50}$ tests in mice injected with wt, clpP-deleted *S. Paratyphi* A, guaBA-deleted *S. Paratyphi* A, or clpP-guaBA-deleted *S. Paratyphi* A. The data include mice injected with clpP-deleted *S. Paratyphi* A complimented with pLowBlu 184 or pATGclpP, as well as clpP-guaBA-deleted *S. Paratyphi* A complimented with pLowBlu 184 or pATGclpPATGguaBA.

FIG. 9 shows hyper-flagellation by electron microscopy of mutations clpP in *S. Paratyphi* A.

FIG. 10 Alignment of chromosomal fliD-fliS loci from *Salmonella enterica* serovars Typhimurium, Enteritidis, Paratyphi A, and Typhi. FIGS. 10A-10D show the alignment of the chromosomal fliD-fliS loci as between *Salmonella Typhimurium* (SEQ ID NO:47), serovar Paratyphi A (using the shorthand "Typhi A") (SEQ ID NO:48) and serovar Typhi strain Ty2 (SEQ ID NO:49). FIGS. 10E-10H show the alignment of the chromosomal fliD-fliS loci as between *Salmonella Enteritidis* (SEQ ID NO:50) and *Salmonella Typhimurium* (SEQ ID NO:47).

DETAILED DESCRIPTION OF THE INVENTION

A. Attenuated *S. Paratyphi* A Strains

The present invention relates to an attenuated *S. Paratyphi* A strain. Such attenuated *S. Paratyphi* A strains may be used to induce an immune response in a subject without causing disease in the subject.

The *S. Paratyphi* A strain used as the starting material of the present invention may be any *S. Paratyphi* A strain and the identity of the strain is not critical. Preferred *S. Paratyphi* A strains include *S. Paratyphi* A 9150 strain.

The *S. Paratyphi* A strains of the present invention are attenuated. As used herein, attenuated strains of *S. Paratyphi* A are those that have a reduced, decreased, or suppressed ability to cause disease in a subject, or those completely lacking in the ability to cause disease in a subject. Attenuated strains may exhibit reduced or no expression of one or more genes, may express one or more proteins with reduced or no activity, may exhibit a reduced ability to grow and divide, or a combination of two or more of these characteristics. The attenuated strains of the present invention may be living or dead.

In addition to the attenuated *S. Paratyphi* A strains of the present invention, attenuated strains of other enteric pathogens (e.g., *Salmonella Typhi, Salmonella Paratyphi* B, *Shigella, Vibrio cholerae*), commensals (e.g., *Lactobacillus, Streptococcus gordonii*) and licensed vaccine strains (e.g., BCG) are also encompassed within the scope of the invention. These additional strains have all of the attenuating mutations of the *S. Paratyphi* A strains of the present invention, may be transformed with the stabilized plasmid expression system of the present invention, and may be used as an immunizing composition as described herein.

In preferred embodiments, the attenuated S. Paratyphi A strains of the present invention have a mutation in one or more of the guaBA loci, the guaB gene, the guaA gene, the clpP gene and the clpX gene of S. Paratyphi. For example, the attenuated S. Paratyphi A strains of the present invention may have a mutation (i) in the guaB gene and the clpP gene, (ii) in the guaA gene and the clpP gene, (iii) in the guaB gene, the guaA gene, and the clpP gene, (iv) in the guaBA loci and the clpP gene, (v) in the guaB gene and the clpX gene, (vi) in the guaA gene and the clpX gene, (vii) in the guaB gene, the guaA gene, and the clpX gene, (viii) in the guaBA loci and the clpX gene, (ix) in the guaB gene, the clpP gene and the clpX gene, (x) in the guaA gene, the clpP gene and the clpX gene, (xi) in the guaB gene, the guaA gene, the clpP gene and the clpX gene, or (xii) in the guaBA loci, the clpP gene and the clpX gene.

The mutations of the loci and genes described herein may be any mutation, such as one or more nucleic acid deletions, insertions or substitutions. The mutations may be any deletion, insertion or substitution of the loci or genes that results in a reduction or absence of expression from the loci or genes, or a reduction or absence of activity of a polypeptide encoded by the loci or genes. The mutations may be in the coding or non-coding regions of the loci or genes.

Preferably, in the present invention, the chromosomal genome of the S. Paratyphi A strain is modified by removing or otherwise modifying the guaBA loci, and thus blocking the de novo biosynthesis of guanine nucleotides. More preferably, a mutation in the guaBA loci inactivates the purine metabolic pathway enzymes IMP dehydrogenase (encoded by guaB) and GMP synthetase (encoded by guaA). As a consequence of these mutations, S. Paratyphi A are unable to de novo synthesize GMP, and consequently GDP and GTP nucleotides, which severely limits bacterial growth in mammalian tissues. In vitro, the AguaBA S. Paratyphi A mutants of the present invention are unable to grow in minimal medium unless supplemented with guanine. In tissue culture, the AguaBA S. Paratyphi A mutants of the present invention were found to show a significant reduction in their capability for invasion. AguaBA S. Paratyphi A mutants may scavenge guanine nucleotides from the tissues of the mammalian host. However, their assimilation into S. Paratyphi A requires prior dephosphorylation to nucleosides by periplasmic nucleotidases to be incorporated as nucleotide precursors into the guanine salvage pathway. Therefore, as nucleotides are readily available in the intracellular environment of the mammalian host, the attenuation due to the de novo synthesis of guanine nucleotides is due either to the inefficiency of the salvage pathway or to reasons that are obscure to today's knowledge.

The guaA gene of S. Paratyphi A 9150, which encodes GMP synthetase, is 1578 bp in size (SEQ ID NO:36), and is 98% homologous to the guaA gene of S. Typhi Ty2 as determined by NCBI BLAST nucleotide comparison. Deletion mutants can be produced by eliminating portions of the coding region of the guaA gene of S. Paratyphi A so that proper folding or activity of GuaA is prevented. For example, about 25 to about 1500 bp, about 75 to about 1400 bp, about 100 to about 1300 bp, or all of the coding region can be deleted. Alternatively, the deletion mutants can be produced by eliminating, for example, a 1 to 100 bp fragment of the guaA gene of S. Paratyphi A so that the proper reading frame of the gene is shifted. In the latter instance, a nonsense polypeptide may be produced or polypeptide synthesis may be aborted due to a frame-shift-induced stop codon. The preferred size of the deletion is about 75 to 750 bp. Deletions can also be made that extend beyond the guaA gene, i.e., deletions in the elements controlling translation of the guaA gene, such as in a ribosome binding site.

The guaB gene of S. Paratyphi A 9150, which encodes IMP dehydrogenase, is 1467 bp in size (SEQ ID NO:35), and is 98% homologous to the guaB gene of S. Typhi Ty2 as determined by NCBI BLAST nucleotide comparison. Deletion mutants can be produced by eliminating portions of the coding region of the guaB gene of S. Paratyphi A so that proper folding or activity of GuaB is prevented. For example, about 25 to about 1400 bp, about 75 to about 1300 bp, about 100 to about 1200 bp, or all of the coding region can be deleted. Alternatively, the deletion mutants can be produced by eliminating, for example, a 1 to 100 bp fragment of the guaB gene of S. Paratyphi A so that the proper reading frame of the gene is shifted. In the latter instance, a nonsense polypeptide may be produced or polypeptide synthesis may be aborted due to a frame-shift-induced stop codon. The preferred size of the deletion is about 75 to 750 bp. Deletions can also be made that extend beyond the guaB gene, i.e., deletions in the elements controlling transcription of the guaB gene, such as in a promoter.

The clpP gene of S. Paratyphi A 9150, which encodes a serine-protease, is 624 bp in size (SEQ ID NO:37), and 99% homologous to the clpP gene of S. Typhi Ty2 as determined by NCBI BLAST nucleotide comparison. Deletion mutants can be produced by eliminating portions of the coding region of the clpP gene of S. Paratyphi A so that proper folding or activity of ClpP is prevented. For example, about 25 to about 600 bp, about 75 to about 500 bp, about 100 to about 400 bp, or all of the coding region can be deleted. Alternatively, the deletion mutants can be produced by eliminating, for example, a 1 to 100 bp fragment of the clpP gene of S. Paratyphi A so that the proper reading frame of the gene is shifted. In the latter instance, a nonsense polypeptide may be produced or polypeptide synthesis may be aborted due to a frame-shift-induced stop codon. The preferred size of the deletion is about 25 to 600 bp. Deletions can also be made that extend beyond the clpP gene, i.e., deletions in the elements controlling transcription of the clpP gene, such as in a promoter.

The clpX gene of S. Paratyphi A 9150, which encodes a chaperone ATPase, is 1272 bp in size (SEQ ID NO:38), and 99% homologous to the clpX gene of S. Typhi Ty2 as determined by NCBI BLAST nucleotide comparison. Deletion mutants can be produced by eliminating portions of the coding region of the clpX gene of S. Paratyphi A so that proper folding or activity of ClpX is prevented. For example, about 25 to about 1200 bp, about 75 to about 1100 bp, about 100 to about 1000 bp, or all of the coding region can be deleted. Alternatively, the deletion mutants can be produced by eliminating, for example, a 1 to 100 bp fragment of the clpX gene of S. Paratyphi A so that the proper reading frame of the gene is shifted. In the latter instance, a nonsense polypeptide may be produced or polypeptide synthesis may be aborted due to a frame-shift-induced stop codon. The preferred size of the deletion is about 75 to 750 bp. Deletions can also be made that extend beyond the clpX gene, i.e., deletions in the elements controlling transcription of the clpX gene, such as in a promoter.

Deletions can be made in any of the loci or genes included herein by using convenient restriction sites located within the loci or genes, or by site-directed mutagenesis with oligonucleotides (Sambrook et al, In: Molecular Cloning, A Laboratory Manual, Eds., Cold Spring Harbor Publications (1989)).

Inactivation of the loci or genes can also be carried out by an insertion of foreign DNA using any convenient restriction site, or by site-directed mutagenesis with oligonucleotides (Sambrook et al, supra) so as to interrupt the correct transcription of the loci or genes. The typical size of an insertion that can inactivate the loci or genes is from 1 base pair to 100 kbp, although insertions smaller than 100 kbp are preferable. The insertion can be made anywhere inside the loci or gene coding regions or between the coding regions and the promoters.

Other methods for the inactivation of the loci and genes include the transfer into Salmonella of deletions or insertions made in other enterobacteriae guaBA loci, guaA, guaB, clpP or clpX genes, transposon-generated deletions, and imprecise excision of DNA insertions.

Preferably, the bacterial loci and genes are mutated using Lambda Red-mediated mutagenesis (Datsenko and Wanner, PNAS USA 97:6640-6645 (2000)). Briefly, in step 1 host bacteria targeted for mutation are transformed with a temperature sensitive plasmid encoding λ Red recombinase. These bacteria are grown in the presence of arabinose to induce λ Red production. Chromosomal mutagenesis of a target sequence is accomplished by electroporation of the host with linear DNA in which the target gene is replaced with an antibiotic resistance marker. This DNA also encodes short regions of flanking chromosomal sequences to allow for chromosomal integration of the resistance marker by λ Red-mediated homologous recombination. Recombinants are selected for on solid media containing the appropriate antibiotic, and incubated at a temperature facilitating the loss of the plasmid encoding λ Red recombinase. For step 2, removal of the chromosomal resistance marker is facilitated by transforming the bacteria with a temperature sensitive plasmid encoding FLP recombinase, which targets unique sequences within the antibiotic resistance marker now present in the host chromosome. Transformants are grown at temperatures permissive for the presence of the FLP recombinase which is expressed constitutively. Mutants are screened via PCR, grown at a temperature to facilitate loss of the plasmid encoding FLP recombinase, and selected for storage.

The attenuated S. Paratyphi A strains of the present invention may contain mutations in one or more additional genes. While an extensive discussion of additional attenuating mutations of Salmonella spp. is provide in U.S. Pat. No. 6,682,729, exemplary genes include those encoding various biochemical pathways, global regulatory systems, heat shock proteins, other regulatory genes, and putative virulence properties. Specific examples of such attenuating mutations include, but are not limited to: (i) auxotrophic mutations, such as aro, gua, nad, thy, and asd mutations; (ii) mutations that inactivate global regulatory functions, such as cya, crp, phoP/phoQ, phoP$^c$ and ompR mutations; (iii) mutations that modify the stress response, such as recA, htrA, htpR, hsp and groEL mutations; (iv) mutations in specific virulence factors, such as pag and prg (v) mutations that affect DNA topology, such as topA mutations; (vi) mutations that block biogenesis of surface polysaccharides, such as rib, galE and via mutations; (vii) mutations that modify suicide systems, such as sacB, nuc, hok, gef, kil, and phlA mutations; (viii) mutations that introduce suicide systems, such as lysogens encoded by P22, λ murein transglycosylase and S-gene; and (ix) mutations that disrupt or modify the correct cell cycle, such as minB mutations.

B. Stabilized Expression Plasmid System

The attenuated S. Paratyphi A strains of the present invention include those strains engineered to express selected polypeptides (antigens). Such attenuated S. Paratyphi A strains can be used to induce an immune response to S. Paratyphi itself, or to induce an immune response to the selected antigens expressed by the attenuated S. Paratyphi A strains, or both.

Such attenuated S. Paratyphi A strains are transformed with a stabilized expression plasmid system. The stabilized expression plasmid system encodes a selected antigen.

The stabilized expression plasmid system comprises expression vector that comprises a plasmid maintenance system (PMS) and a nucleotide sequence encoding a selected antigen.

The stabilized expression plasmid system optimizes the maintenance of the expression vector in the bacteria at two independent levels by: (1) removing sole dependence on balanced lethal maintenance systems; and (2) incorporating a plasmid partition system to prevent random segregation of expression vectors, thereby enhancing their inheritance and stability.

The PMS includes (a) an origin of replication, (b) at least one post-segregational killing function, and (c) at least one partitioning function. Each of the noted elements of the PMS may be an individual cassette of the stabilized expression plasmid system. Each of the cassettes may comprise unique restriction enzyme cleavage sites located at the 5' and 3' ends of the cassettes.

Preferred stabilized expression plasmid systems are those described in pending U.S. patent application Ser. No. 11/542, 264, which is incorporated by reference herein in its entirety.

1. Origin of Replication

The PMS includes a restricted-copy-number origin of replication that limits the expression vector to a range of plasmid copies per cell. Due to varying degrees of toxicity associated with different selected antigens (e.g., higher toxicity for antigens derived from parasitic organisms such Plasmodium falciparum versus virtually no toxicity for the fragment C of tetanus toxin), the stabilized expression plasmid system of the present invention is based on either a low or medium copy number expression vector (plasmid). It will be appreciated by one skilled in the art that the selection of an origin of replication will depend on the degree of toxicity, i.e., the copy number should go down as toxicity to the bacterial strain goes up.

It is preferable for the origin of replication to confer an average copy number which is between about 2 and about 75 copies per cell, between about 5 and about 60 copies per cell, between about 5 to about 30 copies per cell, or between about 5 to about 15 copies per cell. The origins of replication included herein are derived from the E. coli plasmid pAT153 (oriE1, ~60 copies per chromosomal equivalent), the E. coli plasmid pACYC184 (ori15A, ~15 copies per chromosomal equivalent), and the Salmonella typhimurium plasmid pSC101 (ori101, ~5 copies per chromosomal equivalent). The structural organization of the engineered origins of replication cassettes for pSC101, pACYC184, and pAT153 are analogous in structure and function.

The origins of replication of the present invention includes both naturally-occurring origins of replication, as well as origins of replication encoded by nucleotide sequences which are substantially homologous to nucleotide sequences encoding naturally-occurring origins of replication, and which retain the function exhibited by the naturally-occurring origins of replication.

In preferred embodiments, the nucleotide sequence encoding the origin of replication is a nucleotide sequence selected from the group consisting of the oriE1 sequence of SEQ ID NO:28, the ori101 sequence of SEQ ID NO:30, and the ori15A sequence of SEQ ID NO:29.

In a further preferred embodiment, the origin of replication is the oriE1 locus from pSC101, conferring a copy number of approximately 5 copies per genome equivalent, set forth in SEQ ID NO:28.

2. Partitioning Function

The PMS also includes a partitioning function, also known in the art and herein as a "segregating system" and a "partitioning system." The partitioning function is any plasmid stability-enhancing function that operates to increase the frequency of successful delivery of a plasmid to each newly divided bacterial cell, as compared to the frequency of delivery of a corresponding plasmid without such a function. Partitioning systems include, for example, equi-partitioning systems, pair-site partitioning systems, and the systems provided in Table 1 of Chapter 5, Partition Systems of Bacterial Plasmids. B. E. Funnell and R. A. Slavcev. In Plasmid Biology. 2004. B E Funnell and G J Phillips, eds. ASM Press, Washington, D.C.

The partitioning systems of the present invention includes both naturally-occurring partitioning systems, as well as partitioning systems encoded by nucleotide sequences which are substantially homologous to nucleotide sequences encoding naturally-occurring partitioning systems, and which retain the function exhibited by the naturally-occurring partitioning systems.

Exemplary partitioning functions include, without limitation, systems of pSC101, the F factor, the P1 prophage, and IncFII drug resistance plasmids.

In particular, the par passive partitioning locus can be used. The function of the par locus appears to be related to increasing plasmid supercoiling at the origin of replication, which is also the binding site for DNA gyrase. An exemplary par sequence is that of *E. coli*, set forth in SEQ ID NO:32 (Miller et al. Nucleotide sequence of the partition locus of *Escherichia coli* plasmid pSC101, Gene 24:309-15 (1983); GenBank accession no. X01654, nucleotides 4524-4890)).

The active partitioning panA locus may also be used. An exemplary panA locus sequence is set forth in SEQ ID NO:31.

3. Post-Segregational Killing Function

The PMS further includes at least one post-segregational killing (PSK) function. The PSK function is a function which results in the death of any newly divided bacterial cell which does not inherit the plasmid of interest, and specifically includes balanced-lethal systems such as asd or ssb, proteic systems such as phd-doc, and antisense systems such as hok-sok.

The PSK function of the present invention includes both naturally-occurring PSK functions, as well as PSK functions encoded by nucleotide sequences which are substantially homologous to nucleotide sequences encoding naturally-occurring PSK functions, and which retain the function exhibited by the naturally-occurring PSK functions.

In preferred embodiments, the PSK function is the ssb balanced lethal system. The single-stranded binding protein (SSB) from *S. Typhi* is used to trans-complement an otherwise lethal mutation introduced into the chromosomal ssb gene. The biochemistry and metabolic roles of the *E. coli* SSB protein have been extensively reviewed in Lohman et al., *Annual Reviews in Biochemistry* 63:527, 1994 and Chase et al., *Annual Reviews in Biochemistry* 55:103, 1986 (the disclosures of which are incorporated herein by reference).

In the *S. Paratyphi* A strains of the present invention comprising a stabilized expression plasmid system wherein the PSK function is the ssb balanced lethal system, the native ssb locus of the bacteria is inactivated. The native ssb locus may be inactivated by any means known in the art, such as a suicide vector comprising a temperature sensitive origin of replication or Lambda Red-mediated mutagenesis (Datsenko and Wanner, *PNAS USA* 97:6640-6645 (2000)). In a preferred aspect, Lambda Red-mediated mutagenesis is used to inactivate the ssb locus of the attenuated *S. Paratyphi* A strains of the present invention.

In another aspect of the invention, the PSK function is the ssb locus where both the inducible and the constitutive ssb gene promoters are used as the promoters of the ssb PSK function. In a preferred embodiment, the PSK function comprises a ssb inducible promoter, a ssb constitutive promoter and a ssb coding region. Preferably, the ssb locus is the ssb locus of any one of *Shigella flexneri, Salmonella Typhi* and *E. coli*. In one embodiment the ssb locus is the ssb locus of *S. flexneri* 2a strain CVD 1208s set forth in SEQ ID NO:34.

In a related aspect of the invention, mutated alleles such as ssb-1 (or any mutation functionally equivalent to this allele, such as W54S; Carlini et al. *Mol. Microbiol.* 10:1067-1075 (1993)) may be incorporated into the stabilized expression plasmid system to enhance higher copy number plasmids by over-expression of SSB1-like proteins to form the required biologically active tetramers of SSB.

In a further embodiment, the PMS comprises two PSK functions.

4. Selected Antigen

The stabilized expression plasmid system also comprises a polynucleotide encoding selected antigen under control of a promoter.

The promoter is preferably an environmentally regulatable promoter, controlled by a biologically relevant signal such as osmolarity. In a preferred embodiment, the promoter is the ompC promoter. The ompC gene encodes a porin protein which inserts as a trimer into the outer membrane of a bacterial cell. Expression and control of ompC has been reviewed in considerable detail in Pratt et al., *Molecular Microbiology* 20:911, 1996 and Egger et al., *Genes to Cells* 2:167, 1997. In a preferred embodiment the ompC promoter fragment from *E. coli* is set forth in SEQ ID NO:33. See U.S. Pat. No. 6,703,233, which is incorporated herein by reference in its entirety. Transcription of this cassette may be terminated in the 3'-distal region by a trpA transcriptional terminator.

In one aspect, the inducible promoter is the mutated $P_{ompC1}$, or the $P_{ompC3}$ promoter. The promoter may be used to exclusively control the transcription of the downstream selected antigen.

The invention encompasses the expression of any antigen which does not destroy the attenuated *S. Paratyphi* A strain expressing it, and which elicits an immune response when the attenuated *S. Paratyphi* A strain expressing the antigen is administered to the subject. The selected antigens may be homologous (from *S. Paratyphi* A) or heterologous.

Non-limiting examples of the selected antigen include: Shiga toxin 1 (Stx1) antigen, Shiga toxin 2 (Stx2) antigen, hepatitis B, *Haemophilus influenzae* type b, hepatitis A, acellular pertussis ($_{ac}$P), varicella, rotavirus, *Streptococcus pneumoniae* (pneumococcal), and *Neisseria meningitidis* (meningococcal). See Ellis et al., *Advances in Pharm.*, 39: 393423, 1997 (incorporated herein by reference). Where the antigen is a Shiga toxin 2 antigen, the Shiga toxin 2 antigen can, for example, be either a B subunit pentamer or a genetically detoxified Stx 2. Further antigens of relevance to biodefense include: 1) one or more domains of the anthrax toxin Protective Antigen PA83 moiety, including but not limited to domain 4 (the eukaryotic cell-binding domain; D4), the processed 63 kDa biologically active form of PA83, or fulllength PA83; and 2) *Clostridium botulinum* antigens comprising the eukaryotic cell-binding heavy chain fragment of any neurotoxin serotype A, B, C, D, E, F, or G, in any combination. Other selected antigens include each of those disclosed in U.S. Pat. No. 6,190,669, incorporated herein by reference.

In one aspect, the selected antigen is an antigen that induced an immune response to cancer. In another aspect, the selected antigen is designed to provoke an immune response to autoantigens, B cell receptors and/or T cell receptors which are implicated in autoimmune or immunological diseases. For example, where inappropriate immune responses are raised against body tissues or environmental antigens, the immunizing compositions of the present invention may be used to induce an immune response to the autoantigens, B cell receptors and/or T cell receptors to modulate the responses and ameliorate the diseases. For example, such techniques can be efficacious in treating myasthenia gravis, lupus erythematosis, rheumatoid arthritis, multiple sclerosis, allergies and asthma.

In another aspect of the present invention, the stabilized expression plasmid system may include a polynucleotide encoding a selectable marker, or a temperature sensitive marker, such as drug resistance marker. A non-limiting example of a drug resistance marker includes aph which is known in the art to confer resistance to aminoglycosides kanamycin and/or neomycin.

The term "substantially homologous" or "substantial homologue," in reference to a nucleotide sequence or amino acid sequence herein, indicates that the nucleic acid sequence or amino acid sequence has sufficient homology as compared to a reference sequence (e.g., a native or naturally-occurring sequence) to permit the sequence to perform the same basic function as the corresponding reference sequence; a substantially homologous sequence is typically at least about 70 percent sequentially identical as compared to the reference sequence, typically at least about 85 percent sequentially identical, preferably at least about 90 or 95 percent sequentially identical, and most preferably about 96, 97, 98 or 99 percent sequentially identical, as compared to the reference sequence. It will be appreciated that throughout the specification, where reference is made to specific nucleotide sequences and/or amino acid sequences, that such nucleotide sequences and/or amino acid sequences may be replaced by substantially homologous sequences.

C. Methods of Inducing an Immune Response

The present invention also includes methods of inducing an immune response in a subject. The immune response may be to the attenuated *S. Paratyphi* A strain itself, a selected antigen expressed by an attenuated *S. Paratyphi* A strain transformed with a stabilized expression plasmid system, or both.

In one embodiment, the method of inducing an immune response comprises administering one or more of the strains of the present invention to a subject in an amount sufficient to induce an immune response in the subject. As used herein, the strain of the present invention includes both untransformed and transformed attenuated *S. Paratyphi* A strains.

In a further embodiment, the method of inducing an immune response comprises administering a pharmaceutical formulation comprising one or more of the strains of the present invention to a subject in an amount sufficient to induce an immune response in the subject (an immunologically-effective amount).

For the sake of convenience, the strains of the present invention and pharmaceutical formulations comprising the strains are referred to herein as "immunizing compositions." The skilled artisan will appreciate that the immunizing compositions are synonymous with vaccines.

As used herein, an "immune response" is the physiological response of the subject's immune system to the immunizing composition. An immune response may include an innate immune response, an adaptive immune response, or both.

In a preferred embodiment of the present invention, the immune response is a protective immune response. A protective immune response confers immunological cellular memory upon the subject, with the effect that a secondary exposure to the same or a similar antigen is characterized by one or more of the following characteristics: shorter lag phase than the lag phase resulting from exposure to the selected antigen in the absence of prior exposure to the immunizing composition; production of antibody which continues for a longer period than production of antibody resulting from exposure to the selected antigen in the absence of prior exposure to the immunizing composition; a change in the type and quality of antibody produced in comparison to the type and quality of antibody produced upon exposure to the selected antigen in the absence of prior exposure to the immunizing composition; a shift in class response, with IgG antibodies appearing in higher concentrations and with greater persistence than IgM, than occurs in response to exposure to the selected antigen in the absence of prior exposure to the immunizing composition; an increased average affinity (binding constant) of the antibodies for the antigen in comparison with the average affinity of antibodies for the antigen resulting from exposure to the selected antigen in the absence of prior exposure to the immunizing composition; and/or other characteristics known in the art to characterize a secondary immune response.

The subject to which the immunizing compositions may be administered is preferably a human, but may also be another mammal such as a simian, dog, cat, horse, cow or pig, or a bird, such as a chicken.

In one embodiment, the subject is a subject at risk for developing an *S. Paratyphi* A infection. In another embodiment, the subject is immunologically naïve or, alternatively, exhibits pre-existing immunity to *S. Typhi* infection or *S. Paratyphi* A infection.

In a further embodiment, the subject to which the strains of the present invention are administered develops a protective immune response against paratyphoid fever.

D. Formulations, Dosages, and Modes of Administration

The attenuated strains of the present invention, both those untransformed and transformed with a stabilized expression plasmid system, may be administered to a subject to induce an immune response. In a preferred embodiment, the strains of the present invention are administered in a pharmaceutical formulation.

The pharmaceutical formulations of the present invention may include pharmaceutically acceptable carriers, excipients, other ingredients, such as adjuvants. Pharmaceutically acceptable carriers, excipients, other ingredients are those compounds, solutions, substances or materials that are compatible with the strains of the present invention and are not unduly deleterious to the recipient thereof. In particular, carriers, excipients, other ingredients of the present invention are those useful in preparing a pharmaceutical formulation that is generally safe, non-toxic and neither biologically nor otherwise undesirable, and that may present pharmacologically favorable profiles, and includes carriers, excipients, other ingredients that are acceptable for veterinary use as well as human pharmaceutical use.

Suitable pharmaceutically acceptable carriers and excipients are well known in art and can be determined by those of skill in the art as the clinical situation warrants. The skilled artisan will understand that diluents are included within the scope of the terms carriers and excipients. Examples of suitable carriers and excipients include saline, buffered saline, dextrose, water, glycerol, ethanol, more particularly: (1) Dulbecco's phosphate buffered saline, pH about 7.4, containing about 1 mg/ml to 25 mg/ml human serum albumin, (2) 0.9% saline (0.9% w/v NaCl), (3) 5% (w/v) dextrose, and (4) water.

The mode of administration of the immunizing compositions of the present invention may be any suitable delivery means and/or methods that results in the induction of an immune response in the subject. Delivery means may include, without limitation, parenteral administration methods, such as subcutaneous (SC) injection, intravenous (IV) injection, transdermal, intramuscular (IM), intradermal (ID), as well as non-parenteral, e.g., oral, nasal, intravaginal, pulmonary (inhalation), ophthalmic, rectal administration, or by any other mode that results in the immunogenic composition contacting mucosal tissues. Preferably, administration is orally.

In one embodiment of the present invention, the immunizing compositions exists as an atomized dispersion for delivery by inhalation. Various liquid and powder formulations can be prepared by conventional methods for inhalation into the lungs of the subject to be treated. The atomized dispersion of the immunizing compositions typically contains carriers common for atomized or aerosolized dispersions, such as buffered saline and/or other compounds well known to those of skill in the art. The delivery of the immunogenic compositions via inhalation has the effect of rapidly dispersing the immunizing compositions to a large area of mucosal tissues as well as quick absorption by the blood for circulation of the immunizing compositions.

Additionally, immunizing compositions also exist in a liquid form. The liquid can be for oral dosage, for ophthalmic or nasal dosage as drops, or for use as an enema or douche. When the immunizing composition is formulated as a liquid, the liquid can be either a solution or a suspension of the immunizing composition. There are a variety of suitable formulations for the solution or suspension of the immunizing composition that are well know to those of skill in the art, depending on the intended use thereof. Liquid formulations for oral administration prepared in water or other aqueous vehicles may contain various suspending agents such as methylcellulose, alginates, tragacanth, pectin, kelgin, carrageenan, acacia, polyvinylpyrrolidone, and polyvinyl alcohol. The liquid formulations may also include solutions, emulsions, syrups and elixirs containing, together with the immunizing compositions, wetting agents, sweeteners, and coloring and flavoring agents.

Delivery of the described immunizing compositions in liquid form via oral dosage exposes the mucosa of the gastrointestinal and urogenital tracts to the immunizing compositions. A suitable dose, stabilized to resist the pH extremes of the stomach, delivers the immunizing composition to all parts of the gastrointestinal tract, especially the upper portions thereof. Any methods of stabilizing the immunizing composition in a liquid oral dosage such that the effective delivery of the composition is distributed along the gastrointestinal tract are contemplated for use with the immunizing compositions described herein, including capsules and a resuspended buffer solution to protect the attenuated bacteria against the acidic pH. The particular pharmaceutically acceptable carriers or diluents employed are not critical to the present invention, and are conventional in the art. Examples of diluents include: buffers for buffering against gastric acid in the stomach, such as citrate buffer (pH 7.0) containing sucrose, bicarbonate buffer (pH 7.0) alone or bicarbonate buffer (pH 7.0) containing ascorbic acid, lactose, and optionally aspartame (Levine et al, Lancet, 11:467-470 (1988)). Examples of carriers include: proteins, e.g., as found in skim milk; sugars, e.g., sucrose; or polyvinylpyrrolidone.

Delivery of the described immunizing compositions in liquid form via ophthalmic drops exposes the mucosa of the eyes and associated tissues to the immunizing compositions. A typical liquid carrier for eye drops is buffered and contains other compounds well known and easily identifiable to those of skill in the art.

Delivery of the described immunizing compositions in liquid form via nasal drops or aerosol exposes the mucosa of the nose and sinuses and associated tissues to the immunizing compositions. Liquid carriers for nasal drops are typically various forms of buffered saline.

Injectable formulations of the immunizing compositions may contain various carriers such as vegetable oils, dimethylacetamide, dimethylformamide, ethyl lactate, ethyl carbonate, isopropyl myristate, ethanol, polyols (glycerol, propylene glycol, and liquid polyethylene glycol) and the like. Physiologically acceptable excipients may include, for example, 5% dextrose, 0.9% saline, Ringer's solution or other suitable excipients. Intramuscular preparations can be dissolved and administered in a pharmaceutical excipient such as Water-for-Injection, 0.9% saline, or 5% glucose solution.

The attenuated *S. Paratyphi* A strains of the present invention may be administered to a subject in conjunction with other suitable pharmacologically or physiologically active agents, e.g., antigenic and/or other biologically active substances.

The attenuated *S. Paratyphi* A strains comprising a stabilized expression plasmid system may be administered to a subject prior to, concurrent with, or after expression of the selected antigen has begun. For example, the attenuated *S. Paratyphi* A strain comprising a stabilized expression plasmid system may be cultured for a period of time prior to administration to a subject to enable the bacterial to produce sufficient amounts of the selected antigen, such that an immune response will be raised to the selected antigen upon administration of the bacteria.

The amount and rate of administration of the immunizing compositions of the present invention may be readily determined by those of ordinary skill in the art without undue experimentation, such as by use of conventional antibody titer determination techniques and conventional bioefficacy/biocompatibility protocols. The amount and rate of administration will vary based on factors such as the weight and health of the subject, the identity of the bacteria being administered to the subject, the identity of the polypeptide being expressed in those stains engineered to express a selected antigen, the desired therapeutic effect, the desired time span of bioactivity, and the mode of administration of the immunizing composition.

In general, the amount of an immunizing composition administered to a subject is an amount sufficient to induce an immune response in the subject to a *S. Paratyphi* A strain or to the selected antigen being expressed by the *S. Paratyphi* A strain (an immunologically-effective amount). Preferably, the immune response is a protective immune response.

Generally, the dosage employed will contain about $10^2$ cfu to $10^{10}$ cfu of the *S. Paratyphi* A strain, preferably about $10^2$ cfu to $10^7$ cfu, or about $10^6$ cfu to $10^9$ cfu. Formulations for oral administration comprise about $10^2$ cfu to $10^{10}$ cfu of the *S. Paratyphi* A strain, preferably about $10^6$ cfu to $10^9$ cfu, and the formulation is in a capsule or resuspended in a buffer solution to protect the attenuated bacteria against the acidic pH in the stomach. Formulations for nasal administration comprise about $10^2$ cfu to $10^{10}$ cfu of the *S. Paratyphi* A strain, preferably about $10^2$ cfu to $10^7$ cfu, and is used for intranasal administration in which the bacteria is given in drops or in aerosol.

The immunizing compositions may be administered in a single dose, or in multiple doses over prolonged periods of time. In particular, the immunizing compositions may be administered over a period of one week, two weeks, three weeks, one month, six weeks, two months, ten weeks, three months, four months, six months, one year, or for extended periods longer than one year.

The immunizing compositions may be provided in dosage unit for uniform dosage and ease of administration. Each dosage unit form contains a predetermined quantity of the strains of the present invention calculated to produce a desired immune response, in association with a pharmaceutically acceptable carrier, excipient, or other ingredient.

The present invention also includes a kit comprising one or more of the immunizing compositions of the present invention, and optionally means for administering the compositions, and instructions for administering the compositions.

E. Examples

1. Bacterial Strains and Culturing Conditions

*Escherichia coli* strain DH5 alpha was used for all plasmid constructions. Live attenuated *S. Typhi* strain CVD 908-htrA harbors deletion mutations in aroC and aroD, interrupting the aromatic compound biosynthesis pathway, and htrA, which encodes a stress response protein (see Infect Immun. 60:2 (1992), pp. 536-541 and J. Biotechnol. 44:1-3 (1996), pp. 193-196). *S. Paratyphi* A 9150 lot # 11848 was purchased from the American Type Culture Collection (Manassas, Va.), and stored as CV 223 and CV 224. CV 223 was used in all experiments.

*E. coli* DH5 alpha was grown using Luria Bertani (LB) liquid medium or agar (Difco, Detroit, Mich.) supplemented with antibiotics carbenicillin (carb; 50 μg/ml), kanamycin (kan; 50 μg/ml) or chloramphenicol (cml; 25 μg/ml), where necessary. CVD 908-htrA and *S. Paratyphi* A 9150 and its derivatives were grown with 2× soy medium (20 g Hy-soy peptone, 10 g Hy-soy yeast extract, 3 g NaCl, ±15 g of granulated agar (Difco) per liter) with guanine (0.001% v/v) and antibiotics added where necessary. Liquid cultures were incubated at 30° C. or 37° C. at 250 rpm for 16-24 hrs unless stated otherwise.

Modified minimal medium (MMM) used for complementation analysis was composed of M9 salts (K2HPO4, 7 g/l; KH2PO4, 3 g/l; (NH4)2SO4, 1 g/l (pH7.5)), 0.5% (w/v) casamino acids (Difco), 0.5% (w/v) glucose, 0.01% (w/v) MgSO4.7H2O, 15 g of granulated agar (Difco) per liter and 1 μg/ml vitamin B1.

2. Plasmids and Molecular Genetic Techniques

Standard techniques were used for the construction of the plasmids represented here (see, for example, Sambrook et al., 1989 which is herein incorporated by reference in its entirety). Plasmid extraction and gel purification of DNA fragments were performed using QIAprep Spin Miniprep and QIAquick Gel Extraction kits, respectively, as directed by the manufacturer (Qiagen Inc., Valencia, Calif.). Plasmids pCR-Blunt II-TOPO (Invitrogen, Carlsbad, Calif.), pGEM®-T or pGEM®-T Easy (Promega, Madison, Wis.) were used as intermediates for cloning blunt ended polymerase chain reaction (PCR) products generated with Vent™ DNA Polymerase (New England Biolabs, Ipswich, Mass.). Plasmid pLowBlu 184 (E. M. Barry, unpublished data; CVD, University of Maryland, Baltimore) is a low copy number plasmid based on pACYC184 (ATCC) but containing the lactose operon sequence from pGEM®-5Zf(+) (2767-273 bp; Promega, Madison, Wis.) in place of the tetracycline resistance gene between AvaI and HindIII. Taq-Pro™ DNA Polymerase (Denville Sci., Metuchen, N.J.) was used for lambda Red-mediated mutagenesis, and for diagnostic PCR using 5 ul of a single bacterial colony diluted in 20 μl of sterile water. Taq-Pro™ DNA Polymerase was also used to add to pre-treat PCR fragments generated by Vent™ DNA Polymerase prior to cloning into pGEM®-T or pGEM®-T Easy. All restriction enzymes were purchased from New England Biolabs. T4 DNA polymerase (NEB) was used to create blunt ended DNA fragments. Electroporation of strains was performed in a Gene Pulser apparatus (Bio-Rad) set at 2.5 kV, 200Ω, and 25 μF. Molecular weight markers used in DNA gel electrophoresis are O'GeneRuler™ 1 kb DNA Ladder, ready-to-use (#SM1163, Fermentas, Hanover, Md.).

3. Lambda Red-Mediated Mutagenesis

This technique was performed as described by Datsenko and Wanner (Proc Natl Acad Sci USA. 2000 Jun. 6; 97(12): 6640-50), with certain modifications. Briefly, 10 colonies of bacteria carrying Red helper plasmid pKD46 (reader is directed to the Datsenko and Wanner reference for more information about this plasmid) were added to 20 ml of 2× soy media supplemented with carbenicillin and L-arabinose (0.2%) and grown at 30° C., 250 rpm for 3 hrs (OD 600 nm of ~0.6). Bacteria were made electrocompetent by washing 3 times with cold sterile water and concentrating 100 fold. Competent cells were electroporated with 100 ηg-1 μg of gel-purified PCR product. Following electroporation, bacteria were repaired using 2× soy medium with or without guanine. Cells were incubated in 2× soy media at 37° C. for 3 hrs prior to plating on 2× soy agar containing guanine and cml overnight. Antibiotic resistant colonies were selected and screened via PCR for alterations in the chromosomal regions of interest. Positive colonies were re-streaked onto 2× soy media containing cml, but lacking carbenicillin, to ensure loss of pKD46. Removal of the cml resistance cassette was performed as described by Datsenko and Wanner and involved using pCP20. Colonies exhibiting the desired genotype were re-streaked on 2× soy media lacking antibiotics to ensure the loss of the antibiotic resistance phenotype. Those selected for storage were re-screened via PCR prior to freezing at −70° C. in 2× soy media containing 20% (v/v) glycerol.

4. Agglutination

*S. Paratyphi* A strains were tested with commercially available sera (Difco™ *Salmonella* O Antiserum Group A, Becton Dickson, Sparks, Md., lot # 4092221). Briefly, a small inoculum of bacteria taken from a fresh plate was emulsified in 20 μl of PBS on a glass slide. 5 μl of antisera was added, and the slide agitated gently until agglutination was observed. *S. flexneri* vaccine strain CVD 1208 (J Infect Dis. 2004 Nov. 15; 190(10):1745-54) or *E. coli* DH5 alpha served as negative control bacteria.

5. Assessment of Virulence by Intraperitoneal Inoculation of Mice

Salmonella virulence was assessed as described previously in Infect Immun. 2001 August; 69(8):4734-41. Briefly, female BALB/c mice (Charles River Breeding Laboratories, Inc., Wilmington, Mass.) aged 6 to 8 weeks (three mice per group, three groups per vaccine strain) were injected intraperitoneally (i.p.) with various 10-fold dilutions of the bacteria (grown in the presence of guanine and antibiotics where necessary, and resuspended in phosphate-buffered saline PBS) mixed with 10% (wt/vol) hog gastric mucin (Difco, lot #4092018) in a final volume of 0.5 ml. Mice were monitored for extreme moribundity (close to death) or death every 24 hr for 72 h after inoculation. The 50% lethal dose (LD50) for each group of mice was calculated by linear regression analysis.

6. Construction of a Deletion in guaBA.

The sequencing of the S. Paratyphi A genome was incomplete at the commencement of this project. Hence, all oligonucleotides primers and subsequent DNA templates for Lambda Red-mediated mutagenesis were constructed based on the annotated S. Typhi Ty2 genome sequence (Genbank accession number NC_004631, Dec. 16, 2004 version). Sequence comparison of the regions mutated in S. Paratyphi A with those of S. Typhi revealed greater than 99% DNA sequence identity.

The genes which encode inosine-5'-monophosphate dehydrogenase (guaB) and guanosine monophosphate synthetase (guaA) form an operon and are located at 414059 to 417178 bp on the S. Typhi Ty2 genome (SEQ ID NO:26; see also U.S. Pat. No. 6,190,669 for detailed information with regard to the guaBA loci). Primers CVOL 13 and CVOL 15 (Table 1) bind to sequences outside the region designated for mutation. Primers CVOL 28 and CVOL 32 were designed to bind to regions of the Lambda Red template plasmid pKD3. The resulting PCR product encoded a cml resistance cartridge flanked on either side by a 100 bp of sequence homologous to guaBA at positions 413846 to 413945 (CVOL 28) and 417109 to 417010 (CVOL 32) on the *S. Typhi* Ty2 genome, respectively.

TABLE 1

| Name | Sequence[a] | SEQ ID NO: | Target | Region[b] |
|---|---|---|---|---|
| CVOL 13 | CTGCAGTCATTCCCACTCAATGGTAGC | 4 | Ty2 | 417176-417158 |
| CVOL 15 | GGAACATCGCACAGCGCA | 5 | Ty2 | 413715-413732 |
| CVOL 26 | GTGTAGGAGCTGCTTCG | 6 | pKD3 | 31-50 |
| CVOL 27 | CATATGAATATCCTCCTTAG | 7 | pKD3 | 1044-1025 |
| CVOL 28 | CGAACCGTCTGGTTAAGGCGGCTTACGGTAAAAATTGAGGAAGTTTGAGAGGATAACATGTGAGCGGGATCAAATTCTAAATCAGCAGGTTATTCAATCGTGTAGGCTGGAGCTGCTTC | 8 | pKD3 | 31-50 |
| CVOL 32 | TTCATTGATGATGCGGTTGGAAACACGACCCAGGAAGTCATACGGCAGGTGCGCCCAGTGCGCGGTCATAAAGTCGATGGTTTCGACAGCACGCAGAGAGCATATGAATATCCTCCTTAG | 9 | pKD3 | 1044-1025 |
| CVOL 41 | GAAGGAGTATTGCCCATGCTACGTATCG | 10 | Ty2 | 414057-414077 |
| CVOL 64 | CATATGAAGGAGTATTGCCCATGCTACGTATCGCTAAAGAAG | 11 | Ty2 | 414057-414086 |
| CVOL 65 | ATGCATCTGCAGTCATTCCCACTCAATGGTAGCCGG | 12 | Ty2 | 417176-417155 |
| CVOL 85 | ACAGATAAACGCAAAGATGGCTCGGGCAAA | 13 | Ty2 | 2484865-2484836 |
| CVOL 86 | TTATTCGCCAGAAGCCTGCGCTTCCGGTTT | 14 | Ty2 | 2483597-2483626 |
| CVOL 87 | CCTGAGAATGGCATTTGCGTCGTCGTGTGC | 15 | Ty2 | 2484929-2484900 |
| CVOL 88 | ACGGCGTGTTTACAGGAAAAACGAAAGGGG | 16 | Ty2 | 2483520-2483549 |
| CVOL 89 | TCATACAGCGGAGAACGAGATAATTTGGCC | 17 | Ty2 | 2485740-2485711 |
| CVOL 90 | TTACATAAGTAAGTCACTGGGAGGCGCGCT | 18 | Ty2 | 2485027-2485056 |
| CVOL 91 | TCCATCAGGTTACAATCAGTACAGCAGATT | 19 | Ty2 | 2485800-2485771 |
| CVOL 92 | TCATTAGTATATACACAAAATCATTCGAGC | 20 | Ty2 | 2484961-2484990 |
| CVOL 122 | GCGGCCGCGAAGGAGAGACGGAAATGTCATACAGCGGAGAACGAG | 21 | Ty2 | 2485752-2485722 |
| CVOL 123 | TCGCGAGAATTCTTACATAAGTAAGTCACTGGGAGGCGCGCT | 22 | Ty2 | 2485024-2485056 |
| CVOL 124 | GCGGCCGCGAAGGAGTTTGACTCATGACAGATAAACGCAAAGATG | 23 | Ty2 | 2484876-2484847 |
| CVOL 125 | CATATGTTATTCGCCAGAAGCCTGCGCTTCCGGTTT | 24 | Ty2 | 2483597-2483626 |

TABLE 1-continued

| Name | Sequence[a] | SEQ ID NO: | Target | Region[b] |
|------|-------------|------------|--------|-----------|
| CVOL 128 | <u>GCGGCCGC</u>TTACATAAGTAAGT CACTGGGAGGCGCGCT | 25 | Ty2 | 2485024-2485056 |

[a]Primers are listed in 5' > 3' direction with restriction enzyme cleavage sites underlined.
[b]Indicates region of homology to *S. Typhi* Ty2 genome (genbank accession number NC_004631) or plasmid pKD3 (genbank accession number AY048742).

Figure 2:
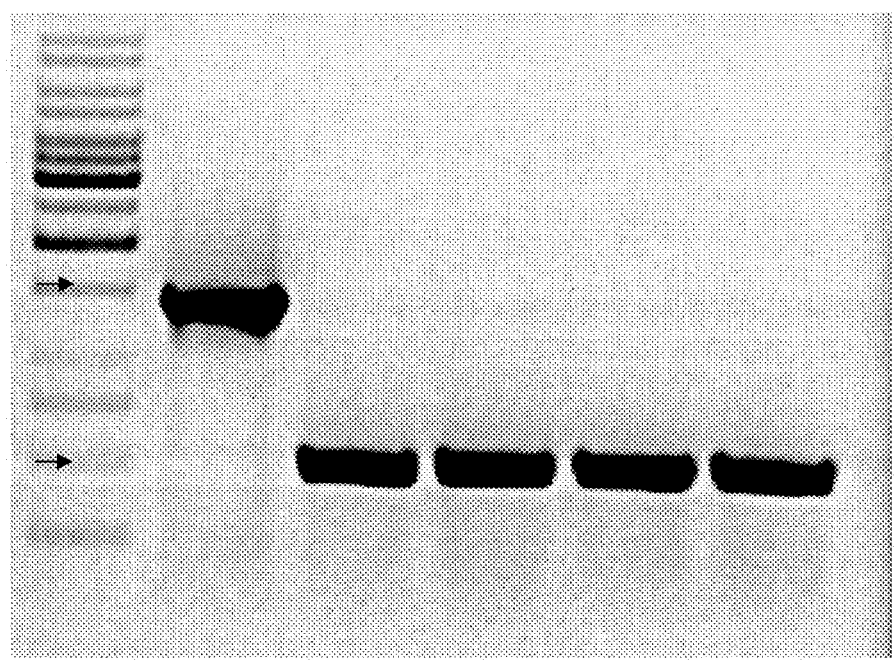
Figure 3:
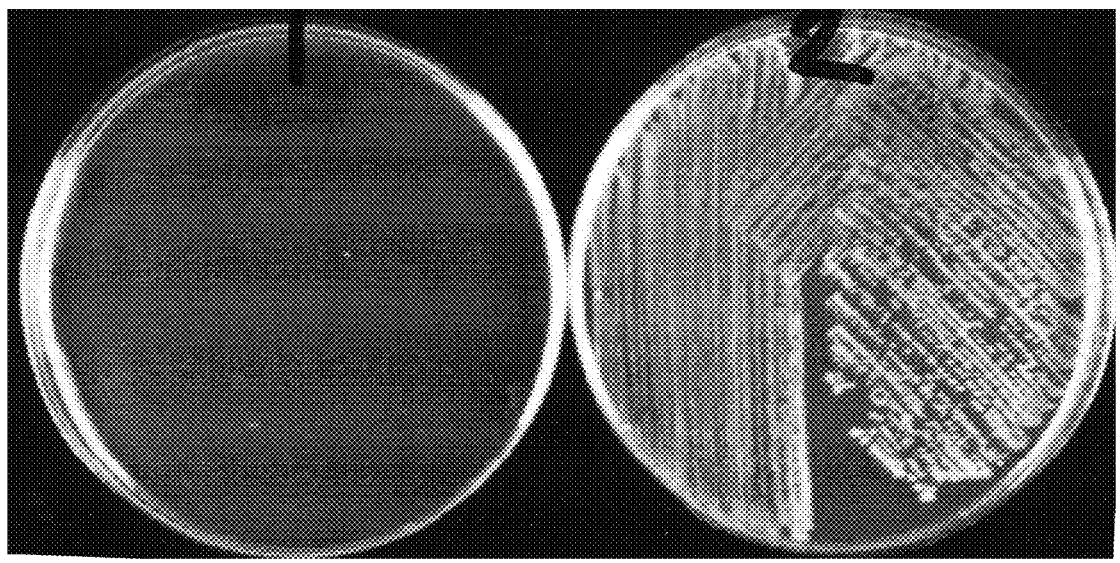
Figure 4:
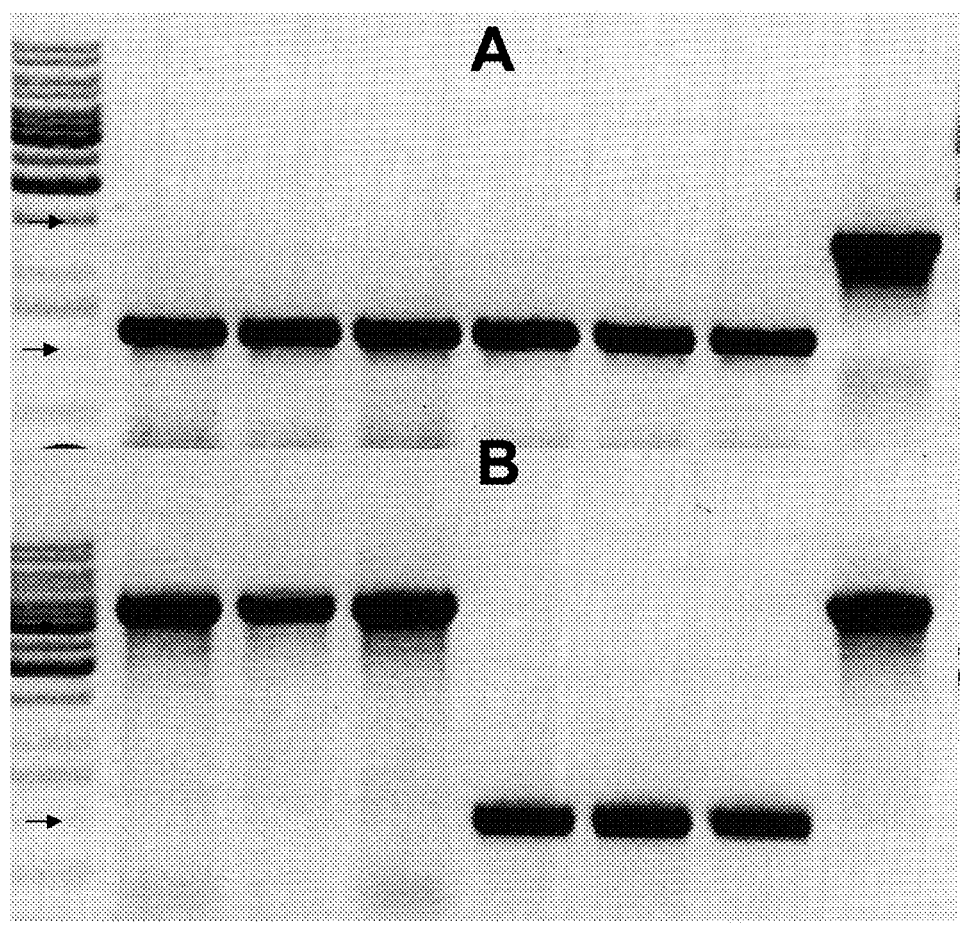
Figure 5:
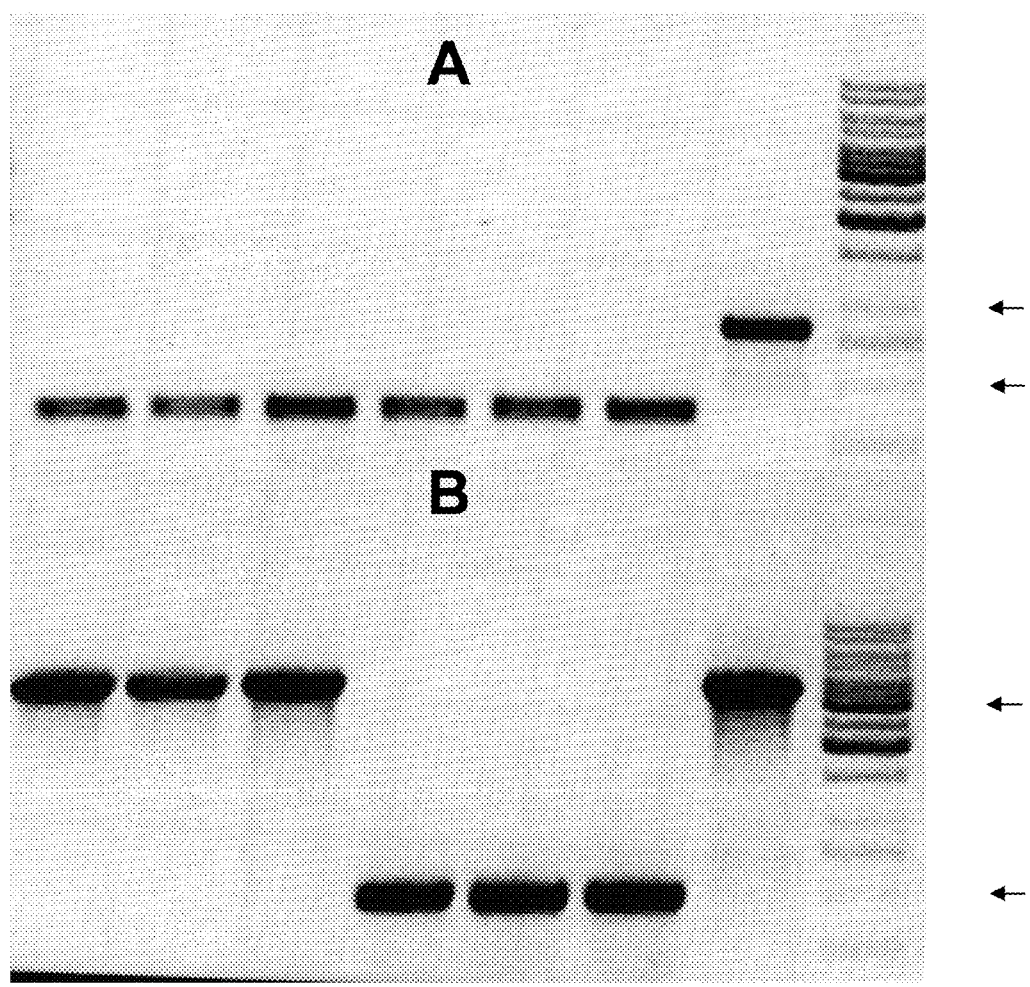
Figure 7:
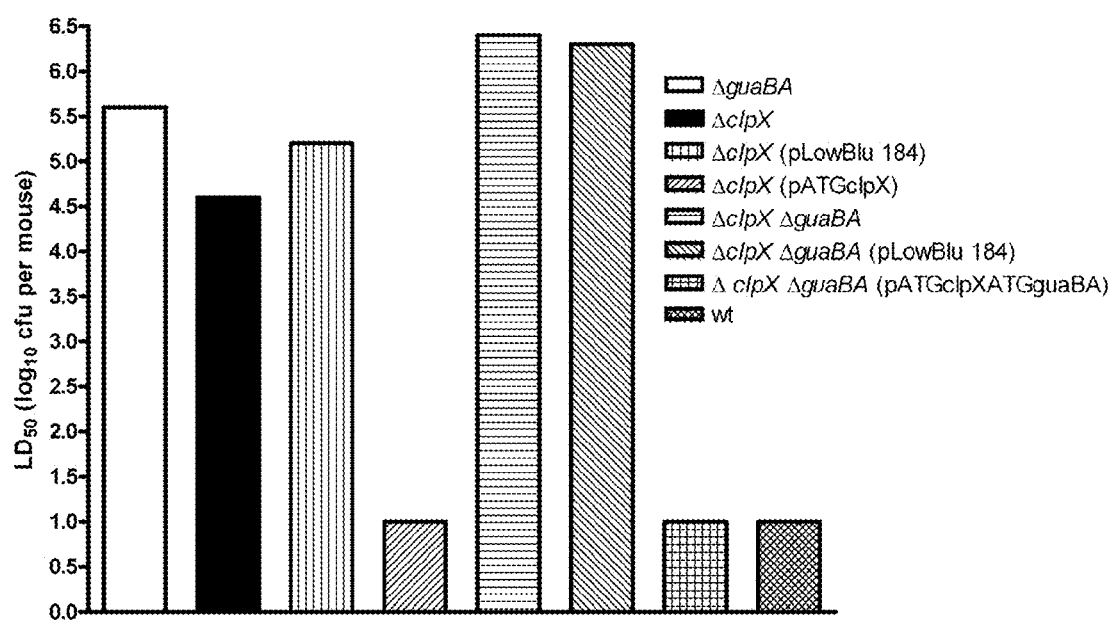
Figure 8:
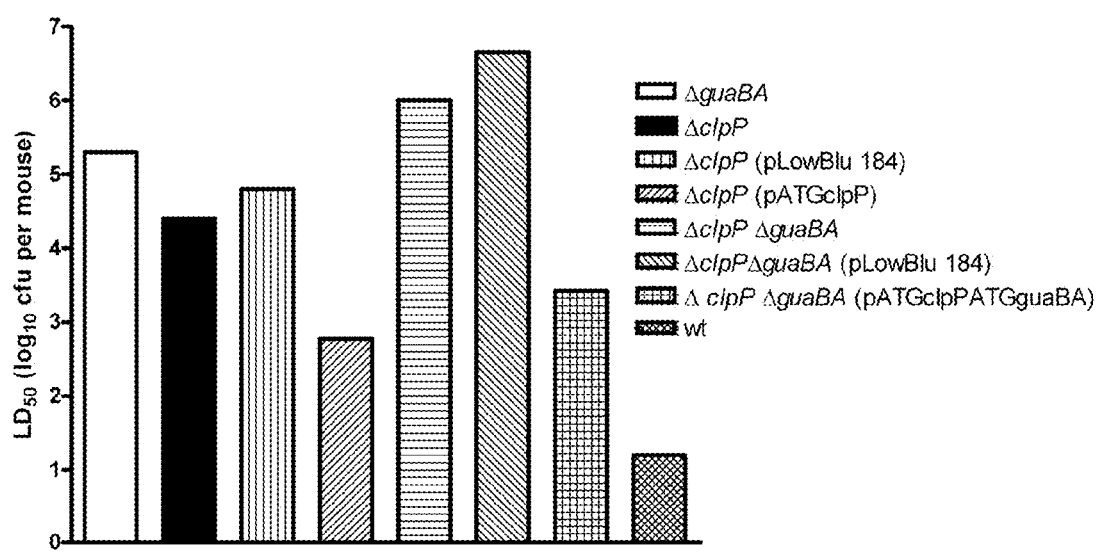

*S. Paratyphi* A 9150 was made electrocompetent and transformed with pKD46, resulting in strain CV 250. Lambda Red mutagenesis was performed on CV 250 using the PCR product generated using primers CVOL 28 and CVOL 32 with template pKD3 containing a cml resistance marker (see the Datsenko and Wanner reference for more information about this plasmid). Transformants were plated at 37° C., and those exhibiting cml resistance were screened by PCR using CVOL 13 and CVOL 15. Unmodified guaBA amplified from *S. Paratyphi* A 9150 was found to be ~3.5 kb (FIG. 1, lane 1), whereas a ~1.4 kb fragment was found in two clones with a mutated guaBA region (FIG. 1, lanes 2 and 3). These mutants were named CV 411 and CV 412, respectively. Treatment of these mutants with pCP20 (see Datsenko and Wanner reference for more information about this plasmid) liberated the cml resistance cartridge. Four deletants were analyzed by PCR with primers CVOL 13 and CVOL 15 and found to have a ~0.5 kb band (FIG. 2, lanes 2-4) in comparison to a guaBA:: cml progenitor (FIG. 2, lane 1). Resulting guaBA deletants of *S. Paratyphi* A 9150 were named CV 415-CV 418. The mutated guaBA region in CV 415 was PCR amplified with CVOL 15 and CVOL 13 and the product sequenced (polynucleotide sequence SEQ ID NO:1); the 5' and 3' regions of SEQ ID NO:1 are homologous to guaBA, whereas the center region is homologous to pKD3. Strain CV 415 was chosen for all subsequent studies.

7. In Vitro Complementation of the Deletion in guaBA

*S. Paratyphi* A 9150 contains an undefined auxotrophy, making it incapable of growth on minimal medium without the addition of casamino acids. ATCC strain 11511 and a CVD *S. Paratyphi* A isolate 516 are also unable to grow on minimal medium, suggesting that they contain the same auxotrophy as found in *S. Paratyphi* A 9150.

To demonstrate that Lambda Red-mediated mutagenesis only targeted guaBA in CV 415, a pLowBlu 184-based (low copy number) plasmid was designed containing a minimal fragment encoding guaBA under the control of the lactose promoter ($P_{lacZ}$). Primers CVOL 13 and CVOL 41 were used to amplify a ~3.1 kb fragment encoding guaBA with an optimized ribosome binding site (GAAGGAG) 8 bp upstream of the start codon using the chromosome of CVD 908-htrA as a template. This fragment was subcloned into pGEM®-T Easy and excised with EcoRI, blunted with T4 DNA polymerase and cloned into the NotI site of pLowBlu 184 creating pATG-guaBA (stored in CV 295).

CV 415 was electroporated with either pATGguaBA or pLowBlu 184 (control) and plated on 2× Soy media containing guanine and cml, creating strains CV 486 and CV 487, respectively. 2× soy medium lacking guanine is able to support the growth of guaBA deleted *S. Paratyphi* A. Single colonies of each were re-streaked onto MMM containing cml and incubated at 37° C. overnight. As shown in FIG. 3, CV 486 was able to grow on MMM (plate 2) in contrast to the control (CV 487; plate 1) indicating the minimal fragment cloned into pATGguaBA was able to complement the deletion of guaBA from the chromosome of CV 415.

8. Construction of Secondary Deletions in CV 415

In order to minimize the reversion of guaBA deleted *S. Paratyphi* A 9150 to a wild type (wt) genotype, additional genes were targeted as secondary attenuating markers. These genes were clpP and clpX, which encode a serine-protease and a chaperone ATPase, respectively (reviewed in Structure (Camb). 2004 February; 12(2):175-83). Disruption of clpP and/or clpX has been shown to significantly reduce the colonization potential of *Salmonella Typhimurium* in mice (Infect Immun. 2001 May; 69(5):3164-74). In *S. Typhi* Ty2, clpX (SEQ ID NO:39) and clpP (SEQ ID NO:40) are both located between 2483597 to 2485743 (SEQ ID NO:27) on the complementary strand of the chromosome, respectively, and are expressed from individual promoters. Wt *S. Paratyphi* A 9150 was also subjected to mutagenesis such that the virulence of mutants containing single deletions in either clpX or clpP could be assessed in mice.

To delete clpX, primers CVOL 85 and 86 were designed to amplify a ~1.3 kb fragment encoding clpX lacking a start codon from CVD 908-htrA. This fragment was column purified, Taq-Pro™ DNA Polymerase treated and cloned into pGEM®-T (stored in CV 472). The resulting vector, pGEM®-T::clpX was digested with NruI and EcoRI to remove a ~0.9 kb fragment, and treated with T4 DNA polymerase to create blunt ends. A cml cartridge isolated from pCR-Blunt II-TOPO as an EcoRI fragment was blunted and inserted into pGEM®-T::clpX. This cml cartridge had been previously created by PCR using CVOL 25 and CVOL 26 with pKD3 as a template (stored in CV 134). Following ligation and transformation, PCR was used with primers CVOL 26 and CVOL 85 to confirm insertion of the cml cartridge in the correct orientation for Lambda Red mutagenesis. A positive clone was identified, named pGEM®-T::(clpX::cml) and stored as CV 481.

guaBA deleted *S. Paratyphi* A (CV 415) was transformed with pKD46 and stored as CV 421. CV 421 and CV 250 (wt *S. Paratyphi* A 9150 transformed with pKD46) were subjected to Lambda Red mutagenesis with a ~1.4 kb PCR product amplified from pGEM®-T::(clpX::cml) using CVOL 85 and CVOL 86. Cml resistant mutants were isolated and screened by PCR with CVOL 87 and CVOL 88, which bind to regions outside those homologous to CVOL 85 and CVOL 86. Mutants exhibiting a correct PCR profile were selected for treatment with pCP20 to remove the cml cartridge. FIG. 4 shows that mutants containing an altered clpX gene exhibited a smaller ~0.6 kb band by PCR (Panel A, lanes 1-6) compared to that found in unaltered *S. Paratyphi* A 9150 (Panel A, lane 7). PCR analysis of the same strains with CVOL 13 and 15 confirmed that guaBA was deleted only from strains derived from CV 415 and not CV 250 (Panel B, lanes 4-6, compared to lanes 1-3 and 7). Mutants lacking clpX, and both clpX and guaBA, were stored as CV 532 and CV 534, respectively. The mutated clpX region in CV 532 and CV 534 was PCR amplified with primers CVOL 87 and CVOL 88 and the product sequenced (SEQ ID NO:2); the 5' and 3' regions of SEQ ID NO:2 are homologous to clpX, whereas the center region is homologous to pKD3.

To delete clpP, CVOL 89 and 90 were designed to amplify a ~0.7 kb fragment encoding clpP lacking a start codon from CVD 908-htrA. This fragment was column purified and cloned into pGEM®-T, creating pGEM®-T::clpP (stored as CV 470). pGEM®-T::clpP was digested with PstI and NsiI, T4 DNA polymerase treated and religated (creating pGEM®-T::clpPm, stored as CV 484) in order the remove NdeI and HincII sites from the vector backbone. pGEM®-T::clpPm was then digested with NdeI and HincII to remove DNA fragments totaling ~0.5 kb in size, and T4 DNA polymerase treated. Similarly to that abovementioned, a cml cartridge isolated from pCR-Blunt II-TOPO as an EcoRI fragment was T4 DNA polymerase treated and used to replace the fragments removed from pGEM®-T::clpPm. Following ligation and transformation, PCR was used with primers CVOL 26 and CVOL 85 to confirm insertion of the cml cartridge in the correct orientation for Lambda Red mutagenesis. A positive clone was identified, named pGEM®-T::(clpPm::cml) and stored as CV 501.

Wt and guaBA deleted S. Paratyphi A 9150 containing pKD46 (CV 250 and CV 421, respectively) were subjected to Lambda Red mutagenesis with a ~1.4 kb PCR product amplified from pGEM®-T::(clpPm::cml) using CVOL 89 and CVOL 90. Cml resistant mutants were isolated and screened by PCR with CVOL 91 and CVOL 92, which bind to regions outside those homologous to CVOL 89 and CVOL 90. Mutants exhibiting a correct PCR profile were selected for treatment with pCP20 to remove the cml cartridge.

FIG. 5 shows that mutants containing an altered clpP gene exhibited a smaller ~0.4 kb band by PCR (Panel A, lanes 1-6) compared to that found in unaltered *S. Paratyphi* A 9150 (Panel A, lane 7). PCR analysis of the same strains using primers CVOL 13 and 15 confirmed that guaBA was deleted only from strains derived from CV 415 and not from those based on CV 250 (Panel B, lanes 4-6, compared to lanes 1-3 and 7). Mutants lacking clpP, and both clpP and guaBA, were stored as CV 528 and CV 530, respectively. The mutated clpP region in CV 528 and CV 530 were PCR amplified with primers CVOL 87 and CVOL 88 and the product sequenced (polynucleotide sequence SEQ ID NO:3); the 5' and 3' regions of SEQ ID NO:3 are homologous to clpP, whereas the center region is homologous to pKD3.

9. Construction of Low Copy Plasmids for Complementation Analysis

As performed above, to confirm that the Lambda Red-mediated mutagenesis targeted only specific loci, mono- or bi-cistronic pLowBlu 184-based (low copy number) plasmids were designed containing minimal fragments encoding either clpX or clpP, or guaBA immediately downstream of either clpX or clpP. Constitutive expression of the genes in these plasmids was directed by $P_{lacZ}$.

Primers CVOL 64 and CVOL 65 were used to PCR amplify guaBA from CVD 908-htrA containing an enhanced ribosome binding site with NdeI and NsiI restriction sites at the 5' and 3' ends, respectively. The product was column purified and ligated into pCR-Blunt II-TOPO (stored as CV 394), extracted as a ~3.5 kb NdeI-NsiI fragment and cloned into the NdeI and NsiI sites in pLowBlu 184, creating pguaBAV.2 (stored as CV 482).

To create a low copy number plasmid encoding clpP, primers CVOL 122 and CVOL 123 were used to amplify clpP with an enhanced ribosome binding site from CVD 908-htrA with NotI and NruI sites at the 5' and 3' ends, respectively. The ~0.7 kb product was column purified and ligated into pCR-Blunt II-TOPO (stored as CV 567), extracted as a NotI-NruI fragment and ligated into pLowBlu 184 previously cut with NotI and NdeI, creating pATGclpP (stored as CV 584). To construct a bi-cistronic plasmid containing clpP and guaBA, primers CVOL 122 and CVOL 128 were designed to amplify clpP with an enhanced ribosome binding site from CVD 908-htrA with NotI sites at both the 5' and 3' ends. The 0.7 kb product was column purified and ligated into pCR-Blunt II-TOPO (stored as CV 600), extracted as a NotI fragment and ligated into pguaBAV.2 previously cut with NotI, creating pATGclpPATGguaBA (stored as CV 603).

To create a low copy plasmid encoding clpX, primers CVOL 124 and CVOL 125 were used to amplify clpX with an enhanced ribosome binding site from CVD 908-htrA with NotI and NdeI sites at the 5' and 3' ends, respectively. The ~1.3 kb product was column purified and ligated into pCR-Blunt II-TOPO (stored as CV 569), extracted as a NotI-NdeI fragment and ligated into either pLowBlu 184 or pguaBAV.2 both previously cut with NotI and NdeI, creating pATGclpX (stored as CV 582) and pATGclpXATGguaBA (stored as CV 573).

10. Assessment of Virulence of *S. Paratyphi* A and Mutants in Mice $LD_{50}$ studies were performed to compare the virulence of wt *S. Paratyphi* A 9150 with that of each mutant in intraperitoneally injected mice.

FIG. 6 shows the $LD_{50}$ data obtained with the injection of mice with wt and guaBA deleted *S. Paratyphi* A. Wt *S. Paratyphi* A has an $LD_{50}$ value of <10 bacteria per mouse. In contrast, guaBA deleted *S. Paratyphi* A had a $LD_{50}$ value ~4.5 logs greater. Complementation of the guaBA mutant with pLowBlu 184 did not alter the $LD_{50}$ value, whereas transformation with pATGguaBA restored wt-like virulence.

FIG. 7 shows the $LD_{50}$ data obtained with the injection of mice with wt *S. Paratyphi* A, clpX-deleted *S. Paratyphi* A, or clpX-guaBA-deleted *S. Paratyphi* A. The $LD_{50}$ values of wt and guaBA-deleted *S. Paratyphi* A were consistent with those achieved previously. clpX-deleted *S. Paratyphi* A displayed a ~1 log greater $LD_{50}$ value as compared to the guaBA mutants, indicating that a deletion in clpX was not as attenuating as that in guaBA. Complementation of the clpX-deleted or the clpX-guaBA deleted strains with pLowBlu 184 had no effect, whereas transformation with pATGclpX and pATGclpX-ATGguaBA, respectively, restored wt-like virulence.

FIG. 8 shows the $LD_{50}$ data of mice injected with wt *S. Paratyphi* A, clpP-deleted *S. Paratyphi* A or clpP-guaBA-deleted *S. Paratyphi* A. The $LD_{50}$ values of wt and guaBA-deleted *S. Paratyphi* A were consistent to those achieved previously. As with the clpX-deleted strain, clpP-deleted *S. Paratyphi* A exhibited increased virulence as compared to the guaBA mutant. This indicated that a deletion in clpP was not as attenuating as that in guaBA. Complementation of the clpX or the clpX-guaBA-deleted strains with pLowBlu 184 had no effect on virulence. Transformation of these strains with pATGclpP and pATGclpPATGguaBA, respectively, did not completely restore wt virulence. Without being bound by any theory, regulated expression of clpP, as opposed to unregulated expression as encoded by pATGclpP and pATGclp-PATGguaBA, is required to fully complement the clpP mutation.

11. *S. Paratyphi* A Derived Conjugate Vaccine

Conjugate vaccines are developed and tested as described herein. A conjugate vaccine comprises O polysaccharide (OPS) of *S. Paratyphi* A and a flagellin protein of *S. Paratyphi* A. In addition, a conjugate vaccine consists of OPS of *S. Paratyphi* A and a flagellin protein of *S. Paratyphi* A. Even more, a conjugate vaccine consists essentially of OPS of *S. Paratyphi* A and a flagellin protein of *S. Paratyphi* A.

A conjugate vaccine comprising a flagellin protein comprises any known flagellin protein (see, for example, International Application PCT/US2004/034910 and U.S. 60/512,878, which are incorporated by reference in their entirety). In particular aspects of the invention, a flagellin protein is any known flagellin protein of *S. Paratyphi* A. In other particular aspects of the invention, a flagellin protein is phase 1 flagellin (fliC).

A conjugate vaccine comprising OPS comprises any known OPS of *S. Paratyphi* A. In particular aspects of the invention, OPS belongs to Group A OPS which by definition exhibits immunodominant epitope 2 and usually also has non-dominant epitopes 1 and 12. The *Salmonella* Group A OPS contains a backbone of repeats of mannosyl-rhamnosyl-galactose to which the dideoxyhexose sugar paratose is linked alpha1,3 to the mannose residue. This gives rise to the immunodominant epitope "2" that defines the OPS of *Salmonella* Group A.

A broad-based vaccine against paratyphoid and typhoid fever is prepared by including conjugates to prevent *S. Paratyphi* B disease, *S. Paratyphi* C disease, and *S. Typhi* disease. The conjugates are made according to the same methods and strategies described herein of linking the relevant purified OPS to the homologous phase 1 flagellin protein. Thus, an *S. Paratyphi* B conjugate vaccine comprises, consists of, or consists essentially of Group B OPS conjugated to phase 1 flagella protein "b" (i.e., to the protein subunit encoded by fliC of *S. Paratyphi* B). An *S. Paratyphi* C conjugate vaccine comprises, consists of, or consists essentially of Group C1 OPS conjugated to phase 1 flagella protein "c" (i.e., conjugated to the protein subunit encoded by fliC of *S. Paratyphi* C). An *S. Typhi* conjugate vaccine comprises, consists of, or consists essentially of Group D OPS conjugated to phase 1 flagella protein "d" (i.e., conjugated to the protein subunit encoded by fliC of *S. Typhi*). In addition to the above-described conjugates being made according to the same methods and strategies, these conjugates are also administered and manufactured according the same methods and strategies described herein.

Conjugation of OPS of *S. Paratyphi* A and a flagellin protein of *S. Paratyphi* A can be carried out by methods known to one of ordinary skill in the art (see, for example, US Patent Application Publication No. 20090028889). In particular aspects of the invention drawn to conjugation of OPS of *S. Paratyphi* A and a flagellin protein of *S. Paratyphi* A, methods for the chemical conjugation of polypeptides, carbohydrates, and/or lipids are well known in the art (see, for example, Hermanson. Bioconjugate Techniques (Academic Press; 1992); Aslam and Dent, eds. Bioconjugation: Protein coupling Techniques for the Biomedical Sciences (MacMillan: 1998); and Wong Chemistry of Protein Conjugation and Cross-linking (CRC Press: 1991)). For example, in the case of carbohydrate or lipid conjugation, functional amino and sulfhydryl groups may be incorporated therein by conventional chemistry. For instance, primary amino groups may be incorporated by reaction with ethylenediamine in the presence of sodium cyanoborohydride and sulfhydryls may be introduced by reaction of cysteamin dihydrochloride followed by reduction with a standard disulfide reducing agent.

Heterobifunctional crosslinkers, such as, for example, sulfosuccinimidyl (4-iodoacetyl) aminobenzoate, which link the epsilon amino group on the D-lysine residues of copolymers of D-lysine and D-glutamate to a sulfhydryl side chain from an amino terminal cysteine residue on the peptide to be coupled, may be used to increase the ratio of OPS of *S. Paratyphi* A to a flagellin protein of *S. Paratyphi* A and/or a flagellin protein of *S. Paratyphi* A. to OPS of *S. Paratyphi* A in the conjugate.

OPS of *S. Paratyphi* A or a flagellin protein of *S. Paratyphi* A may contain amino acid side chains such as amino, carbonyl, hydroxyl, or sulfhydryl groups or aromatic rings that can serve as sites for conjugation. Residues that have such functional groups may be added to either OPS of *S. Paratyphi* A or to a flagellin protein of *S. Paratyphi* A. Such residues may be incorporated by solid phase synthesis techniques or recombinant techniques, both of which are well known in the art.

OPS of *S. Paratyphi* A and a flagellin protein of *S. Paratyphi* A may be chemically conjugated using conventional crosslinking agents such as carbodiimides. Examples of carbodiimides are 1-cyclohexyl-3-(2-morpholinyl-(4-ethyl) carbodiimide (CMC), 1-ethyl-3-(3-dimethyaminopropyl) carbodiimide (EDC), and 1-ethyl-3-(4-azonia-44-dimethylpentyl) carbodiimide.

Examples of other suitable crosslinking agents are cyanogen bromide, glutaraldehyde and succinic anhydride. In general, any of a number of homobifunctional agents including a homobifunctional aldehyde, a homobifunctional epoxide, a homobifunctional imidoester, a homobifunctional N-hydroxysuccinimide ester, a homobifunctional maleimide, a homobifunctional alkyl halide, a homobifunctional pyridyl disulfide, a homobifunctional aryl halide, a homobifunctional hydrazide, a homobifunctional diazonium derivative or a homobifunctional photoreactive compound may be used. Also included are heterobifunctional compounds, for example, compounds having an amine-reactive and a sulfhydryl-reactive group, compounds with an amine-reactive and a photoreactive group, and compounds with a carbonyl-reactive and a sulfhydryl-reactive group.

Specific examples of homobifunctional crosslinking agents include the bifunctional N-hydroxysuccinimide esters dithiobis(succinimidylpropionate), disuccinimidyl suberate, and disuccinimidyl tartarate; the bifunctional imidoesters dimethyl adipimidate, dimethyl pimelimidate, and dimethyl suberimidate; the bifunctional sulfhydryl-reactive crosslinkers 1,4-di-[3'-(2'-pyridyldithio)propion-amido]butane, bismaleimidohexane, and bis-N-maleimido-1,8-octane; the bifunctional aryl halides 1,5-difluoro-2,4-dinitrobenzene and 4,4'-difluoro-3,3'-dinitrophenylsulfone; bifunctional photoreactive agents such as bis-[b-(4-azidosalicylamide)ethyl] disulfide; the bifunctional aldehydes formaldehyde, malondialdehyde, succinaldehyde, glutaraldehyde, and adiphaldehyde; a bifunctional epoxied such as 1,4-butaneodiol diglycidyl ether; the bifunctional hydrazides adipic acid dihydrazide, carbohydrazide, and succinic acid dihydrazide; the bifunctional diazoniums o-tolidine, diazotized and bis-diazotized benzidine; the bifunctional alkylhalides N1N'-ethylene-bis(iodoacetamide), N1N'-hexamethylene-bis(iodoacetamide), N1N'-undecamethylene-bis(iodoacetamide), as well as benzylhalides and halomustards, such as ala'-diiodo-p-xylene sulfonic acid and tri(2-chloroethyl)amine, respectively.

Examples of other common heterobifunctional crosslinking agents that may be used include, but are not limited to, SMCC (succinimidyl-4-(N-maleimidomethyl)cyclohexane-1-carboxylate), MBS (m-maleimidobenzoyl-N-hydroxysuccinimide ester), SIAB (N-succinimidyl(4-iodacteyl) aminobenzoate), SMPB (succinimidyl-4-(p-maleimidophenyl)butyrate), GMBS (N-(-maleimidobutyryloxy)succinimide ester), MPHB (4-(4-N-maleimidopohenyl) butyric acid hydrazide), M2C2H (4-(N-maleimidomethyl)cyclohexane-1-carboxyl-hydrazide), SMPT (succinimidyloxycarbonyl-a-methyl-a-(2-pyridyldithio)toluene), and SPDP (N-succinimidyl 3-(2-pyridyldithio) propionate). For example, crosslinking may be accomplished by coupling a carbonyl group to an amine group or to a hydrazide group by reductive amination.

In another aspect of the invention, OPS of S. Paratyphi A and a flagellin protein of S. Paratyphi A are conjugated through polymers, such as PEG, poly-D-lysine, polyvinyl alcohol, polyvinylpyrollidone, immunoglobulins, and copolymers of D-lysine and D-glutamic acid. Conjugation of OPS of S. Paratyphi A to a flagellin protein of S. Paratyphi A may be achieved in any number of ways, including involving one or more crosslinking agents and functional groups on the OPS of S. Paratyphi A and/or a flagellin protein of S. Paratyphi A. The polymer may be derivatized to contain functional groups if it does not already possess appropriate functional groups.

Without being bound by theory, a conjugate vaccine of the invention made with OPS will stimulate bactericidal antibodies (Konadu E et al. Infect Immun 1996; 64(7):2709-15; Maclennan et al. J. Clin. Invest. 2008; 118:1553-62.) Using a flagellin protein as the carrier will result in enhanced serum 0 antibody responses because of the adjuvant (TLR5 agonist) effect of the flagellin protein (Feuillet et al. PNAS 2006; 103:12487-92; Gewirtz et al. J. Immunol. 2001; 167:1882-5; Huleatt et al. Vaccine. 2007; 25:763-75).

12. Vaccination Comprising a Conjugate Comprising OPS and a Flagellin Protein Vaccine strategies are well known in the art and therefore the vaccination strategy encompassed by the invention does not limit the invention in any manner. In certain aspects of the invention, the conjugate vaccine is administered alone in a single application or administered in sequential applications. In other aspects of the invention, the conjugate vaccine is administered as a component of a homologous or heterologous prime/boost regimen. In particular aspects of the invention drawn to heterologous prime/boost, a mucosal prime/parenteral boost immunization strategy is used. For example, an attenuated S. Paratyphi A strain as taught herein is administered orally and subsequently boosted parentally with a conjugate vaccine of OPS of S. Paratyphi A and a flagellin protein of S. Paratyphi A as described herein.

13. Methods of Large-Scale Manufacture of a Flagellin Protein Derived from S. Paratyphi A When generating attenuated vaccines for administration or for components used to make a conjugation vaccine (including, for example, OPS and a flagellin protein), attention to the degree of attenuation must be considered. In regard to large-scale manufacturing, attenuation is particularly important so as to ensure safety in the manufacturing process (including, for example, environmental safety). Manufacturing of an attenuated S. Paratyphi A of the invention is sufficiently attenuated to ensure safety of not only administration of the strain, but also manufacturing of the strain for the production of S. Paratyphi A to derive components for making a conjugate vaccine.

In particular aspects of the invention drawn to the S. Paratyphi A to derive components for making a conjugate vaccine, the attenuated strain produces, for example, more flagella than wild-type S. Paratyphi A or causes the export of a flagellin protein from S. Paratyphi A.

Figure 9:
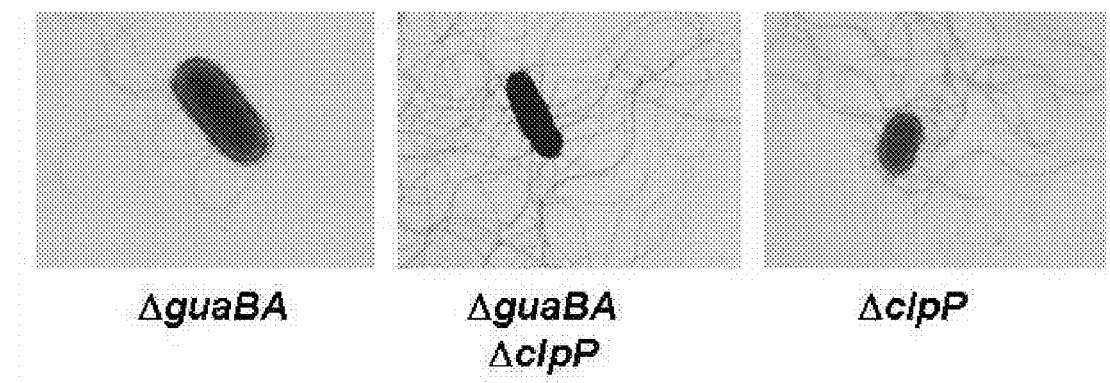

In certain aspects of the invention, an attenuated strain that having increased flagella compared to a wild-type strain is particularly advantageous from at least a manufacturing perspective. In particular aspects of the invention, an attenuated S. Paratyphi A strain having one or more mutations described herein leading to attenuation and hyperflagellation can be used for manufacturing an oral vaccine and/or components for a conjugate vaccine. For example, an attenuated strain of S. Paratyphi A having a mutation in the guaBA loci, the guaB gene, or the guaA gene, and mutation in the clpP gene produces an attenuated and a phenotypically hyperflagellated S. Paratyphi A strain (see, for example, FIG. 9). Methods of purification of a flagellin protein from whole flagella are known in the art or can be readily modified by one of ordinary skill in the art using methods know in the art. For example, by modifying the method of Ibrahim et al., purification of flagella is achieved; below pH 3.0, flagella dissociate into flagellin subunits (Ibrahim et al. J. Clin. Microbiol. 1985; 22:1040-4. Modern purification methods and clpP mutants should markedly increase yield and purity of a flagellin protein used to construct a conjugate vaccine of the invention (see, for example, Ogushi et al. J. Biol. Chem. 2001; 276:30521-6; Yoon et al. Infect. Immun. 2008; 76:1282-8).

In other aspects of the invention, export of a flagellin protein from an attenuated S. Paratyphi A straine is used to derive a flagellin protein used to construct a conjugate vaccine of the invention. For example, a mutation in the fliD gene, flgL gene, or flgK gene causes export of flagellin monomers into the supernatant. Therefore, an attenuated S. Paratyphi A strain of the invention has a mutation in at least the guaBA loci, the guaB gene, or the guaA gene, and mutation in the fliD gene, flgL gene, or flgK gene.

In a particular embodiment of the invention, S. Paratyphi A containing a guaBA mutation and a fliD mutation is made and used to derive a flagellin protein used to construct a conjugate vaccine of the invention. The mutation in guaBA has been described herein. The mutation of the fliD gene can be accomplished by a number of methods, including for example, knocking out the fliD gene. A method used to knockout fliD includes, for example, referencing Table 2, PCR #1 mixed with PCR #2 and then amplified with primers 5FliD and 3FRT-aph in an overlapping PCR, which generates a kanomycin-resistant fragment that is recovered in, for example, PSMART-LCAMP TM vector (Lucigen). PCR #3 can also be recovered in PSMART-LCAMP TM vector, then cut out with BamHI and XhoI, and inserted into the pSMART-fliD-aph clone cut with BamHI and XhoI. The final assembled fragment is cut out and electroporated into S. Paratyphi A carrying pKD46 and selection for kanomycin resistance according to the method of Datsenko and Wanner, followed by crossing out the aph cassette, where applicable, using pCP20 according to the method of Datsenko and Wanner (Proc Natl Acad Sci USA. 2000 Jun. 6; 97(12):6640-50).

TABLE 2

| | | |
|---|---|---|
| PCR #1 (using Salmonella guaBA chromosomal template DNA) | 5FliD: 5'-tcacgcacacgctgcaggttgttgttgatttc-3'<br>5FliD-rev: 5'-gaacttcGAAGCAGCTCCAGCacctaat gatgaaattgaagccatgc-3' | SEQ ID NO: 41<br>SEQ ID NO: 42 |
| PCR #2 (using pKD13 template DNA) | 5FRT-aph: 5'-GCTGGAGCTGCTTCgaagttc-3'<br>3FRT-aph: 5'-ctcgagTTCCGGGGATCCGTCGAC CTGCAGTTC-3' | SEQ ID NO: 43<br>SEQ ID NO: 44 |
| PCR #3 (using Salmonella guaBA chromosomal template DNA) | 3FliD: 5'-GGATCCgctatgaacaagtcctgataacagaggt-3'<br>3FliD-rev: 5'-CTCGAGttaacgagactcctggaaagatgcttt cggtgaaatctgc-3' | SEQ ID NO: 45<br>SEQ ID NO: 46 |

In addition to the attenuated *S. Paratyphi* A strains described herein for vaccination purposes and for deriving a flagellin protein used as a component of the conjugate vaccine described herein, these strains can be used to derive OPS that is used as a component of the conjugate vaccine described herein. The invention also encompasses any of the foregoing mutations in any combination that provides for maximum efficacy or manufacturing results (e.g., any combination of mutations in guaBA loci, the guaB gene, guaA gene, clpP gene, clpX gene, fliD gene, flgL gene, flgK gene, or any other mutation described herein can be made in all possible combinations or variations).

While the invention has been described with reference to certain particular examples and embodiments herein, those skilled in the art will appreciate that various examples and embodiments can be combined for the purpose of complying with all relevant patent laws (e.g., methods described in specific examples can be used to describe particular aspects of the invention and its operation even though such are not explicitly set forth in reference thereto).

CITED DOCUMENTS

The disclosure of references cited herein and the following references are incorporated herein in their entirety, as are all of the publications, patents, books, articles and other documents referred to and set forth throughout this application, whether or not specifically indicated to be incorporated in their entirety.

Levine M M, Herrington D, Murphy J R, Morris J G, Losonsky G, Tall B, Lindberg A, Svenson S, Baqar S, Edwards M F, Stocker B. Safety, infectivity, immunogenicity and in vivo stability of two attenuated auxotrophic mutant strains of *Salmonella Typhi,* 541Ty and 543Ty, as live oral vaccines in man. J Clin Invest 79:888-902, 1987.

Levine M M, Ferreccio C, Black R E, Chilean Typhoid Committee, Germanier R. Large-scale field trial of Ty21a live oral typhoid vaccine in enteric-coated capsule formulation. Lancet I:1049-1052, 1987.

Ferreccio C, Levine M M, Rodriguez H, Contreras R, Chilean Typhoid Committee. Comparative efficacy of two, three, or four doses of Ty21A live oral typhoid vaccine in enteric-coated capsules: a field trial in an endemic area. J Infect Dis 159:766-769, 1989.

Levine M M, Ferreccio C, Black R E, Tacket C O, Germanier R. Progress in vaccines against typhoid fever. Rev Infect Dis 2 (supplement 3):5552-5567, 1989.

Van de Verg L, Herrington D A, Murphy J R, Wasserman S S, Formal S B, Levine M M. Specific IgA secreting cells in peripheral blood following oral immunization with bivalent *Salmonella Typhi/Shigella sonnei* vaccine or infection with pathogenic *S. sonnei* in humans. Infect Immun 58:2002-2004, 1990.

Levine M M, Hone D, Heppner D G, Noriega F, Sriwathana B. Attenuated *Salmonella* as carriers for the expression of foreign antigens. Microecology and Therapy 19:23-32, 1990.

Herrington D A, Van De Verg L, Formal S B, Hale T L, Tall B D, Cryz S J, Tramont E C, Levine M M. Studies in volunteers to evaluate candidate *Shigella* vaccines: further experience with a bivalent *Salmonella Typhi-Shigella sonnei* vaccine and protection conferred by previous *Shigella sonnei* disease. Vaccine 8:353-357, 1990.

Cryz S J, Levine M M, Kaper J B. Randomized double-blind placebo-controlled trial to evaluate the safety and immunogenicity of the live oral cholera vaccine strain CVD 103-HgR in adult Swiss. Vaccine 8:577-580, 1990.

Levine M M, Ferreccio C, Cryz S, Ortiz E. Comparison of enteric-coated capsules and liquid formulation of Ty21a typhoid vaccine in a randomized controlled field trial. Lancet 336:891-894, 1990.

Servos S, Chatfield S, Hone D, Levine M M, Dimitriadis G, Pickard D, Dougan G, Fairweather N, Charles I. Molecular cloning and characterization of the aroD gene encoding 3-dehydroguinase from *Salmonella Typhi*. J Gen Micro 137:147-152, 1990.

Levine M M, Hone D, Tacket C, Ferreccio C, Cryz S. Clinical and field trials with attenuated *Salmonella Typhi* as live oral vaccines and as "carrier vaccines". Res Microbiol 141: 807-816, 1990.

Black R E, Levine M M, Ferreccio C, Clements M L, Lanata C, Rooney J, Germanier R, and the Chilean Typhoid Committee. Efficacy of one or two doses of Ty21a *Salmonella Salmonella Typhi* vaccine in enteric-coated capsules in a controlled field trial. Vaccine 8:81-84, 1990.

Tacket C O, Losonsky G, Taylor D N, Baron L, Kopeck D, Cryz S, Levine M M. Lack of immune response to the Vi component of a Vi-positive variant of the *Salmonella Typhi* live oral vaccine strain Ty21a in volunteer studies. J Infect Dis 163:901-904, 1991.

Hone D M, Harris A M, Chatfield S, Dougan G, Levine M M. Construction of genetically-defined double aro mutants of *Salmonella Typhi*. Vaccine 9:810-816, 1991.

Tacket C O, Hone D M, Curtiss R III, Kelly S M, Losonsky G, Guers L, Harris A M, Edelman R, Levine M M. Comparison of the safety and immunogenicity of ΔaroC ΔaroD and Δcya Δcrp *Salmonella typhi* strains in adult volunteers. Infect Immun 60:536-541, 1992.

Tacket C O, Hone D M, Losonsky G, Guers L, Edelman R, Levine M M. Clinical acceptability and immunogenicity of CVD 908 *Salmonella Typhi* vaccine strain. Vaccine 10:443-446, 1992.

Hone D M, Tacket C O, Harris A M, Kay B, Losonsky G, Levine M M. Evaluation in volunteers of a candidate live oral attenuated *Salmonella Typhi* vaccine. J Clin Invest 90:412-420, 1992.

Olanratmanee T, Levine M M, Losonsky G A, Thisyakorn U, Cryz S J Jr. Safety and immunogenicity of *Salmonella Typhi* Ty21a liquid formulation vaccine in 4- to 6-year-old That children. J Infect Dis 166:451-452, 1992.

Chatfield S N, Fairweather N, Charles I, Pickard D, Levine M M, Hone D, Posada M, Strugnell R A, Dougan G. Construction of a genetically defined *Salmonella Typhi* Ty2 aroA, aroC mutant for the engineering of a candidate live oral typhoid-tetanus vaccine. Vaccine 10:8-11, 1992.

Cryz S J Jr, Vanprapar N, Thisyakorn U, Olanratamanee T, Losonsky G, Levine M M, Chearskul S. Safety and immunogenicity of *Salmonella Typhi* Ty21a vaccine in young children. Infect Immun 61:1149-115, 1993.

Gonzalez C, Hone D, Noriega F, Tacket C O, Davis J R, Losonsky G, Nataro J P, Hoffman S, Malik A, Nardin E, Sztein M B, Heppner D G, Fouts T R, Isibasi A, Levine M M. *Salmonella Typhi* strain CVD 908 expressing the circumsporozoite protein of *Plasmodium falciparum*: strain construction, safety and immunogenicity. J Infect Dis 169: 927-931, 1994.

Sztein M B, Wasserman S S, Tacket C O, Edelman R, Hone D, Lindberg A A, Levine M M. Cytokine production patterns and lymphoproliferative responses in volunteers orally immunized with attenuated vaccine strains of *Salmonella Typhi*. J Infect Dis 170:1508-1517, 1994.

Hone D M, Harris A M, Lim V, Levine M M. Construction and characterization of isogenic O-antigen variants of *Salmonella Typhi*. Molec Microbiol 13:525-530, 1994.

Pickard D, Li J, Roberts M, Maskell D, Hone D, Levine M, Dougan G, Chatfield S. Characterization of defined ompR mutants of *Salmonella Typhi*: ompR is involved in the regulation of Vi polysaccharide expression. Infect Immun 62:3984-3993, 1994.

Noriega F R, Wang J Y, Losonsky G, Maneval D R, Hone D M, Levine M M. Construction and characterization of attenuated ΔaroA ΔvirG *Shigella flexneri* 2a strain CVD 1203, a prototype live oral vaccine. Infect Immun 62:5168-5172, 1995.

Gómez-Duarte, O G, Galen J, Chatfield S N, Rappuoli R, Eidels L, Levine M M. Expression of fragment C of tetanus toxin fused to a carboxyl-terminal fragment of diphtheria toxin in *Salmonella Typhi* CVD 908 vaccine strain. Vaccine 13:1596-1602, 1995.

Cryz S J Jr, Que J U, Levine M M, Wiedermann G, Kollaritsch H. Safety and immunogenicity of a live oral bivalent typhoid fever (*Salmonella Typhi*-Ty21a) cholera (*Vibrio cholerae* CVD 103-HgR) vaccine in healthy adults. Infect Immun 63:1336-1339, 1995.

Sztein M B, Tanner M K, Polotsky Y, Orenstein J M, Levine M M. Cytotoxic T lymphocytes after oral immunization with attenuated strains of *Salmonella Typhi* in humans. Immunol 155:3987-3993, 1995.

Levine M M, Galen J, Barry E, Noriega F, Chatfield S, Dougan G, Tacket C. Attenuated *Salmonella* as live oral vaccines against typhoid fever and as live vectors. J Biotechnology 44:193-196, 1995.

Noriega F R, Losonsky G, Wang J Y, Formal S B, Levine M M. Further characterization of ΔaroA, ΔvirG *Shigella flexneri* 2a strain CVD 1203 as a mucosal *Shigella* vaccine and as a live vector for delivering antigens of enterotoxigenic *Escherichia coli*. Infect Immun 64:23-27, 1996.

Noriega F R, Losonsky G, Lauderebaugh C, Liao F M, Wang J Y, Levine M M. Engineered ΔguaBA ΔvirG *Shigella flexneri* 2a strain CVD 1205: construction, safety, immunogenicity, and potential efficacy as a mucosal vaccine. Infect Immun 64:3055-3061, 1996.

Kotloff K, Noriega F, Losonsky G, Sztein M B, Nataro J P, Levine M M. Safety, immunogenicity and transmissibility in humans of CVD 1203, a live oral *Shigella flexneri* 2a vaccine candidate attenuated by deletions in aroA and virG. Infect Immun 64:4542-4548, 1996.

Barry E M, Gómez-Duarte O, Chatfield S, Rappuoli R, Losonsky G A, Galen J E, Levine M M. Expression and immunogenicity of pertussis toxin S1 subunit-tetanus toxin fragment C fusions in *Salmonella Typhi* vaccine strain CVD 908. Infect Immun 64:4172-4181, 1996.

Tacket C O, Sztein M B, Losonsky G A, Wasserman S S, Nataro J P, Edelman R, Galen J E, Pickard D, Dougan G, Chatfield S N, Levine M M. Safety of live oral *Salmonella Typhi* vaccine strains with deletions in htrA and aroC aroD and immune response in humans. Infect Immun 65:452-456, 1997.

Levine M M, Galen J, Barry E, Noriega F, Tacket C, Sztein M, Chatfield S, Dougan G, Losonsky G, Kotloff K. Attenuated *Salmonella Typhi* and *Shigella* as live oral vaccines and as live vectors. Behring Inst Mitt 98:120-123, 1997.

Tacket C O, Kelly S M, Schodel F, Losonsky G, Nataro J P, Edelman R, Levine M M, Curtiss R III. Safety and immunogenicity in humans of an attenuated *Salmonella* Typhi-vaccine vector strain expressing plasmid-encoded hepatitis B antigens stabilized by the Asd-balanced lethal system. Infect Immun 65:3381-3385, 1997.

Gonzalez C R, Noriega F R, Huerta S, Santiago A, Vega M, Paniagua J, Ortiz-Navarrete V, Isibasi A, Levine M M. Immunogenicity of a *Salmonella Typhi* CVD 908 candidate vaccine strain expressing the major surface protein gp63 of *Leishmania mexicana mexicana*. Vaccine 16:9/10 1043-1052, 1998.

Orr N, Galen J E, Levine M M. Expression and immunogenicity of a mutant diphtheria toxin molecule, CRM197, and its fragments in *Salmonella Typhi* vaccine strain CVD 908-htrA. Infect Immun 67:4290-4294, 1999.

Levine M M, Ferreccio C, Abrego P, San Martin O, Ortiz E, Cryz S C. Duration of efficacy of Ty21a, attenuated *Salmonella Typhi* live oral vaccine. Vaccine 17:2 Supplement S22-S27, 1999.

Pasetti M F, Anderson R J, Noriega F R, Levine M M, Sztein M B. Attenuated ΔguaBA *Salmonella Typhi* vaccine strain CVD 915 as a live vector utilizing prokaryotic or eukaryotic expression systems to deliver foreign antigens and elicit immune responses. Clin Immun 92:76-89, 1999.

Galen J E, Nair J, Wang J Y, Tanner M K, Sztein M B, Levine M M. Optimization of plasmid maintenance in the attenuated live vector vaccine *Salmonella Typhi* strain CVD 908-htrA. Infect Immun 67:6424-6433, 1999.

Kotloff K L, Noriega F R, Samandari T, Sztein M B, Losonsky G A, Nataro J P, Picking W D, Levine M M. *Shigella flexneri* 2a strain CVD 1207 with specific deletions in virG, sen, set and guaBA is highly attenuated in humans. Infect Immun 68:1034-39, 2000.

Tacket C O, Sztein M B, Wasserman S S, Losonsky G, Kotloff K L, Wyant T L, Nataro J P, Edelman R, Perry J, Bedford P, Brown D, Chatfield S, Dougan G, Levine M M. Phase 2 clinical trial of attenuated *Salmonella enterica* serovar Typhi oral live vector vaccine CVD 908-htrA in U.S. volunteers. Infect Immun 68:1196-1201, 2000.

Anderson R J, Pasetti M F, Sztein M B, Levine M M, Noriega F R. AguaBA attenuated *Shigella flexneri* 2a strain CVD 1204 as a *Shigella* vaccine and as a live mucosal delivery system for fragment C of tetanus toxin. Vaccine 18:2193-2202, 2000.

Tacket C O, Galen J, Sztein M B, Losonsky G, Wyant T L, Nataro J, Wasserman S S, Edelman R, Chatfield S, Dougan G, Levine M M. Safety and immune responses to attenuated *Salmonella enterica* serovar Typhi oral live vector vaccines expressing tetanus toxin fragment C. Clin Immunol 97:146-153, 2000.

Pasetti M F, Tanner M K, Pickett T E, Levine M M, Sztein M. Mechanisms and cellular events associated with the priming of mucosal and systemic immune responses to *Salmonella enterica* serovar Typhi live vector vaccines delivered intranasally in the murine model. Vaccine 18:3208-3213, 2000.

Wu S, Beier M, Sztein M, Galen J E, Pickett T, Holder A A, Gómez-Duarte O, Levine M M. Construction and immunogenicity in mice of attenuated *Salmonella Typhi* expressing *Plasmodium falciparum* merozoite surface protein (MSP-1) fused to tetanus toxin fragment C. J. Biotechnol. 83:125-135, 2000.

Wang J Y, Noriega F R, Galen J E, Barry E, Levine M M. Constitutive expression of the Vi polysaccharide capsular antigen in attenuated *Salmonella enterica* serovar Typhi oral vaccine strain CVD 909. Infect Immun 68:4647-4652, 2000.

Koprowski H II, Levine M M, Anderson R A, Losonsky G, Pizza M, Barry E M. Attenuated *Shigella flexneri* 2a vaccine strain CVD 1204 expressing colonization factor antigen I and mutant heat-labile enterotoxin of enterotoxigenic *Escherichia coli*. Infect Immun 68:4884-92, 2000.

Gómez-Duarte O, Pasetti M, Santiago A, Sztein M B, Hoffman S L, Levine M M. Expression, secretion and immunogenicity of the *Plasmodium falciparum* SSP-2 protein in *Salmonella* vaccine strains by a type I secretion system. Infect Immun 69:1192-1198, 2001.

Orr N, Galen J E, Levine M M. Novel use of anaerobically induced promoter, dmsA, for controlled expression of Fragment C of tetanus toxin in live attenuated *Salmonella enterica* serovar Typhi strain CVD 908-htrA. Vaccine 19:1694-1700, 2001.

Altboum Z, Barry E M, Losonsky G, Galen J E, Levine M M. Attenuated *Shigella flexneri* 2a AguaBA strain CVD 1204 expressing ETEC CS2 and CS3 fimbriae as a live mucosal vaccine against *Shigella* and enterotoxigenic *Escherichia coli* infection. Infect Immun 69:3150-8, 2001.

Wang J Y, Pasetti M F, Noriega F R, Anderson R S, Wasserman S S, Galen J E, Sztein M B, Levine M M. Construction, genotypic and phenotypic characterization, and immunogenicity of attenuated AguaBA *Salmonella enterica* serovar Typhi strain CVD 915. Infect Immun 69:4734-4741, 2001.

Galen J E, Levine M M. Can a "flawless" live vector vaccine strain be engineered? Trends Microbiol 9:372-376, 2001.

Kotloff K L, Taylor D N, Sztein M B, Wasserman S S, Losonsky G A, Nataro J P, Venkatesan M, Hartman A, Picking W D, Katz D E, Campbell J D, Levine M M, Hale T L. Phase I evaluation of ΔvirG *Shigella sonnei* live, attenuated, oral vaccine strain WRSS1 in healthy adults. Infect Immun 70:2016-21, 2002.

Pasetti, M, Levine M M, Sztein M B. Animal models paving the way for clinical trials of attenuated *Salmonella enterica* serovar Typhi live oral vaccines and live vectors. Vaccine. 21:401-18, 2003.

Pasetti M F, Barry E M, Losonsky G, Singh M, Medina-Moreno, S M, Polo J M, Robinson H, Sztein M B, Levine M M. Attenuated *Salmonella enterica* serovar Typhi and *Shigella flexneri* 2a strains mucosally deliver DNA vaccines encoding measles virus hemagglutinin, inducing specific immune responses and protection in cotton rats. J Virol 77:5209-5217, 2003.

Salerno-Goncalves R, Wyant T L, Pasetti M F, Fernandez-Vina M, Tacket C O, Levine M M, Sztein M B. Concomitant Induction of CD4(+) and CD8(+) T Cell Responses in Volunteers Immunized with *Salmonella enterica* Serovar Typhi Strain CVD 908-htrA. J 1 mmol. 170:2734-2741, 2003.

Tacket C O, Pasetti M F, Sztein, M B, Livio S, Levine M M. Immune responses to an oral Typhoid vaccine strain modified to constitutively express Vi capsular polysaccharide. J Infect Dis, 190:565-570, 2004.

Vindurampulle C J, Cuberos L F, Barry E M, Pasetti M F, Levine M M. Recombinant *Salmonella enterica* serovar Typhi in a prime-boost strategy. Vaccine 22(27-28):3744-3750, 2004.

Capozzo A V, Cuberos L, Levine M M, Pasetti M F. Mucosally delivered *Salmonella* live vector vaccines elicit potent immune responses against a foreign antigen in neonatal mice born to naive and immune mothers. Infect Immun 72:4637-4646, 2004.

Kotloff K L, Pasetti M F, Barry E M, Nataro J P, Wasserman S S, Sztein M B, Picking W D, Levine M M. Deletion in the *Shigella* enterotoxin genes further attenuates *Shigella flexneri* 2a bearing guanine auxotrophy in a Phase 1 trial of CVD 1204 and CVD 1208. J Infect Dis 190:1745-1754, 2004.

Galen J E, Zhao L, Chinchilla M, Wang J Y, Pasetti M F, Green J, Levine M M. Adaptation of the endogenous *Salmonella enterica* serovar Typhi clyA-encoded hemolysin for antigen export enhances the immunogenicity of anthrax protective antigen domain 4 expressed by the attenuated live vector vaccine strain CVD 908-htrA. Infect Immun 72:7096-7106, 2004.

What is claimed is:

1. A method for preparing a conjugate vaccine, comprising:
- (a) mutating a strain of *Salmonella Paratyphi* A to generate an attenuated strain of *Salmonella Paratyphi* A,
- (b) isolating an O polysaccharide (OPS) and a flagellin protein from the attenuated strain of (a), wherein said flagellin protein is phase 1 flagellin (fliC), and
- (c) conjugating the OPS to the flagellin protein, thereby preparing a conjugate vaccine.

2. The method of claim 1, wherein said OPS of *Salmonella Paratyphi* A belongs to Group A OPS of *Salmonella*.

3. The method of claim 1, wherein said attenuated *Salmonella Paratyphi* A strain comprises one or more genetic mutations selected from the group consisting of a mutation of the guaBA loci, a mutation of the guaB gene, a mutation of the guaA gene, a mutation of the clpP gene, a mutation of the clpX gene, a mutation of the fliD gene, a mutation of the flgK gene, and a mutation of the flgL gene.

4. The method of claim 3, wherein said attenuated *Salmonella Paratyphi* A strain comprises a mutation of the guaBA loci and a mutation of the clpP gene.

5. The method of claim 4, wherein the mutation of the guaBA loci and the mutation of the clpP gene is a deletion of part or all of the guaBA loci and a deletion of part or all of the clpP gene.

6. The method of claim 1, wherein conjugating is via chemical conjugation.

7. The method of claim 3, wherein said attenuated *Salmonella Paratyphi* A strain comprises a mutation of the guaBA loci and a mutation of the fliD gene.

8. The method of claim 7, wherein the mutation of the guaBA loci and the mutation of the fliD gene is a deletion of part or all of the guaBA loci and a deletion of part or all of the fliD gene.

9. The method of claim 3, wherein said attenuated *Salmonella Paratyphi* A strain comprises a mutation of the guaBA loci and a mutation of the flgK gene.

10. The method of claim 9, wherein the mutation of the guaBA loci and the mutation of the flgK gene is a deletion of part or all of the guaBA loci and a deletion of part or all of the flgK gene.

11. The method of claim 3, wherein said attenuated *Salmonella Paratyphi* A strain comprises a mutation of the guaBA loci and a mutation of the flgL gene.

12. The method of claim 11, wherein the mutation of the guaBA loci and the mutation of the flgL gene is a deletion of part or all of the guaBA loci and a deletion of part or all of the flgL gene.

* * * * *

SEQUENCE LISTING

```
<160> NUMBER OF SEQ ID NOS: 50

<210> SEQ ID NO 1
<211> LENGTH: 489
<212> TYPE: DNA
<213> ORGANISM: Artificial Sequence
<220> FEATURE:
<223> OTHER INFORMATION: chemically-synthesized mutated guaBA region

<400> SEQUENCE: 1
ggaacatcgc acagcgcacc tgagcggtat cgtctttgag cgtaaagtac cagtggcccg      60
acgcaggctg cgtgaaatta gaaatctcgc cgctgatcca tacctgtccc atctcctgtt     120
```

```
ctaacagcag acgaaccgtc tggttaaggc ggcttacggt aaaaattgag gaagtttgag      180
aggataacat gtgagcggga tcaaattcta atcagcagg  ttattcaatc ggtgtaggct      240
ggagcctgct tcgaagttcc tatactttct agagaatagg aacttcggaa taggaactaa      300
ggaggatatt catatgctct ctctctgcgt gctgtcgaaa ccatcgactt tatgaccgcg      360
cactgggcgc acctgccgta tgacttcctg ggtcgtgttt ccaaccgcat catcaatgaa      420
gtcaacggga tttcccgtgt ggtgtatgac atcagcggta accaccggc  taccattgag      480 tgggaatga                                                              489
```

```
<210> SEQ ID NO 2
<211> LENGTH: 634
<212> TYPE: DNA
<213> ORGANISM: Artificial Sequence
<220> FEATURE:
<223> OTHER INFORMATION: chemically-synthesized mutated clpX region

<400> SEQUENCE: 2
cctgagaatg gcatttgcgt cgtcgtgtgc ggcacaaaga acaaagaaga ggttttgact       60
catgacagat aaacgcaaag atggctcggg caaattgttg tactgctctt tttgcggcaa      120
aagccagcat gaagtgcgca agctgattgc cggtccatcc gtgtatatct gcgacgaatg      180
cgtcgattta tgtaacgaca ttattcgcgc ccttatatat atgcggccgc gtaggctgg       240 agctgcttcg aagttcctat actttctaga gaataggaac ttcggaatag gaactaagga      300
ggatattcat atggcgcgcc tataagggcg aattccgtga cgaagcgctg aacgctatcg      360
ccaggaaagc aatggcgcgt aaaaccggtg cccgtggtct gcgttctatc gtcgaagcgg      420
cgctgctgga taccatgtac gatttgccat ctatggaaga cgtcgaaaaa gtggtgatcg      480
acgagtccgt tattgccggt cagagtaagc cgttgctgat ttacggcaaa ccggaagcgc      540
aggcttctgg cgaataatta aacattcata caatcagtta gccaaaaaag ggggattttt      600
atctcccctt tcgttttttcc tgtaaacacg ccgt                                 634
```

```
<210> SEQ ID NO 3
<211> LENGTH: 370
<212> TYPE: DNA
<213> ORGANISM: Artificial Sequence
<220> FEATURE:
<223> OTHER INFORMATION: chemically-synthesized mutated clpP region

<400> SEQUENCE: 3
tccatcaggt tacaatcagt acagcaggtt ttttcaattt ttatccagga gacggaaatg       60
tcatacagcg gagaacgaga taatttggcc cctcatatat gaatatcctc cttagttcct      120
attccgaagt tcctattctc tagaaagtat aggaacttcg aagcagctcc agcctacacg      180
ctaggactca attttgaccc atcgtaattg atgccctgga cgcaagtgtg ccgctataca      240
cttcatcctt cacgctacct cggtgttggt tgccagcgcg cctcccggtg acttacttat      300
gtaagcgcct gcggagtcgc cgagttgccg ccttgatgta gctcgaatga ttttgtgtat      360
atactaatga                                                             370
```

```
<210> SEQ ID NO 4
<211> LENGTH: 27
<212> TYPE: DNA
<213> ORGANISM: Artificial Sequence
<220> FEATURE:
<223> OTHER INFORMATION: chemically-synthesized oligonucleotide primer

<400> SEQUENCE: 4
```

```
ctgcagtcat tcccactcaa tggtagc                                         27

<210> SEQ ID NO 5
<211> LENGTH: 18
<212> TYPE: DNA
<213> ORGANISM: Artificial Sequence
<220> FEATURE:
<223> OTHER INFORMATION: chemically-synthesized oligonucleotide primer

<400> SEQUENCE: 5
ggaacatcgc acagcgca                                                   18

<210> SEQ ID NO 6
<211> LENGTH: 17
<212> TYPE: DNA
<213> ORGANISM: Artificial Sequence
<220> FEATURE:
<223> OTHER INFORMATION: chemically-synthesized oligonucleotide primer

<400> SEQUENCE: 6
gtgtaggagc tgcttcg                                                    17

<210> SEQ ID NO 7
<211> LENGTH: 20
<212> TYPE: DNA
<213> ORGANISM: Artificial Sequence
<220> FEATURE:
<223> OTHER INFORMATION: chemically-synthesized oligonucleotide primer

<400> SEQUENCE: 7
catatgaata tcctccttag                                                 20

<210> SEQ ID NO 8
<211> LENGTH: 119
<212> TYPE: DNA
<213> ORGANISM: Artificial Sequence
<220> FEATURE:
<223> OTHER INFORMATION: chemically-synthesized oligonucleotide primer

<400> SEQUENCE: 8
cgaaccgtct ggttaaggcg gcttacggta aaaattgagg aagtttgaga ggataacatg     60
tgagcgggat caaattctaa atcagcaggt tattcaatcg tgtaggctgg agctgcttc    119

<210> SEQ ID NO 9
<211> LENGTH: 120
<212> TYPE: DNA
<213> ORGANISM: Artificial Sequence
<220> FEATURE:
<223> OTHER INFORMATION: chemically-synthesized oligonucleotide primer

<400> SEQUENCE: 9
ttcattgatg atgcggttgg aaacacgacc caggaagtca tacggcaggt gcgcccagtg     60
cgcggtcata aagtcgatgg tttcgacagc acgcagagag catatgaata tcctccttag   120

<210> SEQ ID NO 10
<211> LENGTH: 28
<212> TYPE: DNA
<213> ORGANISM: Artificial Sequence
<220> FEATURE:
<223> OTHER INFORMATION: chemically-synthesized oligonucleotide primer

<400> SEQUENCE: 10
gaaggagtat tgcccatgct acgtatcg                                        28

<210> SEQ ID NO 11
```

```
<211> LENGTH: 42
<212> TYPE: DNA
<213> ORGANISM: Artificial Sequence
<220> FEATURE:
<223> OTHER INFORMATION: chemically-synthesized oligonucleotide primer

<400> SEQUENCE: 11
catatgaagg agtattgccc atgctacgta tcgctaaaga ag                              42

<210> SEQ ID NO 12
<211> LENGTH: 36
<212> TYPE: DNA
<213> ORGANISM: Artificial Sequence
<220> FEATURE:
<223> OTHER INFORMATION: chemically-synthesized oligonucleotide primer

<400> SEQUENCE: 12
atgcatctgc agtcattccc actcaatggt agccgg                                    36

<210> SEQ ID NO 13
<211> LENGTH: 30
<212> TYPE: DNA
<213> ORGANISM: Artificial Sequence
<220> FEATURE:
<223> OTHER INFORMATION: chemically-synthesized oligonucleotide primer

<400> SEQUENCE: 13
acagataaac gcaaagatgg ctcgggcaaa                                           30

<210> SEQ ID NO 14
<211> LENGTH: 30
<212> TYPE: DNA
<213> ORGANISM: Artificial Sequence
<220> FEATURE:
<223> OTHER INFORMATION: chemically-synthesized oligonucleotide primer

<400> SEQUENCE: 14
ttattcgcca gaagcctgcg cttccggttt                                           30

<210> SEQ ID NO 15
<211> LENGTH: 30
<212> TYPE: DNA
<213> ORGANISM: Artificial Sequence
<220> FEATURE:
<223> OTHER INFORMATION: chemically-synthesized oligonucleotide primer

<400> SEQUENCE: 15
cctgagaatg gcatttgcgt cgtcgtgtgc                                           30

<210> SEQ ID NO 16
<211> LENGTH: 30
<212> TYPE: DNA
<213> ORGANISM: Artificial Sequence
<220> FEATURE:
<223> OTHER INFORMATION: chemically-synthesized oligonucleotide primer

<400> SEQUENCE: 16
acggcgtgtt tacaggaaaa acgaaagggg                                           30

<210> SEQ ID NO 17
<211> LENGTH: 30
<212> TYPE: DNA
<213> ORGANISM: Artificial Sequence
<220> FEATURE:
<223> OTHER INFORMATION: chemically-synthesized oligonucleotide primer

<400> SEQUENCE: 17
```
tcatacagcg gagaacgaga taatttggcc                                         30

<210> SEQ ID NO 18
<211> LENGTH: 30
<212> TYPE: DNA
<213> ORGANISM: Artificial Sequence
<220> FEATURE:
<223> OTHER INFORMATION: chemically-synthesized oligonucleotide primer

<400> SEQUENCE: 18
ttacataagt aagtcactgg gaggcgcgct                                         30

<210> SEQ ID NO 19
<211> LENGTH: 30
<212> TYPE: DNA
<213> ORGANISM: Artificial Sequence
<220> FEATURE:
<223> OTHER INFORMATION: chemically-synthesized oligonucleotide primer

<400> SEQUENCE: 19
tccatcaggt tacaatcagt acagcagatt                                         30

<210> SEQ ID NO 20
<211> LENGTH: 30
<212> TYPE: DNA
<213> ORGANISM: Artificial Sequence
<220> FEATURE:
<223> OTHER INFORMATION: chemically-synthesized oligonucleotide primer

<400> SEQUENCE: 20
tcattagtat atacacaaaa tcattcgagc                                         30

<210> SEQ ID NO 21
<211> LENGTH: 45
<212> TYPE: DNA
<213> ORGANISM: Artificial Sequence
<220> FEATURE:
<223> OTHER INFORMATION: chemically-synthesized oligonucleotide primer

<400> SEQUENCE: 21
gcggccgcga aggagagacg gaaatgtcat acagcggaga acgag                        45

<210> SEQ ID NO 22
<211> LENGTH: 42
<212> TYPE: DNA
<213> ORGANISM: Artificial Sequence
<220> FEATURE:
<223> OTHER INFORMATION: chemically-synthesized oligonucleotide primer

<400> SEQUENCE: 22
tcgcgagaat tcttacataa gtaagtcact gggaggcgcg ct                           42

<210> SEQ ID NO 23
<211> LENGTH: 45
<212> TYPE: DNA
<213> ORGANISM: Artificial Sequence
<220> FEATURE:
<223> OTHER INFORMATION: chemically-synthesized oligonucleotide primer

<400> SEQUENCE: 23
gcggccgcga aggagtttga ctcatgacag ataaacgcaa agatg                        45

<210> SEQ ID NO 24
<211> LENGTH: 36
<212> TYPE: DNA
<213> ORGANISM: Artificial Sequence
<220> FEATURE:

<223> OTHER INFORMATION: chemically-synthesized oligonucleotide primer

<400> SEQUENCE: 24

```
catatgttat tcgccagaag cctgcgcttc cggttt                                36
```

<210> SEQ ID NO 25
<211> LENGTH: 38
<212> TYPE: DNA
<213> ORGANISM: Artificial Sequence
<220> FEATURE:
<223> OTHER INFORMATION: chemically-synthesized oligonucleotide primer

<400> SEQUENCE: 25

```
gcggccgctt acataagtaa gtcactggga ggcgcgct                              38
```

<210> SEQ ID NO 26
<211> LENGTH: 3120
<212> TYPE: DNA
<213> ORGANISM: Salmonella Typhi Ty2

<400> SEQUENCE: 26

```
ttgcccatgc tacgtatcgc taaagaagcc ctgacgtttg acgacgtcct ccttgttccc        60
gctcactcca ccgttttgcc gaatactgct gatctcagca cgcagttgac gaaaactatt       120
cgtctgaata ttcctatgct ttctgcggcg atggacaccg tgacggaagc gcgcctggca       180
attgccctgg cccaggaagg cggcatcggt tttatccaca aaaacatgtc tattgagcgc       240
caggcggaag aagttcgccg cgtgaagaaa cacgagtccg cgtagtgac cgacccgcag        300
accgtcctgc caaccaccac gttgcatgaa gtgaaagccc tgaccgagcg taacggtttt       360
gcgggctatc cggtggtgac tgaagataac gagctggtgg gtatcatcac cggtcgtgac       420
gtgcgttttg tgactgacct gaaccagccg gtgagtgttt acatgacgcc gaaagagcgt       480
ctggtgaccg ttcgtgaagg cgaagcccgt gaagtcgtgc tggcaaaaat gcacgaaaaa       540
cgcgtagaaa aagcgctggt cgttgatgat aacttccatc tgcttggcat gattaccgta       600
aaagatttcc agaaagcgga acgtaaacca aactcctgta agatgagca gggccgttta       660
cgtgtcggcg cggcggtcgg cgcaggcgcg ggcaacgaag agcgcgttga cgcgctggtg       720
gcggcaggcg ttgacgtcct gctgatcgac tcttctcacg gtcactctga aggcgtgttg       780
caacgtatcc gtgaaacccg tgctaaatat cctgacctgc aaatcatcgg cggcaacgtc       840
gcgacgggcg caggcgctcg cgcactggcg gaagccggtt gcagcgcggt gaaagtcggt       900
atcggcccgg gttccatctg taccactcgt atcgtgactg gcgtgggcgt tccgcagatt       960
accgctgttt ctgacgcagt tgaagcgctg gaaggcaccg ggattccggt tatcgctgac      1020
ggcggtatcc gtttctccgg cgacatcgcc aaagccatcg ccgcaggcgc gagcgctgtc      1080
atggtcggtt ctatgctggc gggtaccgaa gaatcccgg gcgaaatcga actctaccag       1140
ggccgttctt acaaatctta ccgcggcatg ggctcgctgg gcgcgatgtc caaaggttcc      1200
tctgaccgtt acttccagag cgacaacgcc gccgacaaac tggtgccgga aggtatcgaa      1260
ggccgcgtag cctataaagg tcgcctgaaa gagatcattc accagcagat gggcggcctg      1320
cgctcctgta tggggctgac cggttgtgct accatcgacg aactgcgtac taaagcggag      1380
tttgtgcgta tcagcggtgc gggtatccag gaaagccacg ttcacgacgt gaccatcacc      1440
aaagagtccc cgaactaccg tctgggctcc tgattttctt cgcccgacct tcgcgtcggg      1500
cgatttattt aatctgtttc acttgcctcg gaataagcgt caatgacgga aaacattcat      1560
aagcatcgca tcctcattct ggacttcggt tctcagtaca ctcaactggt tgcgcgccgc      1620
```

```
gtgcgtgagc tgggtgttta ctgcgaactg tgggcgtggg atgtgacaga agcacaaatt    1680
cgtgacttca acccaagcgg cattattctt tccggcggcc cggaaagcac caccgaagaa    1740
aacagcccgc gcgcgccgca gtatgtcttt gaagcaggcg tgccggtatt tggcgtctgc    1800
tacgggatgc agaccatggc gatgcagctt ggcggtcatg tagaaggttc taatgagcgt    1860
gaatttggtt acgcgcaggt cgaagtgctg accgacagcg cgctggttcg cggtattgaa    1920
gattccctga ccgccgacgg caaaccgctg ctggacgtgt ggatgagcca cggcgataaa    1980
gtgacggcga ttccgtccga cttcgtgacc gtagccagca ccgaaagctg cccgttcgcc    2040
atcatggcta acgaagaaaa acgcttctac ggcgtacagt tccacccgga agtgactcac    2100
acccgccagg gtatgcgcat gctggagcgt tttgtgcgtg atatctgcca gtgtgaagcc    2160
ctgtggacgc cggcgaagat catcgacgac gccgtggcgc gcattcgcga gcaggtaggc    2220
gacgataaag tgatcctcgg tctctccggc ggcgtggatt cttccgtaac cgcaatgctg    2280
ctgcaccgcg cgatcggtaa aaatctgacc tgtgtattcg tcgacaacgg cctgctgcgt    2340
ctcaacgaag ccgagcaggt gatggacatg tttggcgacc attttggtct gaacatcgtt    2400
cacgtaccgg cagaagatcg cttcctgtcc gcgttggctg cgaaaacga tccggaagcg    2460 aagcgtaaga tcattggccg tgttttgtg gaagtgttcg acgaagaagc gttgaaactg    2520
gaagacgtga atggctggc gcagggcacc atctaccctg acgtcatcga atctgcggcg    2580
tctgcaaccg gtaaagcgca cgtcatcaaa tctcaccaca atgttggcgg cctgccgaaa    2640
gagatgaaga tggggctggt tgaaccgctg aaagagctgt tcaaagacga agtgcgtaag    2700
attggtctgg agctgggcct gccgtacgac atgctgtacc gtcatccgtt cccggggccg    2760
ggcctcggcg tacgtgtact gggtgaagtg aagaaagagt actgcgacct gctgcgccgt    2820
gctgatgcca tcttcattga agagctgcgt aaggcggatc tgtacgacaa agtcagccag    2880
gcgttcaccg tcttcctgcc agtacgctcc gttggcgtaa tgggcgatgg tcgtaagtac    2940
gattgggtgg tctctctgcg tgctgtcgaa accatcgact ttatgaccgc gcactgggcg    3000
cacctgccgt atgacttcct gggtcgtgtt tccaaccgca tcatcaatga agtcaacggg    3060
atttcccgtg tggtgtatga catcagcggt aaaccaccgg ctaccattga gtgggaataa    3120
```

<210> SEQ ID NO 27
<211> LENGTH: 2147
<212> TYPE: DNA
<213> ORGANISM: Salmonella Typhi Ty2

<400> SEQUENCE: 27

```
ttattcgcca gaagcctgcg cttccggttt gccgtaaatc agcaacggct tactctgacc      60
ggcaataacg gactcgtcaa tcaccacttt ttcgacgtct tccatagatg gcaaatcgta     120
catggtatcc agcagcgccg cttcgacgat agaacgcagg ccacgggcac cagttttacg     180
cgccatcgct ttcctggcga tagcgttcag cgcttcgtca cggaattcca gatcgacgcc     240
ttccaggtta acagcgcct gatactgctt ggtcagcgca ttttttcggct ctttcaggat     300 ttgaaccagc gcttcttcgc tgagttcgtt cagcgtcgcc accactggca gacgaccgat     360
aaactcagga atcagaccaa atttgatcaa atcttccggt tcaacctgcg acaacagctc     420
gccttcactg gctttgtcgg acttcgcttt caccgtcgcg ccaaaaccaa tgccggagcc     480
ggtttcaaca cggttagcga tcactttatc agaccggca aacgcgccgc cgcagataaa     540
cagaatctta gaggtatcta cctgtaagaa ctcctgctgc ggatgtttgc gaccgccctg     600
cggtggaacc gcggcgacgg tgccttcgat cagtttcagc aacgcctgct gtacgccttc     660
```

| | |
|---|---|
| gccggaaaca tcgcgggtaa tggacggatt gtctgattta cgcgaaatct tatcgatttc | 720 |
| atcaatgtag acaatcccac gctgcgcttt ttgcacgtcg tagtcgcatt tctgcaacag | 780 |
| tttctgaatg atattctcga cgtcttcccc cacgtaaccc gcttcggtca gcgtggtcgc | 840 |
| atccgccata gtgaacggca catccagcaa gcgcgccagc gtttccgcca gcagcgtttt | 900 |
| accggaaccg gtcggtccag tcagcagaat gttgcttttg cctaactcga cgccattgct | 960 |
| ggtatcgccg ttacgcagac gcttgtagtg gttatagacc gccaccgcca gcactttttt | 1020 |
| cgcctgctcc tggccgataa cgtaatcgtc caggtgagta cgaatttcat gcggcgtcgg | 1080 |
| cagcgcacta cgttcacggt gcggagcaac ttctttaatt tcttcgcgaa taatgtcgtt | 1140 |
| acataaatcg acgcattcgt cgcagatata cacggatgga ccggcaatca gcttgcgcac | 1200 |
| ttcatgctgg cttttgccgc aaaaagagca gtacaacaat tgcccgagc catctttgcg | 1260 |
| tttatctgtc atgagtcaaa acctcttctt tgttctttgt gccgcacacg acgacgcaaa | 1320 |
| tgccattctc aggcgcaagc cgctaatcag cgttgtgccg cccttcatta gtatatacac | 1380 |
| aaaatcattc gagctacatc aaggcggcaa ctcagcgact ccgcaggcgc ttacataagt | 1440 |
| aagtcactgg gaggcgcgct ggcaaccaac accgaggtag cgtgaaggat gaagtgtata | 1500 |
| gcggcacact tgcgtccagg gcatcaatta cgatgggtca aaattgagtc aaccaaaccg | 1560 |
| tactctaccg cttcaggcgc ggagaggaag cgatcgcgct cagtatcacg ttcaatctgc | 1620 |
| tcaagagatt gacccgtatg atgcgccata agttcattca tgcgcccttt tactttcaaa | 1680 |
| atttcgcggg cgtgaatttc aatatccgtc gcctggccct gatagccgcc cagcggctgg | 1740 |
| tggatcatga cgcgagagtt cggcaagcag aaacgtttgc ctttcgcccc ggcagtcagc | 1800 |
| agaaacgccc ccatagaggc cgcctgtccc atacaaatgg tgctgacgtc tggcttaata | 1860 |
| aactgcatgg tgtcatagat ggacatcccc gcagtaatta cgccgccagg agaattaatg | 1920 |
| tacagataga tatctttttc cgggttttcc gcttccagga acagcatctg cgccacgatc | 1980 |
| aggttagcca tatggtcttc gacctggccg gtcagaaata tgacgcgttc cttaagtaga | 2040 |
| cgagaataga tatcaaaaga gcgctcaccg cgtgaggtct gttcaatgac catcggcacc | 2100 |
| agcgccatat gagggccaa attatctcgt tctccgctgt atgacat | 2147 |

<210> SEQ ID NO 28
<211> LENGTH: 687
<212> TYPE: DNA
<213> ORGANISM: E. coli

<400> SEQUENCE: 28

| | |
|---|---|
| cctagggcca gcaaaaggcc aggaaccgta aaaaggccgc gttgctggcg ttttttccata | 60 |
| ggctccgccc cctgacgag catcacaaaa atcgacgctc aagtcagagg tggcgaaacc | 120 |
| cgacaggact ataaagatac caggcgtttc cccctggaag ctccctcgtg cgctctcctg | 180 |
| ttccgaccct gccgcttacc ggatacctgt ccgcctttct cccttcggga agcgtggcgc | 240 |
| tttctcatag ctcacgctgt aggtatctca gttcggtgta ggtcgttcgc tccaagctgg | 300 |
| gctgtgtgca cgaaccccc gttcagcccg accgctgcgc cttatccggt aactatcgtc | 360 |
| ttgagtccaa cccggtaaga cacgacttat cgccactggc agcagccact ggtaacagga | 420 |
| ttagcagagc gaggtatgta ggcggtgcta cagagttctt gaagtggtgg cctaactacg | 480 |
| gctacactag aaggacagta tttggtatct gcgctctgct gaagccagtt accttcggaa | 540 |
| aaagagttgg tagctcttga tccggcaaac aaaccaccgc tggtagcggt ggtttttttg | 600 |
| tttgcaagca gcagattacg cgcagaaaaa aaggatctca agaagatcct ttgatctttt | 660 |

```
ctacggggtc tgacgctcag tagatct                                         687
```

<210> SEQ ID NO 29
<211> LENGTH: 635
<212> TYPE: DNA
<213> ORGANISM: Salmonella typhimurium

<400> SEQUENCE: 29

```
cctaggagat acttaacagg gaagtgagag ggccgcggca aagccgtttt tccataggct    60
ccgcccccct gacaagcatc acgaaatctg acgctcaaat cagtggtggc gaaacccgac   120
aggactataa agataccagg cgtttccccc tggcggctcc ctcgtgcgct ctcctgttcc   180
tgcctttcgg tttaccggtg tcattccgct gttatggccg cgtttgtctc attccacgcc   240
tgacactcag ttccgggtag gcagttcgct ccaagctgga ctgtatgcac gaaccccccg   300
ttcagtccga ccgctgcgcc ttatccggta actatcgtct tgagtccaac ccggaaagac   360
atgcaaaagc accactggca gcagccactg gtaattgatt tagaggagtt agtcttgaag   420
tcatgcgccg gttaaggcta aactgaaagg acaagttttg gtgactgcgc tcctccaagc   480
cagttacctc ggttcaaaga gttggtagct cagagaacct cgaaaaacc gcccctgcaag   540
gcggtttttt cgttttcaga gcaagagatt acgcgcagac caaaacgatc tcaagaagat   600
catcttatta atcagataaa atatttctag gatct                              635
```

<210> SEQ ID NO 30
<211> LENGTH: 1955
<212> TYPE: DNA
<213> ORGANISM: E. coli

<400> SEQUENCE: 30

```
cctaggtttc acctgttcta ttaggtgtta catgctgttc atctgttaca ttgtcgatct    60
gttcatggtg aacagcttta aatgcaccaa aaactcgtaa aagctctgat gtatctatct   120
tttttacacc gttttcatct gtgcatatgg acagttttcc ctttgatatc taacggtgaa   180
cagttgttct acttttgttt gttagtcttg atgcttcact gatagataca agagccataa   240
gaacctcaga tccttccgta tttagccagt atgttctcta gtgtggttcg ttgttttgc    300
gtgagccatg agaacgaacc attgagatca tgcttacttt gcatgtcact caaaaatttt   360
gcctcaaaac tggtgagctg aattttttgca gttaaagcat cgtgtagtgt ttttcttagt   420
ccgttacgta ggtaggaatc tgatgtaatg gttgttggta ttttgtcacc attcattttt   480
atctggttgt tctcaagttc ggttacgaga tccattgtc tatctagttc aacttggaaa   540
atcaacgtat cagtcgggcg gcctcgctta tcaaccacca atttcatatt gctgtaagtg   600
tttaaatctt tacttattgg tttcaaaacc cattggttaa gccttttaaa ctcatggtag   660
ttattttcaa gcattaacat gaacttaaat tcatcaaggc taatctctat atttgccttg   720
tgagttttct tttgtgttag ttcttttaat aaccactcat aaatcctcat agagtatttg   780
ttttcaaaag acttaacatg ttccagatta tattttatga attttttaa ctggaaaaga   840
taaggcaata tctcttcact aaaaactaat tctaattttt cgcttgagaa cttggcatag   900
tttgtccact ggaaaatctc aaagccttta accaaggat tcctgatttc cacagttctc   960
gtcatcagct ctctgttgc tttagctaat acaccataag cattttccct actgatgttc  1020
atcatctgag cgtattggtt ataagtgaac gataccgtcc gttctttcct tgtagggttt  1080
tcaatcgtgg ggttgagtag tgccacacag cataaaatta gcttggtttc atgctccgtt  1140
aagtcatagc gactaatcgc tagttcattt gctttgaaaa caactaattc agacatacat  1200
```

```
ctcaattggt ctaggtgatt ttaatcacta taccaattga gatgggctag tcaatgataa   1260
ttactagtcc ttttcctttg agttgtgggt atctgtaaat tctgctagac ctttgctgga   1320
aaacttgtaa attctgctag accctctgta aattccgcta gacctttgtg tgttttttt    1380 gtttatattc aagtggttat aatttataga ataagaaag aataaaaaaa gataaaaaga    1440
atagatccca gccctgtgta taactcacta ctttagtcag ttccgcagta ttacaaaagg   1500
atgtcgcaaa cgctgtttgc tcctctacaa aacagacctt aaaaccctaa aggcttaagt   1560
agcaccctcg caagctcggg caaatcgctg aatattcctt ttgtctccga ccatcaggca   1620
cctgagtcgc tgtcttttc gtgacattca gttcgctgcg ctcacggctc tggcagtgaa    1680
tgggggtaaa tggcactaca ggcgcctttt atggattcat gcaaggaaac tacccataat   1740
acaagaaaag cccgtcacgg gcttctcagg gcgttttatg gcgggtctgc tatgtggtgc   1800
tatctgactt tttgctgttc agcagttcct gccctctgat tttccagtct gaccacttcg   1860
gattatcccg tgacaggtca ttcagactgg ctaatgcacc cagtaaggca gcggtatcat   1920
caacaggctt acccgtctta ctgtcaaccg gatct                              1955

<210> SEQ ID NO 31
<211> LENGTH: 1686
<212> TYPE: DNA
<213> ORGANISM: Escherichia coli

<400> SEQUENCE: 31
cacttttgtt acccgccaaa caaaacccaa aaacaacca tacccaaccc aataaaacac    60
caaaacaaga caaataatca ttgattgatg gttgaaatgg ggtaaacttg acaaacaaac   120
ccacttaaaa cccaaaacat acccaaacac acaccaaaaa aacaccataa ggagttttat   180
aaatgttggt attcattgat gacggttcaa caaacatcaa actacagtgg caggaaagcg   240
acggaacaat taaacagcac attagcccga acagcttcaa acgcgagtgg gcagtctctt   300
ttggtgataa aaaggtcttt aactacacac tgaacggcga acagtattca tttgatccaa   360
tcagcccgga tgctgtagtc acaaccaata tcgcatggca atacagcgac gttaatgtcg   420
ttgcagtgca tcacgcctta ctgaccagtg gtctgccggt aagcgaagtg gatattgttt   480
gcacacttcc tctgacagag tattacgaca gaaataacca acccaatacg gaaaatattg   540
agcgtaagaa agcaaacttc cggaaaaaaa ttacattaaa tggcgggat acattcacaa    600 taaaagatgt aaaagtcatg cctgaatcta taccggcagg ttatgaagtt ctacaagaac   660
tggatgagtt agattcttta ttaattatag atctcggggg caccacatta gatatttctc   720
aggtaatggg gaaattatcg gggatcagta aaatatacgg agactcatct cttggtgtct   780
ctctggttac atctgcagta aaagatgccc tttctcttgc gagaacaaaa ggaagtagct   840
atcttgctga cgatataatc attcacagaa aagataataa ctatctgaag caacgaatta   900
atgatgagaa caaatatca atagtcaccg aagcaatgaa tgaagcactt cgtaaacttg   960
agcaacgtgt attaaatacg ctcaatgaat tttctggtta tactcatgtt atggttatag   1020
gcggtggcgc agaattaata tgcgatgcag taaaaaaaca cacacagatt cgtgatgaac   1080 gtttttcaa aaccaataac tctcaatatg atttagttaa cggtatgtat ctcataggta   1140
attaatgatg gacaagcgca gaaccattgc cttcaaacta atccagatg taaatcaaac    1200 agataaaatt gtttgtgata cactggacag tatcccgcaa ggggaacgaa gccgccttaa   1260
ccgggccgca ctgacggcag gtctggcctt atacagacaa gatccccgga cccctttcct   1320
tttatgtgag ctgctgacga agaaaccac atttcagat atcgtgaata tattgagatc    1380
```

```
gctatttcca aaagagatgg ccgattttaa ttcttcaata gtcactcaat cctcttcaca      1440
acaagagcaa aaaagtgatg aagagaccaa aaaaaatgcg atgaagctaa taaattaatt      1500
caattattat tgagttccct ttatccacta tcaggctgga taaagggaac tcaatcaagt      1560
tattttctta ccagtcatta cataatcgtt attatgaaat aatcgtttgc actgtctctg      1620
ttattcaggc aatttcaata aaggcacttg ctcacgctct gtcattttct gaaactcttc      1680
atgctg                                                                1686

<210> SEQ ID NO 32
<211> LENGTH: 367
<212> TYPE: DNA
<213> ORGANISM: Escherichia coli

<400> SEQUENCE: 32
gacagtaaga cgggtaagcc tgttgatgat accgctgcct tactgggtgc attagccagt       60
ctgaatgacc tgtcacggga taatccgaag tggtcagact ggaaaatcag agggcaggaa      120
ctgctgaaca gcaaaaagtc agatagcacc acatagcaga cccgccataa aacgccctga      180
gaagcccgtg acgggctttt cttgtattat gggtagtttc cttgcatgaa tccataaaag      240
gcgcctgtag tgccatttac ccccattcac tgccagagcc gtgagcgcag cgaactgaat      300
gtcacgaaaa agacagcgac tcaggtgcct gatggtcgga gacaaaagga atattcagcg      360
atttgcc                                                               367

<210> SEQ ID NO 33
<211> LENGTH: 459
<212> TYPE: DNA
<213> ORGANISM: Escherichia coli

<400> SEQUENCE: 33
ttctgtggta gcacagaata atgaaaagtg tgtaaagaag ggtaaaaaaa accgaatgcg       60
aggcatccgg ttgaaatagg ggtaaacaga cattcagaaa tgaatgacgg taataaataa      120
agttaatgat gatagcggga gttattctag ttgcgagtga aggttttgtt ttgacattca      180
gtgctgtcaa atacttaaga ataagttatt gattttaacc ttgaattatt attgcttgat      240
gttaggtgct tatttcgcca ttccgcaata atcttaaaaa gttcccttgc atttacattt      300
tgaaacatct atagcgataa atgaaacatc ttaaaagttt tagtatcata ttcgtgttgg      360
attattctgc attttttgggg agaatggact tgccgactga ttaatgaggg ttaatcagta      420
tgcagtggca taaaaaagca aataaaggca tataacaga                           459

<210> SEQ ID NO 34
<211> LENGTH: 734
<212> TYPE: DNA
<213> ORGANISM: Shigella flexneri 2a strain CVD 1208s

<400> SEQUENCE: 34
catatgattg acctgaatga atatacagta ttggaatgca ttatccggag tgttgtgtaa       60
caatgtctgg ccaggtttgt ttcccggaac cgaggtcaca acatagtaaa agcgctattg      120
gtaatggtac aatcgcgcgt ttacacttat tcagaacgac aggagacacg aacatggcca      180
gcagaggcgt aaacaaggtt attctcgttg gtaatctggg tcaggacccg gaagtacgct      240
acatgccaaa tggtggcgca gttgccaaca ttacgctggc tacttccgaa tcctggcgtg      300
ataaagcgac cggcgagatg aaagaacaga ctgaatggca ccgcgttgtg ctgttcggca      360
aactggcaga agtggcgagc gaatatctgc gtaaaggttc tcaggtttat atcgaaggtc      420
```

-continued

| | |
|---|---|
| agctgcgtac ccgtaaatgg accgatcaat ccggtcagga tcgctacacc acagaagtcg | 480 |
| tggtgaacgt tggcggcacc atgcagatgc tgggtggtcg tcagggtggt ggcgctccgg | 540 |
| caggtggcaa tatcggtggt ggtcagccgc agggcggttg gggtcagcct cagcagccgc | 600 |
| agggtggcaa tcagttcagc ggcggcgcgc agtctcgccc gcagcagtcc gctccggcag | 660 |
| cgccgtctaa cgagccgccg atggactttg atgatgacat tccgttctga tttgtcatta | 720 |
| aaacaatagc tagc | 734 |

<210> SEQ ID NO 35
<211> LENGTH: 1467
<212> TYPE: DNA
<213> ORGANISM: Salmonella Paratyphi A 9150
<220> FEATURE:
<221> NAME/KEY: misc_feature
<223> OTHER INFORMATION: guaB

<400> SEQUENCE: 35

| | |
|---|---|
| atgctacgta tcgctaaaga agccctgacg tttgacgacg tcctccttgt tcccgctcac | 60 |
| tccaccgttt tgccgaatac tgccgatctc agcacgcagt tgacgaaaac tattcgtctg | 120 |
| aatattccta tgctttctgc ggcgatggac accgtgacgg aagcgcgcct ggcaattgcc | 180 |
| ctggcccagg aaggcggcat tggttttatc cacaaaaaca tgtccattga gcgccaggcg | 240 |
| gaagaagttc gccgcgtgaa gaaacacgag tccggcgtag tgaccgaccc gcagaccgtc | 300 |
| ctgccaacca ccacgttgca tgaagtgaaa gccctgaccg agcgtaacgg ttttgcgggc | 360 |
| tatccggtgg tgactgaaga taacgagctg gtggggatca tcaccggtcg tgacgtgcgt | 420 |
| tttgtgactg acctgaacca gccggtaagt gtctacatga cgccgaaaga gcgtctggtg | 480 |
| accgttcgtg aaggcgaagc ccgtgaagtc gtgctggcaa aaatgcacga aaacgcgta | 540 |
| gaaaaagcgc tggtcgttga tgataacttc catctgcttg gcatgattac cgtaaaagat | 600 |
| ttccagaaag cggaacgtaa accaaactcc tgtaaagatg agcagggccg tttacgtgtc | 660 |
| ggcgcggcgg tcggcgcagg cgcgggcaac gaagagcgcg ttgacgcgct ggtggcggca | 720 |
| ggcgttgacg tactgctgat cgactcctct cacggtcact ctgaaggcgt gttgcaacgt | 780 |
| atccgtgaga gcgtgctaa atatcctgac ctgcaaatca tcggcggcaa cgttgcgacg | 840 |
| ggcgcaggcg ctcgcgcact ggcggaagcc ggttgcagcg cggtgaaagt gggtatcggc | 900 |
| ccgggctcca tctgtaccac tcgtatcgtg actggtgtgg gcgttccgca gatcaccgct | 960 |
| gtttccgacg cggtagaagc gctggaaggc accggaattc cggttatcgc tgacggcggt | 1020 |
| atccgtttct ccggcgacat cgccaaagcc atcgccgcag gcgcgagcgc cgtgatggtg | 1080 |
| ggctctatgc tggccggtac cgaagaatcc ccgggcgaaa tcgaactcta ccagggccgt | 1140 |
| tcgtacaaat cttaccgcgg catgggctcg ctgggcgcga tgtccaaagg ttcctccgac | 1200 |
| cgttacttcc agagcgacaa cgccgctgac aaactggtgc cggaaggtat cgaaggccgc | 1260 |
| gtagcctata aggtcgcct gaaagagatc attcaccagc agatgggcgg cctgcgctcc | 1320 |
| tgtatgggc tgaccggttg tgctaccatc gacgaactgc gtactaaagc ggagtttgtg | 1380 |
| cgtatcagcg gtgcgggtat ccaggaaagc cacgttcacg acgtgaccat caccaaagag | 1440 |
| tccccgaact accgtctggg ctcctga | 1467 |

<210> SEQ ID NO 36
<211> LENGTH: 1578
<212> TYPE: DNA
<213> ORGANISM: Salmonella Paratyphi A 9150
<220> FEATURE:
<221> NAME/KEY: misc_feature
<223> OTHER INFORMATION: guaA

<400> SEQUENCE: 36

| | | | | | |
|---|---|---|---|---|---|
| atgacggaaa | acattcataa | gcatcgcatc | ctcattctgg | acttcggttc | tcagtacact | 60 |
| caactggttg | cgcgccgcgt | gcgtgagctg | ggtgtttact | gcgaactgtg | ggcgtgggat | 120 |
| gtgacagaag | cacaaattcg | tgacttcaac | ccaagcggca | ttattctttc | cggcggcccg | 180 |
| gaaagcacca | ccgaagaaaa | cagcccgcgc | gcgccgcagt | atgtctttga | agcaggcgtg | 240 |
| ccggtatttg | gcgtttgcta | tggtatgcag | accatggcga | tgcagcttgg | cggtcatgta | 300 |
| gaaggttcta | tgagcgtgga | atttggttat | gcgcaggtcg | aagtgttgac | cgacagcgcg | 360 |
| ctggttcgcg | gtattgaaga | ttccctgacc | gcagacggca | aaccgctgct | ggacgtgtgg | 420 |
| atgagccacg | gcgataaagt | gacggcgatt | ccgtccgact | tcgtgaccgt | cgccagcacc | 480 |
| gagagctgcc | cgttcgccat | catggctaac | gaagaaaaac | gcttctacgg | cgtacagttc | 540 |
| cacccggaag | tgacccacac | ccgccagggg | atgcgcatgc | tggagcgttt | tgtgcgtgat | 600 |
| atctgccagt | gtgaagcgtt | gtggacgccg | gcgaagatca | tcgacgacgc | cgtggcgcgc | 660 |
| attcgcgagc | aggtaggcga | cgataaagtg | atcctcggtc | tctccggcgg | cgtggattct | 720 |
| tccgtcaccg | caatgctgct | gcaccgcgcg | atcggtaaaa | atctgacctg | tgtattcgtc | 780 |
| gacaacggcc | tgctgcgtct | caacgaagcc | gagcaggtga | tggacatgtt | tggcgaccat | 840 |
| tttggcctga | atatcgttca | cgttccggcg | aagagcgct | tcctgtccgc | gttggctggc | 900 |
| gaaaacgatc | cggaagcgaa | gcgtaagatc | attggccgtg | tttttgtgga | agtgttcgac | 960 |
| gaagaagcgt | tgaaactgga | agacgtgaaa | tggctggcgc | agggcaccat | ctaccctgac | 1020 |
| gtcatcgagt | ctgcgcgtc | tgcaaccggt | aaagcgcacg | tcatcaaatc | tcaccacaat | 1080 |
| gttggcggcc | tgccgaaaga | gatgaagatg | gggctggttg | aaccgctgaa | agagctgttc | 1140 |
| aaagacgaag | tgcgtaagat | tggtctggag | ctgggcctgc | cgtacgacat | gctgtaccgt | 1200 |
| catccgttcc | cggggccggg | cctcggcgta | cgtgtactgg | gtgaagtgaa | gaaagagtac | 1260 |
| tgcgacctgt | tgcgccgtgc | tgacgccatc | ttcattgaag | agctgcgtaa | ggcggatctg | 1320 |
| tacgacaaag | tcagccaggc | gttcaccgtc | ttcctgccag | tacgctccgt | tggcgtaatg | 1380 |
| ggcgatggtc | gtaagtacga | ttgggtggtc | tccctgcgtg | ctgtcgaaac | catcgacttt | 1440 |
| atgactgcgc | actgggcgca | tctgccgtat | gacttcctgg | gtcgtgtttc | caaccgcatc | 1500 |
| atcaatgaag | tcaacgggat | ttcccgtgtg | gtgtatgaca | tcagcggtaa | accaccggct | 1560 |
| accattgagt | gggaataa | | | | | 1578 |

<210> SEQ ID NO 37
<211> LENGTH: 624
<212> TYPE: DNA
<213> ORGANISM: Salmonella Paratyphi A 9150
<220> FEATURE:
<221> NAME/KEY: misc_feature
<223> OTHER INFORMATION: clpP

<400> SEQUENCE: 37

| | | | | | |
|---|---|---|---|---|---|
| atgtcataca | gcggagaacg | agataatttg | gcccctcata | tggcgctggt | gccgatggtc | 60 |
| attgaacaga | cctcacgcgg | tgagcgctct | tttgatatct | attctcgtct | acttaaggaa | 120 |
| cgcgtcatat | ttctgaccgg | ccaggtcgaa | gaccatatgc | taacctgat | cgtggcgcag | 180 |
| atgctgttcc | tggaagcgga | aaaccccgaa | aaagatatct | atctgtacat | taattctcct | 240 |
| ggcggcgtaa | ttactgcggg | gatctccatc | tatgacacca | tgcagtttat | taagccagac | 300 |
| gtcagcacca | tttgtatggg | acaggcgcc | tctatggggg | cgtttctgct | gactgccggg | 360 |

| | |
|---|---:|
| gcgaaaggca aacgtttctg cttgccgaac tctcgcgtca tgatccacca gccgctgggc | 420 |
| ggctaccagg gccaggcgac ggatattgaa attcacgccc gcgaaatttt gaaagtaaaa | 480 |
| gggcgcatga atgaacttat ggcgcatcat acgggtcaat ctcttgagca gattgaacgt | 540 |
| gatactgagc gcgatcgctt cctctccgcg cctgaagcgg tagagtacgg tttggttgac | 600 |
| tcaattttga cccatcgtaa ttga | 624 |

```
<210> SEQ ID NO 38
<211> LENGTH: 1272
<212> TYPE: DNA
<213> ORGANISM: Salmonella Paratyphi A 9150
<220> FEATURE:
<221> NAME/KEY: misc_feature
<223> OTHER INFORMATION: clpX

<400> SEQUENCE: 38
```

| | |
|---|---:|
| atgacagata aacgcaaaga tggctcgggc aaattgttgt actgctcttt ttgcggcaaa | 60 |
| agccagcatg aagtgcgcaa gctgattgcc ggtccatccg tgtatatctg cgacgaatgc | 120 |
| gtcgatttat gtaacgacat tattcgcgaa gaaattaaag aagttgctcc gcaccgtgaa | 180 |
| cgtagtgcgc tgccgacgcc gcatgaaatt cgtacccacc tggacgatta cgttatcggc | 240 |
| caggagcagg cgaaaaaagt gctggcggtg gcggtctata accactacaa gcgtctgcgt | 300 |
| aacggtgata ccagcaatgg cgtcgagtta ggcaaaagca acattctgct gattggaccg | 360 |
| accggttccg gtaaaacgct gctggcgaa acgctggcgc gcttgctgga tgtgccgttc | 420 |
| actatggcgg atgcgaccac gctgaccgaa gcgggttacg tgggtgaaga cgtcgagaat | 480 |
| atcattcaga aactgttgca gaaatgcgac tacgacgtgc aaaaagcgca gcgtgggatt | 540 |
| gtctacattg atgaaatcga taagatttcg cgtaaatcag acaatccgtc cattacccgc | 600 |
| gatgtttccg gcgaaggcgt acagcaggcg ttgctgaaac tgatcgaagg caccgtcgcc | 660 |
| gcggttccac cgcagggcgg tcgcaaacat ccgcagcagg agttcttaca ggtagatacc | 720 |
| tctaagattc tgtttatctg cggcggcgcg tttgctggtc tggataaagt gatcgctaac | 780 |
| cgtgttgaaa ccgctccgg cattggtttt ggcgcgacgg tgaaagcgaa gtccgacaaa | 840 |
| gccagcgaag gcgagctgtt gtcgcaggtt gaaccggaag atttgatcaa atttggtctg | 900 |
| attcctgagt ttatcggtcg tctgccagtg gtggcgacgc tgaacgaact cagcgaagaa | 960 |
| gcgctgattc aaatcctgaa agagccgaaa aatgcgctga ccaagcagta tcaggcgctg | 1020 |
| tttaacctgg aaggcgtcga tctggaattc cgtgacgaag cgctggacgc tatcgccagg | 1080 |
| aaagcaatgg cgcgtaaaac cggtgcccgt ggtctgcgtt ctatcgtcga agcggcgctg | 1140 |
| ctggatacca tgtacgattt gccatctatg gaagacgtcg aaaagtggt gatcgacgag | 1200 |
| tccgttattg ccggtcagag taagccgttg ctgatttacg gcaaaccgga agcgcaggct | 1260 |
| tctggcgaat aa | 1272 |

```
<210> SEQ ID NO 39
<211> LENGTH: 1272
<212> TYPE: DNA
<213> ORGANISM: Salmonella Typhi Ty2
<220> FEATURE:
<221> NAME/KEY: misc_feature
<223> OTHER INFORMATION: clpX gene

<400> SEQUENCE: 39
```

| | |
|---|---:|
| atgacagata aacgcaaaga tggctcgggc aaattgttgt actgctcttt ttgcggcaaa | 60 |
| agccagcatg aagtgcgcaa gctgattgcc ggtccatccg tgtatatctg cgacgaatgc | 120 |

```
gtcgatttat gtaacgacat tattcgcgaa gaaattaaag aagttgctcc gcaccgtgaa    180
cgtagtgcgc tgccgacgcc gcatgaaatt cgtactcacc tggacgatta cgttatcggc    240
caggagcagg cgaaaaaagt gctggcggtg gcggtctata accactacaa gcgtctgcgt    300
aacggcgata ccagcaatgg cgtcgagtta ggcaaaagca acattctgct gactggaccg    360
accggttccg gtaaaacgct gctggcgaaa acgctggcgc gcttgctgga tgtgccgttc    420
actatggcgg atgcgaccac gctgaccgaa gcgggttacg tgggggaaga cgtcgagaat    480
atcattcaga aactgttgca gaaatgcgac tacgacgtgc aaaaagcgca gcgtgggatt    540
gtctacattg atgaaatcga taagatttcg cgtaaatcag acaatccgtc cattacccgc    600
gatgtttccg gcgaaggcgt acagcaggcg ttgctgaaac tgatcgaagg caccgtcgcc    660
gcggttccac cgcagggcgg tcgcaaacat ccgcagcagg agttcttaca ggtagatacc    720
tctaagattc tgtttatctg cggcggcgcg tttgccggtc tggataaagt gatcgctaac    780
cgtgttgaaa ccggctccgg cattggtttt ggcgcgacgg tgaaagcgaa gtccgacaaa    840
gccagtgaag gcgagctgtt gtcgcaggtt gaaccggaag atttgatcaa atttggtctg    900
attcctgagt ttatcggtcg tctgccagtg gtggcgacgc tgaacgaact cagcgaagaa    960
gcgctggttc aaatcctgaa agagccgaaa atgcgctga ccaagcagta tcaggcgctg    1020
tttaacctgg aaggcgtcga tctggaattc cgtgacgaag cgctgaacgc tatcgccagg    1080
aaagcgatgg cgcgtaaaac tggtgcccgt ggcctgcgtt ctatcgtcga agcggcgctg    1140
ctggatacca tgtacgattt gccatctatg gaagacgtcg aaaaagtggt gattgacgag    1200
tccgttattg ccggtcagag taagccgttg ctgatttacg gcaaaccgga agcgcaggct    1260
tctggcgaat aa                                                      1272

<210> SEQ ID NO 40
<211> LENGTH: 624
<212> TYPE: DNA
<213> ORGANISM: Salmonella Typhi Ty2
<220> FEATURE:
<221> NAME/KEY: misc_feature
<223> OTHER INFORMATION: clpP gene

<400> SEQUENCE: 40
atgtcataca gcggagaacg agataatttg gccccctcata tggcgctggt gccgatggtc     60
attgaacaga cctcacgcgg tgagcgctct tttgatatct attctcgtct acttaaggaa    120
cgcgtcatat ttctgaccgg ccaggtcgaa gaccatatgc taacctgat cgtggcgcag    180 atgctgttcc tggaagcgga aaacccggaa aaagatatct atctgtacat taattctcct    240
ggcggcgtaa ttactgcggg gatgtccatc tatgacacca tgcagtttat taagccagac    300
gtcagcacca tttgtatggg acaggcggcc tctatggggg cgtttctgct gactgccggg    360
gcgaaaggca aacgtttctg cttgccgaac tctcgcgtca tgatccacca gccgctgggc    420
ggctatcagg gccaggcgac ggatattgaa attcacgccc gcgaaatttt gaaagtaaaa    480
gggcgcatga atgaacttat ggcgcatcat acgggtcaat ctcttgagca gattgaacgt    540
gatactgagc gcgatcgctt cctctccgcg cctgaagcgg tagagtacgg tttggttgac    600 tcaatttga cccatcgtaa ttga                                           624

<210> SEQ ID NO 41
<211> LENGTH: 32
<212> TYPE: DNA
<213> ORGANISM: Artificial Sequence
<220> FEATURE:
```

-continued

<223> OTHER INFORMATION: chemically-synthesized oligonucleotide primer

<400> SEQUENCE: 41
tcacgcacac gctgcaggtt gttgttgatt tc                              32

<210> SEQ ID NO 42
<211> LENGTH: 47
<212> TYPE: DNA
<213> ORGANISM: Artificial Sequence
<220> FEATURE:
<223> OTHER INFORMATION: chemically-synthesized oligonucleotide primer

<400> SEQUENCE: 42
gaacttcgaa gcagctccag cacctaatga tgaaattgaa gccatgc              47

<210> SEQ ID NO 43
<211> LENGTH: 21
<212> TYPE: DNA
<213> ORGANISM: Artificial Sequence
<220> FEATURE:
<223> OTHER INFORMATION: chemically-synthesized oligonucleotide primer

<400> SEQUENCE: 43
gctggagctg cttcgaagtt c                                          21

<210> SEQ ID NO 44
<211> LENGTH: 33
<212> TYPE: DNA
<213> ORGANISM: Artificial Sequence
<220> FEATURE:
<223> OTHER INFORMATION: chemically-synthesized oligonucleotide primer

<400> SEQUENCE: 44
ctcgagttcc ggggatccgt cgacctgcag ttc                             33

<210> SEQ ID NO 45
<211> LENGTH: 34
<212> TYPE: DNA
<213> ORGANISM: Artificial Sequence
<220> FEATURE:
<223> OTHER INFORMATION: chemically-synthesized oligonucleotide primer

<400> SEQUENCE: 45
ggatccgcta tgaacaagtc ctgataacag aggt                            34

<210> SEQ ID NO 46
<211> LENGTH: 46
<212> TYPE: DNA
<213> ORGANISM: Artificial Sequence
<220> FEATURE:
<223> OTHER INFORMATION: chemically-synthesized oligonucleotide primer

<400> SEQUENCE: 46
ctcgagttaa cgagactcct ggaaagatgc tttcggtgaa atctgc               46

<210> SEQ ID NO 47
<211> LENGTH: 2363
<212> TYPE: DNA
<213> ORGANISM: Salmonella enterica serovar Typhimurium

<400> SEQUENCE: 47
tcacgcacac gctgcaggtt gttgttgatt tcgttcagcg cgccttcagt ggtctgcgca    60
atggagatac cgtcgttagc gttacgggaa gcctgagtca gacctttgat gttcgcggta   120
aaacggttag caatcgcctg acctgccgca tcgtctttcg cgctgttgat acgcagaccg   180

```
gaagacagac gctcgatagc ggtgcccaga gcggactggg atttgttcag gttattctgg    240
gtcaacagcg acaggctgtt tgtattaatg acttgtgcca tgatcttttc cttatcaatt    300
acaacttgat gttattgggc tgttgcccac ggtttctcac cgtaaccctt gtatcggcac    360
ctgaatttcg aactttagaa aattttcac ttcccccgat cttttcctta ggcggcgaaa     420
tagccgcttt atgcatcatt attccgcgca ttattttgc aaaattatca ttaaactttg     480
cctccagatt gccgataacg cgcttaacta ctgtttgcaa tcaaaaagga agaaggcatg    540
gcttcaattt catcattagg tgtgggatca aacttaccgt tagaccagtt gttgacagac    600
ctgacaaaga acgaaaaagg acgcttaacg ccaattacca aacagcagag cgcgaattcg    660
gcaaagctaa ccgcctatgg cacattgaaa agcgcattag aaaaattcca gacggcaaat    720
accgcgttaa ataaagcgga tttatttaag tctaccgtgg cgtccagcac cactgaagat    780
ctcaaagtca gtactaccgc tggcgctgcc gcagggactt ataagattaa cgtaacccag    840
cttgccgccg cacagtcgct ggcgacaaaa accaccttcg cgaccaccaa agagcagttg    900
ggcgatacgt cggtcacgtc ccggacaatt aaaattgaac agccgggacg taaagagccg    960
ctggaaatta agctggataa aggcgacacc tccatggagg cgatccgtga cgccatcaat   1020
gacgccgaca gcggtatcgc cgccagtatc gttaaggtca agagaacga attccagttg    1080
gtgcttaccg ccaatagcgg taccgacaat acgatgaaga tcacggtgga aggcgataca   1140
aaacttaacg atctactcgc ttatgacagc accaccaata ccggcaatat gcaagagctg   1200
gtgaaagcag aaaacgcgaa gctgaacgta acggcatcg acattgagcg tcagagcaat    1260
accgtaaccg acgcccctca gggaattacg ctcaccctga ccaagaaagt gaccgacgcg   1320
accgtgacgg taacgaaaga tgataccaag gcgaaagagg cgattaaatc ctgggtggat   1380
gcctataact cgctggtgga tacctttagc tcgttaacca aatataccgc cgttgagccg   1440
ggcgaagaag ccagcgataa aaacggcgcg ctgttaggcg atagtgtggt tcgtactatc   1500
cagaccggga ttcgggcaca atttgccaat agcggcagta attctgcgtt caaaacaatg   1560
gcggaaattg gcatcaccca ggatgggact tccggcaaac tgaagattga tgatgataag   1620
ctgaccaaag tactgaaaga taacacagcc gcagcgcgtg agctgctggt aggcgatggt   1680
aaagaaacgg gtatcaccac caaaattgcc accgaagtga aagttatct ggcggatgac     1740
ggcattattg ataatgcgca ggacaacgtt aacgccacgc tgaaaagcct gacaaaacag   1800
tacctgtccg ttagcaacag catcgatgaa accgttgccc gttacaaggc ccagtttacc   1860
caactggata ccatgatgag taagctgaat aacaccagta gttatttgac ccagcaattt   1920
acagctatga acaagtcctg ataacagagg tcaccatgta caccgcgagc ggtatcaaag   1980
cttatgcgca agtcagcgtg gaaagcgccg tgatgagcgc cagcccgcat cagttgattg   2040
aaatgttgtt tgatggcgcg aatagcgctc tggtgcgcgc tcgcctgttt ttagaacaag   2100
gcgatgttgt cgcgaaaggt gaagcgttaa gcaaagccat caatattatc gataacgggc   2160
tgaaagccgg cctcgatcag gaaaaggcg gtgagattgc gacgaatctt tccgagctat    2220
acgactatat gattcgccgt ttactgcagg ctaatttgcg taacgacgct caggccatcg   2280
aagaagtgga agggttactc agcaatattg cagaagcctg gaagcagatt tcaccgaaag   2340
catctttcca ggagtctcgt taa                                           2363

<210> SEQ ID NO 48
<211> LENGTH: 2363
<212> TYPE: DNA
<213> ORGANISM: Salmonella enterica serovar Paratyphi A
```

<400> SEQUENCE: 48

```
tcacgcacac gctgcaggtt gttgttgatt tcgttcagcg cgccttcagt ggtctgcgca      60
atggagatac cgtcgttagc gttacgggaa gcctgagtca gacctttgat gttcgcggtg     120
aaacggttag caattgcctg acctgccgca tcgtctttcg cgctgttgat acgcagaccg     180
gaagacagac gctcgatagc ggtgcccaga gcggactggg atttgttcag gttattctgg     240
gtcaacagcg acaggctgtt tgtattaatg acttgtgcca tgatcttttc cttatcaatt     300
acaacttgat gttattgggc tgttgcccac ggtttctcac cgtaacccct tgtatcggca     360
ctgaatttcg aactttagaa aattttttcac ttcccccgat cttttcttag gcggcgaaa     420
tagccgcttt atgcatcatt attccgcgca ttattttgc aaaattatca ttaaactttg      480
cctccagatt gccgataacg cgcttaacta ctgtttgcaa tcaaaaagga agaaggcatg     540
gcttcaattt catcattagg tgtgggatca aacttaccgt tagaccagtt gttgacagac     600
ctgacaaaga acgaaaaagg acgcttaacg ccaattacca aacagcagag cgcgaattcg     660
gcaaagctaa ccgcctatgg cacattgaaa agcgcattag aaaaattcca gacggcaaat     720
accgcgttaa ataaagcgga tttatttaag tctaccgtgg cgtccagcac gacagaggac     780
ctcaaagtca gtactaccgc aggcgctgcc gcagggactt ataagattag cgtaacccag     840
cttgccgccg cgcagtcgct ggcgacaaaa accaccttcg caaccaccaa agagcagttg     900
ggcgatacgt cggtcacgtc ccggacaatt aaaattgaac agccgggacg taaagagccg     960
ctggaaatta agctggataa aggcgacacc tccatggagg cgatccgtga cgccatcaat    1020
gacgccgaca gcggtatcgc cgccagtatc gttaaggtca agagaacga attccagttg     1080
gtgcttaccg ccaatagcgg taccgacaat acgatgaaga tcacggtgga aggcgataca    1140
aaacttaacg atctactcgc ttatgacagc accaccaata ccggcaatat gcaagagctg    1200
gtgaaagcag aaaacgcgaa gctgaacgta acggcatcg acattgagcg tcagagcaat    1260
accgtaaccg acgcccctca gggaattacg ctcaccctga cgaagaaagt gaccgacgcg    1320
accgtgacgg taacgaaaga tgataccaag gcgaaagagg cgattaaatc ctgggtggat    1380
gcctataact cgctggtgga tacctttagc tcgttaacca atataccgc cgttgagccg     1440
ggcgaagaag ccagcgataa aaacggcgcg ctgttaggcg atagtgtggt tcgtactatc    1500
cagaccggga ttcgggcaca atttgccaat agcggcagta attctgcgtt caaaacaatg    1560
gcggaaattg gcatcaccca ggatgggact tccggcaaac tgaagattga tgatgataag    1620
ctgaccaagg tactgaaaga taacacagcc gcagcgcgtg agctgctggt aggcgatggt    1680
aaagaaacgg gtatcaccac caaaattgcc accgaagtga aagttatct ggcggatgac     1740
ggcattattg ataatgcgca ggacaacgtt aacgccacgc tgaaaagcct gacaaaacag    1800
tacctgtccg ttagcaacag catcgatgaa accgttgccc gttacaaggc ccagtttacc    1860
caactggata ctatgatgag taagctgaat aacaccagta gttatttgac ccagcaattt    1920
acagctatga acaagtcctg ataacagagg tcaccatgta caccgcgagc ggtatcaaag    1980
cttatgcgca agtcagcgtg gaaagcgccg tgatgagcgc cagcccgcat cagttgattg    2040
aaatgttgtt tgatggcgcg aatagcgctc tggtgcgcgc tcgcctgttt ttagaacaag    2100
gcgatgttgt cgcgaaaggt gaagcgttaa gcaaagccat caatattatc gataacgggc    2160
tgaaagccgg cctcgatcag gaaaaaggcg gtgagattgc gacgaatctt tccgagctat    2220
acgactatat gattcgccgt ttactgcagg ctaatttgcg taacgacgct caggccatcg    2280
aagaagtgga agggttactc agcaatattg cagaagcctg gaagcagatt tcaccgaaag    2340
```

| | |
|---|---:|
| catctttcca ggagtctcgt taa | 2363 |

<210> SEQ ID NO 49
<211> LENGTH: 2363
<212> TYPE: DNA
<213> ORGANISM: Salmonella enterica serovar Typhi strain Ty2

<400> SEQUENCE: 49

| | |
|---|---:|
| tcacgcacac gctgcaggtt gttgttgatt tcgttcagcg cgccttcagt ggtctgcgca | 60 |
| atggagatac cgtcgttagc gttacgggaa gcctgagtca gacctttgat gttcgcggta | 120 |
| aaacggttag caatcgcctg tcctgccgca tcgtctttcg cgctgttgat acgcagaccg | 180 |
| gaagacaaac gctcgatagc agtgcccagt gcggactggg atttgttcag gttattctgg | 240 |
| gtcaacagcg acaggctgtt tgtattaatg acttgtgcca tgatcttttc cttatcaatt | 300 |
| acaacttgat gttattgggc tgttgcccac ggtttctcac cgtaacccct tgtatcggca | 360 |
| ctgaatttcg aactttagaa aattttttcac ttcccccgat cttttttctta ggcggcgaaa | 420 |
| tagccgcttt atgcatcatt attccgcgca ttattttgc aaaattatca ttaaactttg | 480 |
| cctccagatt gccgataacg cgcttaacta ctgtttgcaa tcaaaaagga agaaggcatg | 540 |
| gcttcaattt catcattagg tgtgggatca aacttaccgt tagaccagtt gttgacagac | 600 |
| ctgacaaaga acgaaaaagg acgcttaacg ccaattacca aacagcagag cgcgaattcg | 660 |
| gcaaagctaa ccgcctatgg cacattgaaa agcgcattag aaaaattcca gacggcaaat | 720 |
| accgcgttaa ataaagcgga tttatttaag tctaccgtgg cgtccagcac gacagaggac | 780 |
| ctcaaagtca gtactaccgc aggcgctgcc gcagggactt ataagattag cgtaacccag | 840 |
| cttgccgccg cgcagtcgct ggcgacaaaa accaccttcg caaccaccaa agagcagttg | 900 |
| ggcgatacgt cggtcacatc ccggacaatt aaaattgaac agccgggacg taaagagccg | 960 |
| ctggaaatta agctggataa aggcgacacc tccatggagg cgatccgtga cgccattaat | 1020 |
| gacgccgaca gcggtatcgc cgccagtatc gttaaggtca agagaacga attccagttg | 1080 |
| gtgcttaccg ccaatagcgg taccgacaat acgatgaaga tcacggtgga aggcgataca | 1140 |
| aaacttaacg atctactcgc ttatgacagc accaccaata ccggcaatat gcaagagctg | 1200 |
| gtgaaagcag aaaacgcgaa gctgaacgta acggcatcg acattgagcg tcagagcaat | 1260 |
| accgtaaccg acgcccctca gggaattaca ctcaccctga ccaagaaagt gaccgacgcg | 1320 |
| accgtgacgg tgacgaaaga tgataccaag gcgaagagg cgattaaaatc ctgggtggat | 1380 |
| gcctataact cgctggtgga tacttttagc tcattaacta aatataccgc cgttgagccg | 1440 |
| ggcgaagaag ccagcgataa aaacggcgcg ctgttaggcg atagtgtggt tcgtgctatc | 1500 |
| cagacccgga ttcgggcaca atttgccaat agcggcagta attctgcgtt caaaacaatg | 1560 |
| gcggaaattg gcatcaccca ggatgggact tccggcaaac tgaagattga cgatgataag | 1620 |
| ctgaccaagg tactgaaaga taacacggcc gcagcgcgtg agctgctggt aggcgatggt | 1680 |
| aaagaaacgg gtatcaccac caaaattgcc accgaagtga aagttatct ggcggatgac | 1740 |
| ggcattattg ataatgcgca ggacaacgtt aacgccacgc tgaaaagcct gacaaaacag | 1800 |
| tacctgtccg ttagcaacag catcgatgaa accgttgccc gttacaaggc ccagtttacc | 1860 |
| caactggata ccatgatgag taagctgaat aacaccagta gttatttgac ccagcaattt | 1920 |
| acagctatga acaagtcctg ataacagagg tcaccatgta caccgcgagc ggtatcaaag | 1980 |
| cttatgcgca agtcagcgtg gaaagcgccg tgatgagcgc cagcccgcat cagttgattg | 2040 |
| aaatgttgtt tgatggcgcg aatagcgctc tggtgcgcgc tcgcctgttt ttagaacaag | 2100 |

```
gcgatgttgt cgcgaaaggt gaagcgttaa gcaaagccat caatattatc gataacgggc    2160
tgaaagccgg cctcgatcag gaaaaaggcg gtgagattgc gacgaatctt tccgagctat    2220
acgactatat gattcgccgt ttactgcagg ctaatttgcg taacgacgct caggccatcg    2280
aagaagtgga aaggttactc agcaatattg cagaagcctg gaagcagatt tcaccgaaag    2340
catctttcca ggagtctcgt taa                                            2363
```

<210> SEQ ID NO 50
<211> LENGTH: 2365
<212> TYPE: DNA
<213> ORGANISM: Salmonella enterica serovar Enteritidis

<400> SEQUENCE: 50

```
tcacgcacac gctgcaggtt gttgttgatt tcattcagcg caccttcagt ggtctgcgca      60
atagaaatgc cgtcgttagc gttacgggaa gcctgagtca gacctttgat attagaagtg     120
aagcggttag caatcgcctg gcctgccgca tcgtctttcg cgctgttgat acgcagacca     180
gaggacagac gctcaatagc ggaactcagt gaggactgag atttgttcag gttattctgg     240
gtcaacagcg acaggctgtt tgtattaatg acttgtgcca tgatcttttc cttatcaatt     300
acaacttgat gttattgggc tgttgcccac ggtttctcac cgtaacccct tgtatcggcac     360 ctgaatttcg aactttagaa aatttttcac ttcccccgat cttttttctta gcctgcgaaa    420 tagccgcttt atgcatcatt attccacgca ttattttgc aaaattatca ttaaactttg      480
cttccagatt gccgataacg cgtttaacta ctgtttgcaa tcgaaaggaa gatggcatgg     540
cttcaatttc atcattaggt gtagggtcaa acttacctct ggattcactg ctgactaaac     600
tgaccaacgc tgaaaaagga cgcttaacgc cgatcacaca gcagcagagt gctaatacgg     660
cccgtctaac ggcatacggt actttaaaaa gtgcactgga gaagtttcaa acagcaaaca    720
cggcgttaaa taaagccgat ctgtttaaaa gtacgaatgt caccagcagt acagaagacc    780
tgaaagtctc gacggaagct ggggccgcac ctggaactta tgtggttagc gtaactcagt    840
tagcacaagc acaatctttg agtacagcaa ccaaaattac atctaccaaa gaagtgctgg    900
gagataccac atctgacagc cgtaccataa aaattgaaca gaaaggccgt aaagaaccac    960
ttgaaatcaa gctcactaaa gatcaaacct ctttagaggg tatccgtgac gccattaatg   1020
atgctgacag tggtatttcc gccagtatcg ttaaagttaa agaaggcgat tatcagcttg   1080
tactgaccgc agatagtggc acggataatc aaatgactat ctctgtggaa ggcgatagca   1140
aactcagcga tctgttgtcc tatgatagta gtactgcgca gggcaaaatg aagcaactgg   1200
ttgctgcaga taatgctttg ttaaccgtta acggcattga tattgagcga ccgagtaata   1260
aaatcactga cgctccacaa ggcgtgacgc ttgaactaac caagaagta aaagatgccc    1320 gtattaccgt cacaaaagat aatgaaaagg cgaccgaagc cgtcaaaggt tgggttgatg   1380
cctacaactc actgcttgat accttttagtt cattaacaaa atatacagag ttgatccag    1440 gggctgaaga acaggacaaa aacaacggtg cactacttgg agataccgtg gtgcgaacga   1500
ttcaaactgg aatccgcgct cagttcgcta atggtgcaag tacaggtaca tttaagaccc   1560
tgaatgaaat tggtattact tctgatggta ccaccggaaa actaaaaatt gatgatacca   1620
agcttaaaaa agcgctggat gaaaatccg cttctgtacg tgagctgctg gtaggtgatg   1680
gtaaagaaac ggggatcacc accaaaattg ccaccgaagt gaaaagttat ctggccgatg   1740
acggcattat tgacagcgcc caggacagta ttaacgccac gctgaaaaag ctgactaagc   1800
aatatctgac cgtcagcagt agcattgacg acaccgttgc ccgttacaag gcccagttta   1860
```

-continued

| | |
|---|---|
| cccaactgga taccatgatg agtaagctga ataacaccag tacttatttg acccagcaat | 1920 |
| ttaatgctat gaacaagtcc tgataacaga ggttaccatg tacaccgcga gcggtatcaa | 1980 |
| agcttatgcg caagtcagcg tggaaagcgc cgtgatgagc gccagcccgc atcagttgat | 2040 |
| tgaaatgttg tttgatggcg cgaatagcgc tctggtgcgc gctcgcctgt ttttagaaca | 2100 |
| aggcgatgtt gtcgcgaaag gtgaagcgtt aagcaaagcc atcaatatta tcgataacgg | 2160 |
| gctgaaagcc ggcctcgatc aggaaaaagg cggtgagatt gcgacgaatc tttccgagct | 2220 |
| atacgactat atgattcgcc gtttactgca ggctaatttg cgtaacgacg ctcaggccat | 2280 |
| cgaagaagtg gaagggttac tcagcaatat tgcagaagcc tggaagcaga tttcaccgaa | 2340 |
| agcatctttc caggagtctc gttaa | 2365 |